(12) United States Patent
Conradie et al.

(10) Patent No.: US 9,988,654 B2
(45) Date of Patent: *Jun. 5, 2018

(54) METHODS, REAGENTS AND CELLS FOR BIOSYNTHESIZING COMPOUNDS

(71) Applicant: INVISTA North America S.á r.l., Wilmington, DE (US)

(72) Inventors: Alex Van Eck Conradie, Eaglescliffe (GB); Adriana Leonora Botes, Rosedale East (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 85 days.

This patent is subject to a terminal disclaimer.

(21) Appl. No.: 14/740,749

(22) Filed: Jun. 16, 2015

(65) Prior Publication Data

US 2015/0361463 A1 Dec. 17, 2015

Related U.S. Application Data

(60) Provisional application No. 62/012,674, filed on Jun. 16, 2014, provisional application No. 62/012,735, filed on Jun. 16, 2014.

(51) Int. Cl.

| | | |
|---|---|---|
| *C12P 7/62* | (2006.01) |
| *C12P 7/44* | (2006.01) |
| *C12P 13/00* | (2006.01) |
| *C12P 7/42* | (2006.01) |
| *C12P 7/18* | (2006.01) |
| *C12P 11/00* | (2006.01) |
| *C12N 9/16* | (2006.01) |
| *C12N 9/10* | (2006.01) |
| *C12N 9/02* | (2006.01) |
| *C12N 9/18* | (2006.01) |
| *C07C 69/533* | (2006.01) |
| *C12P 7/24* | (2006.01) |
| *C12P 7/40* | (2006.01) |
| *C12P 17/10* | (2006.01) |

(52) U.S. Cl.
CPC ............. *C12P 7/62* (2013.01); *C07C 69/533* (2013.01); *C12N 9/0008* (2013.01); *C12N 9/1029* (2013.01); *C12N 9/1096* (2013.01); *C12N 9/16* (2013.01); *C12N 9/18* (2013.01); *C12P 7/18* (2013.01); *C12P 7/24* (2013.01); *C12P 7/40* (2013.01); *C12P 7/42* (2013.01); *C12P 7/44* (2013.01); *C12P 11/00* (2013.01); *C12P 13/001* (2013.01); *C12P 13/005* (2013.01); *C12P 17/10* (2013.01); *C12Y 102/99006* (2013.01); *C12Y 203/01016* (2013.01); *C12Y 206/01018* (2013.01); *C12Y 206/01019* (2013.01); *C12Y 206/01029* (2013.01); *C12Y 206/01048* (2013.01); *C12Y 206/01082* (2013.01); *C12Y 301/01085* (2013.01); *C12Y 301/02* (2013.01)

(58) Field of Classification Search
None
See application file for complete search history.

(56) References Cited

U.S. PATENT DOCUMENTS

| | | | |
|---|---|---|---|
| 2,439,513 A | 4/1948 | Hamblet et al. |
| 2,557,282 A | 6/1951 | Hamblet et al. |
| 2,791,566 A | 5/1957 | Jeffers |
| 2,840,607 A | 6/1958 | Attane, Jr. et al. |
| 2,971,010 A | 2/1961 | Gilby, Jr. et al. |
| 3,023,238 A | 2/1962 | Chapman et al. |
| 3,338,959 A | 8/1967 | Sciance et al. |
| 3,365,490 A | 1/1968 | Arthur et al. |
| 3,515,751 A | 6/1970 | Oberster |
| 3,719,561 A | 3/1973 | Tanaka et al. |
| 4,058,555 A | 11/1977 | Mims |
| 6,255,451 B1 | 7/2001 | Koch et al. |
| 6,372,939 B1 | 4/2002 | Bunnel et al. |
| 8,088,607 B2 | 1/2012 | Buggard et al. |
| 8,361,769 B1 | 1/2013 | Koch et al. |
| 2004/0054235 A1 | 3/2004 | Fodor et al. |
| 2010/0035309 A1 | 2/2010 | Havemen et al. |
| 2010/0151536 A1 | 6/2010 | Baynes et al. |
| 2010/0203600 A1 | 8/2010 | Dubois |
| 2010/0298612 A1 | 11/2010 | Behrouzian et al. |

(Continued)

FOREIGN PATENT DOCUMENTS

EP 2647718 10/2013
WO WO 2008/006037 1/2008

(Continued)

OTHER PUBLICATIONS

"Enterococcus faecalis V583 bifuntional acetaldehyde-CoA/Alcohol Dehydrogenase," biocyc.org, retrieved on Jun. 19, 2014, http://biocyc.org/EFAE226185/N_EW-IMAGE?type=ENZYME &object=GH11-877-MONOMER, 9 pages.
"Information on EC 1.2.1.57-butanal dehydrogenase," brenda-enzymes.org, retrieved on Jun. 19, 2014, http://www.brenda-enzymes.org/php/result_flat.php4?ecno=1.2.1.57, 6 pages.
"BRENDA—The comprehensive Enzyme Information System," Jul. 2011, retrieved on Sep. 19, 2014, http://web.archive.org/web/20111009205602/http://www.brenda-enzymes.org/, 1 page.
Aimin et al., "*Nocardia* sp. carboxylic acid reductase: cloning, expression, and characterization of a new aldehyde oxidoreductase family," Appl. Environ. Microbiol., 2004, 70:1874-1881.

(Continued)

*Primary Examiner* — Anand U Desai
(74) *Attorney, Agent, or Firm* — William J. Simmons; Thomas H. Jenkins

(57) ABSTRACT

This document describes biochemical pathways for producing 2,3-dehydroadipyl-CoA methyl ester from precursors such as 2-oxoglutarate using one or more of a fatty acid O-methyltransferase, a thioesterase, a CoA-transferase and a CoA ligase, as well as recombinant hosts expressing one or more of such enzymes. 2,3-dehydroadipyl-CoA methyl ester can be enzymatically converted to adipyl-CoA using a trans-2-enoyl-CoA reductase, and a methylesterase, which in turn can be enzymatically converted to adipic acid, 6-aminohexanoate, 6-hydroxyhexanoate, caprolactam, hexamethylenediamine, or 1,6-hexanediol.

21 Claims, 37 Drawing Sheets

(56) References Cited

U.S. PATENT DOCUMENTS

| | | |
|---|---|---|
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2013/0065279 A1 | 3/2013 | Burk et al. |
| 2013/0183728 A1 | 7/2013 | Botes |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2013/0267012 A1 | 10/2013 | Steen et al. |
| 2014/0186902 A1 | 7/2014 | Botes et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |
| 2015/0111262 A1 | 4/2015 | Botes et al. |
| 2015/0267211 A1 | 9/2015 | Botes et al. |
| 2015/0361458 A1 | 12/2015 | Botes et al. |

FOREIGN PATENT DOCUMENTS

| | | |
|---|---|---|
| WO | WO 2008/145737 | 12/2008 |
| WO | WO 2009/121066 | 1/2009 |
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/093865 | 6/2014 |
| WO | WO 2014/105788 | 7/2014 |
| WO | WO 2014/105793 | 7/2014 |
| WO | WO 2014/105794 A2 | 7/2014 |

OTHER PUBLICATIONS

Akita et al., "Highly stable meso-diaminopimelate dehydrogenase from an Ureibacillus thermosphaericus strain A1 isolated from a Japanese compost: purification, characterization and sequencing," AMB Express, 2011, 1:43, 8 pages.

Alber et al., "Malonyl-coenzyme A reductase in the modified 3-hydroxypropionate cycle for autotrophic carbon fixation in archaeal *Metallosphaera* and *Sulfolobus* spp," J. Bacteriology, 2006, 188:8551-8559.

Aloulou et al., "Purification and biochemical characterization of the LIP2 lipase from Yarrowia lipolytica," Biochim. Biophys. Acta, 2007, 1771:228-237.

Anton et al., Polyamides, Fibers, Encyclopedia of Polymer Science and Engineering, 2001, 11:409-445.

Atsumi et al., "Acetolactate synthase from *Bacillus subtilis* serves as a 2-ketoisovalerate decarboxylase from isobutanol synthesis in *Escherichi coli*," Applied and Environ. Microbiol., 2009, 75(19):6306-6311.

Aursnes et al., "Total Synthesis of the Lipid Mediator PD1(n-3 DPA): Configurational Assignments and Anti-Inflammatory and Pro-resolving Actions," Journal of Natural Products, Feb. 2014, 77:910-916.

Azuma et al., "Naphthalene—a constituent of Magnolia flowers," Phytochemistry, 1996, 42:999-1004.

Barker et al., "Enzymatic reactions in the degradation of 5-aminovalerate by Clostridium aminovalercum," J Biol Chem., 1987, 262(19):8994-9003.

Becker et al., "Metabolic flux engineering of L-lysine production in Corynebacterium glutamicum—over expression and modification of G6P dehydrogenase," J Biotechnol. 2007, 132(2):99-109.

Bellmann et al., "Expression control and specificity of the basic amino acid exporter LysE of Corynebacterium glutamicum," Microbiology 2001, 147:1765-1774.

Bennett et al., "Purification and properties of ε-caprolactone hydrolases from Acinetobacter NCIB 9871 and Nocardia globevula CL1," Journal of General Microbiology, 1988 134: 161-168.

Bergler et al., "Protein EnvM is the NADH-dependent enoyl-ACP reductase (FabI) of *Escherichia coli*," J. Bio Chem, 1993, 269(8):5493-5496.

Bernstein et al., "Transfer of the high-GC cyclohexane carboxylate degradation pathway from Rhodopseudomonas palustris to *Escherichia coli* for production of biotin," Metabolic Engineering, May 2008, 10(3-4):131-140.

Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.

Binieda et al., "Purification, characterization, DNA Sequence and cloning of a pimeloyl-CoA synthetase from Pseudomonas medocin 35," Biochem J., 1999, 340:793-801.

Bond-Watts et al., "Biochemical and Structural Characterization of the trans-Enoly-CoA Reductase from Treponema denticola," Biochemistry, 2012, 51:6827-6837.

Bordeaux et al., "Catalytic, Mild, and Selective Oxyfunctionalization of Linear Alkanes: Current challenges," Angew. Chem. Int. Ed., 2012, 51:10712-10723.

Bordes et al., "Isolation of a thermostable variant of Lip2 lipase from Yarrowia lipolytica by directed evolution and deeper insight into the denaturation mechanisms," Journal of Biotechnology, 2011, 156: 117-124.

Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.

Boylan et al., "Functional identification of the fatty acid reductase components encoded in the luminescence operon of Vibrio fischeri," Journal of Bacteriology, 1985, 163(3):1186-1190.

Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.

Bramer et al., "The methylcitric acid pathway in Ralstonia eutropha: new genes identified involved in propionate metabolism," Microbiology 2001, 147:2203-2214.

Breithaupt et al., "Crystal structure of 12-oxophytodienoate reductase 3 from tomato: self-inhibition by dimerization," Proc Natl. Acad Sci. USA, 2006, 103:14337-14342.

Brigham et al., "Engineering Ralstonia eutropha for Production of Isobutanol from CO2, H2, and O2," Advanced Biofuels and Bioproducts 2013, Chapter 39, pp. 1065-1090.

Brzostowicz et al., "mRNA differential display in a microbial enrichment culture: simultaneous identification of three

(56) References Cited

OTHER PUBLICATIONS cyclohexanonemonooxygenases from three species," Applied and Environmental Microbiology, 2003, 69: 334-342.

Brzostowicz et al., "Identification of two gene clusters involved in cyclohexanone oxidation in Brevibacterium epidermidis strain HCU," Applied and Microbiological Biotechnology, 2002, 58:781-789.

Buckel et al., "Glutaconate CoA-transferase from Acidaminococcus fermentans," Eur J. Biochem, 1981, 118:315-321.

Budde et al., "Roles of Multiple Acetoacetyl Coenzyme A Reductases in Polyhydroxybutyrate Biosynthesis in Ralstonis eutropha H16," J Bacteriol. 2010, 192(20):5319-5328.

Bugg et al., "The emerging role for bacteria in lignin degradation and bio-product formation," Curr Opin Biotechnol 2011, 22(3):394-400.

Buhler et al., "Occurrence and the possible physiological role of 2-enoate reductases," FEBS Letters, 1980, 109:244-246.

Bult et al., "Complete genome sequence of the methanogenicarchaeon, Methanococcus jannaschii," Science, 1996, 273: 1058-1073.

Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.

Cantu et al., "Thioesterases: A new perspective based on their primary and tertiary structures," Protein Science 2010, 19:1281-1295.

Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from Pisum sativum," PNAS USA, 1984, 81(21):6613-7.

Chen et al., "Termites fumigate their nests with naphthalene," Nature, 1998, 392:558-559.

Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.

Clomburg et al., "Integrated engineering of Beta-oxidation reversal and omega-oxidation pathways for the synthesis of medium chain omega-functionalized carboxylic acids," Metabolic Engineering, Jan. 2015, 28:202-212.

Coon, "Omega oxygenases: nonheme-iron enzymes and P450 cytochromes," Biochemical & Biophysical Research Communications, 2005,338:378-385.

Cronan and Lin, "Synthesis of the α,ω-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.

Cryle et al., "Carbon-carbon bond cleavage by cytochrome P450BioI (CYP107H1) E1," Chemical Communications, Jan. 2004, 86-87.

Cryle, "Selectivity in a barren landscape: the P450BioI-ACP complex," Biochemical Society Transactions, Aug. 2010, 38(4):934-939.

Da Silva et al., "Glycerol: A promising and abundant carbon source for industrial microbiology," Biotechnology Advances, 2009, 27:30-39.

Daisy et al., "Naphthalene, an insect repellent, is produced by Muscodor vitigenus, a novel endophytic fungus," Microbiology, 2002, 148:3737-3741.

Dalby, "Optimizing enzyme function by directed evolution," Current Opinion in Structural Biology, 2003, 13, 500-505.

Davis et al., "Overproduction of acetyl-CoA carboxylase activity increases the rate of fatty acid biosynthesis in *Escherichia coli*," J. Biol. Chem., 2000, 275(37): 28593-28598.

Day et al., "Partial purification and properties of acyl-CoA reductase from *Clostridum butyricum*," Archives of Biochemistry and Biophysics, 1978, 190(1):322-331.

Deana et al., "Substrate specificity of a dicarboxyl-CoA: Dicarboxylic acid coenzyme. A transferase from rat liver mitochondria," Biochem Int., 1992, 26:767-773.

Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.

Dellomonaco et al., "Engineered reversal of the [beta]-oxidation cycle for the synthesis of fuels and chemicals," Nature, Jan. 2011, 476(7360):355-359.

Deshmukh and Mungre, "Purification and properties of 2-aminoadipate: 2-oxoglutarate aminotransferase from bovine kidney," Biochem J, 1989, 261(3):761-768.

Doan et al., "Functional expression of five *Arabidopsis* fatty acyl-CoA reductase genes in *Escherichia coli*," J. Plant Physiology, 2009, 166:787-796.

Dobritzsch et al., "High resolution crystal structure of pyruvate decarboxylase from Zymomonas mobilis. Implications for substrate activation in pyruvate decarboxylases," J. Biol. Chem., 1998, 273:20196-20204.

Donoghue and Trudgill, "The Metabolism of Cyclohexanol by Acinetobacter NCIB9871," Eur J Bochem., 1975, 60:1-7.

Drevland et al., "Enzymology and Evolution of the Pyruvate Pathway to 2-Oxobutyrate in Methanocaldococcus jannaschii," J. Bacteriol., Apr. 2007, 189(12):4391-4400.

Drevland et al., "Methanogen homoaconitase catalyzes both hydrolyase reactions in coenzyme B biosynthesis," J Biol Chem., Oct. 2008, 283: 28888-28896.

Egmond et al., "Fusarium solani pisi cutinase," Biochimie, Nov. 2000, 82(11):1015-1021.

Eikmanns and Buckel, "Properties of 5-hydroxyvalerate CoA-transferase from *Clostridium aminovalericum*," Biol. Chem, 1990, 371:1077-1082.

Elkins et al., "Substrate Specificity of the RND-Type Multidrug Efflux Pumps AcrB and AcrD of *Esherichia coli* is Determined Predominately by Two Large Periplasmic Looops," J Bacteriol. 2002, 184(23):6490-6499.

Elshahed et al., "Benzoate Fermentation by the Anaerobic bacterium *Syntrophus aciditrophicus* in the Absence of Hydrogen-Using Microorganisms," Applied and Environ Microbiology, 2001, 67(12):5520-5525.

Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.

Eurich et al., "Cloning and characterization of three fatty alcohol oxidase genes from Candida tropicalis strain ATCC 20336," Applied & Environment Microbiology, 2004, 70(8): 4872-4879.

Ferreira et al. "A member of the sugar transporter family, St11p is the glycerol/H= symporter in *Saccharomyces cerevisiae*," Molecular Biology of the Cell, American Society for Cell Biology, Apr. 1, 2005, 16(4):2068-2076.

Fickers et al., "Carbon and nitrogen sources modulate lipase production in the yeast *Yarrowia lipolytica*," Journal of Applied Microbiology , 2004, 96:742-9.

Fickers et al., "The lipases from Yarrowia lipolytica: Genetics, production, regulation, biochemical characterization and biotechnological applications," Biotechnology Advances, 2011, 29: 632-644.

Fonknechten et al., "Clostridium sticklandii, a specialist in amino acid degradation: revisiting its metabolism through its genome sequence," BMC Genomics, 2010, 11:1-12.

Fuchs et al., "Microbial degradation of aromatic compounds—from one strategy to four," Nat Rev Microbiol., Oct. 3, 2011;9(11):803-816, Oct. 2011.

Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.

(56) References Cited

OTHER PUBLICATIONS

Funhoff et al., "CYP153A6, a Soluble P450 Oxygenase Catalyzing Terminal-Alkane Hydroxylation," J Bacteriol. 2006, 188(14):5220-5227.
Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.
Gallus and Schink, "Anaerobic degradation of pimelate by newly isolated denitrifying bacteria," Microbiology, 1994, 140:409-416.
Gao et al: "A novel meso-diaminopimelate dehydrogenase from Symbiobacterium thermophilum: overexpression, characterization, and potential for D-amino acid synthesis," Applied and Environmental Microbiology, 2012, 78:8595-8600.
Gasmi et al.,"A molecular approach to optimize hIFN α2b expression and secretion in Yarrowia lipolytica,", Appl Microbtol Biotechnol, 2011, 89:109-119.
GenBank Accession No. AAA23536, Apr. 26, 1993, 1 page.
GenBank Accession No. AAA24664.1, Mar. 25, 1993, 1 page.
Genbank Accession No. AAA24665.1, Apr. 26, 1993, 1 page.
Genbank Accession No. AAA57874.1, Nov. 21, 2011, 2 pages.
Genbank Accession No. AAA69178.1, Jul. 1, 1995, 1 page.
Genbank Accession No. AAA92347.1, Mar. 15, 1996, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct. 23, 2009, 2 pages.
GenBank Accession No. AAB99100, Aug. 27, 1996, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
Genbank Accession No. AAG08191.1, Jan. 31, 2014, 2 pages.
Genbank Accession No. AAK73167.2, retrieved May 19, 2014, 1 page.
Genbank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
Genbank Accession No. AAT43726, retrieved May 19, 2014, 1 page.
GenBank Accession No. AAW66853.1, Feb. 12, 2005, 1 page.
Genbank Accession No. AAY39893.1, Jan. 31, 2014, 2 pages.
GenBank Accession No. AB005294, Feb. 2000, 2 pages.
Genbank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
Genbank Accession No. ABE47158.1, Jan. 26, 2014, 1 page.
Genbank Accession No. ABE47159.1, Jan. 28, 2014, 2 pages.
Genbank Accession No. ABE47160.1, Jan. 28, 2014, 1 page.
GenBank Accession No. ABI83656.1, Jan. 3, 2007, 1 page.
GenBank Accession No. ABJ63754.1, dated Mar. 2010, 1 page.
Genbank Accession No. ABK71854.1, Jan. 31, 2014, 2 pages.
Genbank Accession No. ABK75684.1, Jan. 31, 2014, 2 pages.
Genbank Accession No. ACC40567.1, Jan. 31, 2014, 2 pages.
Genbank Accession No. ACJ06772.1, Dec. 4, 2009, 1 page.
Genbank Accession No. ADG98140.1, Jan. 28, 2014, 2 pages.
GenBank Accession No. ADK19581.1, Sep. 20, 2010, 2 pages.
GenBank Accession No. AE000666.1, Jan. 5, 2006, 309 pages.
Genbank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
Genbank Accession No. BAB91331.1, retrieved May 19, 2014, 1 page.
Genbank Accession No. BAC06606, Aug. 1, 2002, 1 page.
Genbank Accession No. BAD69624, Sep. 2005, 1 page.
Genbank Accession No. BAF92773, Nov. 27, 2007, 1 page.
Genbank Accession No. BAF94304.1, retrieved May 19, 2014, 1 page.
Genbank Accession No. CAA44858.1, Apr. 28, 1992, 1 page.
Genbank Accession No. CAA81612.1, Apr. 18, 2005, 2 pages.
Genbank Accession No. CAA90836.1, Apr. 18, 2005, 2 pages.
Genbank Accession No. CAB13029.2, Nov. 20, 1997, 2 pages.
Genbank Accession No. CAC48239.1, Apr. 15, 2005, 2 page.
Genbank Accession No. CAE26094.1, Apr. 17, 2005, 2 pages.
Genbank Accession No. CAE26097.1, Apr. 17, 2005, 2 pages.
Genbank Accession No. CAH04396.1, Apr. 7, 2005, 1 page.
Genbank Accession No. CAH04397.1, Apr. 7, 2005, 2 pages.
Genbank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. D87518, Jul. 31, 1997, 2 pages.
Genbank Accession No. EFV11917.1, Sep. 9, 2013, 2 pages.
Genbank Accession No. EIV11143.1, Jun. 19, 2012, 2 pages.
Genbank Accession No. HQ418483.1, Apr. 4, 2011, 2 pages.
Genbank Accession No. JA114119.1, Apr. 19, 2011, 1 page.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 PAGES.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus sphaericus* genes controlling the bioconversion of pimlate into dethiobiotin," Gene, 1990, 87:63-70.
Gloerich et al., "Peroxisomal trans-2-enoyl-CoA reductase is involved in phytol degradation," FEBS Letters 2006, 580:2092-2096.
Gocke et al., "Comparative characterization of ThPP-dependent decarboxylases," J. Mol. Cat. B: Enzymatic, 2009, 61:30-35.

(56) References Cited

OTHER PUBLICATIONS

Gonzalez-Lopez, "Genetic control of extracellular protease synthesis in the yeast *Yarrowia lipolytica*," Genetics, 2002, 160: 417-427.
Graupner et al., "Identification of the gene encoding sulfopyruvate decarboxylase, an enzyme involved in biosynthesis of coenzyme M," J Bacterial., 2000, 182: 4862-4867.
Guerrillot et al., "Purification and Characterization of Two Aldehyde Dehydrogenases from Pseudomonas aeruginosa," Eur. J. Biochem. 1977, 81:185-192.
Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from *Lycopersicon esculentum* (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism *Alcaligenes eutrophus*," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon *Picrophilus torridus*," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of *Arabidopsis*," Plant J., 1999, 20:1-13.
Horning et al., "α-Ketoglutaric Acid," Organic Syntheses, 1955, 3: 510-512.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37: 10108-10117.
Howell et al., "Identification of enzymes homologous to isocitrate dehydrogenase that are involved in coenzyme Band leucine biosynthesis in methanoarchaea," J Bacteriol., Sep. 2000, 182: 5013-5016.
Hugler et al., "Malonyl-coenzyme A reductase from Chloroflexus aurantiacus, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US2012/069934, dated Jun. 17, 2014, 15 pages.
International Preliminary Report on Patentability in International Application No. PCT/US2012/042777, dated Jan. 10, 2013, 22 pages.
International Preliminary Report on Patentability in International Application No. PCT/US 2012/044984, dated Jan. 28, 2014, 11 pages.
International Preliminary Report on Patentability for International Application No. PCT/US2013/075058, dated Jun. 25, 2015, 11 pages.
International Preliminary Report on Patentability for International Application No. PCT/US2013/075087, dated Jun. 25, 2015, 11 pages.
International Preliminary Report on Patentability for International Application No. PCT/US2013/077445, dated Jul. 9, 2015, 11 pages.
International Preliminary Report on Patentability for International Application No. PCT/US2013/077420, dated Jul. 9, 2015, 14 pages.
International Preliminary Report on Patentability for International Application No. PCT/US2013/077419, dated Jul. 9, 2015, 13 pages.
International Preliminary Report on Patentability for International Application No. PCT/US2013/077430, dated Jul. 9, 2015, 18 pages.
International Preliminary Report on Patentability for International Application No. PCT/US2013/077413, dated Jul. 9, 2015, 13 pages.
International Preliminary Report on Patentability for International Application No. PCT/US2013/077411, dated Jul. 9, 2015, 12 pages.
International Preliminary Report on Patentability for International Application No. PCT/US2013/077423, dated Jul. 9, 2015, 14 pages.
International Search Report and Written Opinion in International Application No. PCT/US2014/052950, dated Dec. 3, 2014, 15 pages.
International Search Report and Written Opinion for International Application No. PCT/US2012/069934, dated Jan. 17, 2014, 21 pages.
International Search Report and Written Opinion in International Application No. PCT/US2012/042747, dated Jan. 14, 2013, 19 pages.
International Search Report and Written Opinion in International Application No. PCT/US 2012/042777, dated Sep. 11, 2012, 9 pages.
International Search Report and Written Opinion in International Application No. PCT/US 2012/044984, dated Dec. 17, 2013, 17 pages.
International Search Report and Written Opinion in International Application No. PCT/US 2012/071472, dated Dec. 17, 2013, 17 pages.
International Search Report and Written Opinion in International Application No. PCT/US2013/075058, dated Sep. 15, 2014, 17 pages.
International Search Report and Written Opinion in International Application No. PCT/US2013/075087, dated Aug. 4, 2014, 18 pages.
International Search Report and Written Opinion in International Application No. PCT/US2013/077411, dated Sep. 24, 2014, 18 pages.

(56) References Cited

OTHER PUBLICATIONS

International Search Report and Written Opinion in International Application No. PCT/US2013/077413, dated Jul. 22, 2014, 20 pages.
International Search Report and Written Opinion in International Application No. PCT/US2013/077419, dated Jun. 16, 2014, 19 pages.
International Search Report and Written Opinion in International Application No. PCT/US2013/077420, dated Jul. 21, 2014, 21 pages.
International Search Report and Written Opinion in International Application No. PCT/US2013/077423, dated Jul. 21, 2014, 22 pages.
International Search Report and Written Opinion in International Application No. PCT/US2013/077430, dated Nov. 10, 2014, 23 pages.
International Search Report and Written Opinion in International Application No. PCT/US2013/077445, dated Sep. 15, 2014, 17 pages.
International Search Report and Written Opinion in International Application No. PCT/US2014/053222, dated Mar. 4, 2015, 18 pages.
International Search Report and Written Opinion in International Application No. PCT/US2015/031227, dated Jul. 31, 2015, 40 pages.
International Search Report and Written Opinion in International Application No. PCT/US2015/036050, dated Aug. 14, 2015, 38 pages.
International Search Report and Written Opinion in International Application No. PCT/US2015/036057, dated Aug. 14, 2015, 74 pages.
Invitation to Pay Additional Fees in International Application No. PCT/US2013/075058, dated Jul. 7, 2014, 7 pages.
Invitation to Pay Additional Fees in International Application No. PCT/US2013/07745, dated Jul. 7, 2014, 9 pages.
Invitation to Pay Additional Fees in International Application No. PCT/US2014/053222, dated Dec. 15, 2014, 8 pages.
Invitation to Pay Fees in International Application No. PCT/US2013/075087, dated May 16, 2014, 9 pages.
Invitation to Pay Fees in International Application No. PCT/US2013/077411, dated Jul. 16, 2014, 9 pages.
Invitation to Pay Fees in International Application No. PCT/US2013/077413, dated May 12, 2014, 9 pages.
Invitation to Pay Fees in International Application No. PCT/US2013/077419, dated Apr. 16, 2014, 9 pages.
Invitation to Pay Fees in International Application No. PCT/US2013/077420, dated May 13, 2014, 9 pages.
Invitation to Pay Fees in International Application No. PCT/US2013/077423, dated May 13, 2014, 10 pages.
Invitation to Pay Fees in International Application No. PCT/US2013/077430, dated Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbiology, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.

Izumi et al., "Structure and Mechanism of HpcG, a Hydratase in the Homoprotocatechuate Degradation Pathway of *Escherichia coli*," J. Mol. Biol., 2007, 370:899-911.
Izumi et al., "The pimeloyl-CoA synthetase responsible for the first step in biotin biosynthesis by microorganisms," Agr. Biol. Chem., 1974, 38:2257-2262.
Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2—C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in Cupriavidus nectar," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.
Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from Chromobacterium violaceum DSM30191 and its potential for biocatalysis," Enzyme Microb Technol. 2007, 41:628-637.
KEGG Enzyme 1.2.99.6 (last viewed on Aug. 17, 2015).
KEGG Enzyme 3.1.2.14 (last viewed on Aug. 17, 2015).
Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 A crystal structure of the flavoprotein YqjM reveals a novel class of Old Yellow Enzymes," J. Biol. Chem., 2005, 280:27904-27913.
Kizer, "Application of Functional Genomics to Pathway Optimization for Increased Isoprenoid Production," Applied and Environmental Microbiology, 2008, 74(10)3229-3241.
Klatte et al., "Redox self-sufficient whole cell biotransformation for amination of alcohols," Bioorg & Medicinal Chem, May 2014, 22: 5578-5585.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases AlkB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.

(56) References Cited

OTHER PUBLICATIONS

Kulkarni and Kanekar, "Bioremediation of epsilon-caprolactam from nylon-6 waste water by use of Pseudomonas aeruginosa MCM B-407," Curr. Microbiol., 1998, 37:191-194.
Kung et al., "Cyclohexane carboxyl-coenzyme A (CoA) and cyclohex-1-ene-1-carboxyl-CoA dehydrogenases, two enzymes involved in the fermentation of benzoate and crotonate in Syntrophus aciditrophicus," J Bacteriol., 195(14):3193-3200, Epub May 10, 2013.
Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.
Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.
Le Dall et al., "Multiple-copy integration in the yeast *Yarrowia lipolytica*," Current Genetics, 1994 26:38-44.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Lee and Meighen, "Cysteine-286 as the site of acylation of the LUX-specific fatty acyl-CoA reductase," Biochim Biophys Acta, 1997, 1338:215-222.
Lee et al., "Metabolic Engineering of Pentose Phosphate Pathway in Ralstonia eutropha for Enhanced Biosynthesis of Poly-β-hydroxybutyrate," Biotechnology Progress, 2003, 19(5):1444-1449.
Lee et al., "Synthesis of pure meso-2,3-butanediol from crude glycerol using an engineered metabolic pathway in *Escherichia coli*," Appl Biochem Biotechnol., 2012, 166(7):1801-1813.
Li et al., "Cupriavidus necator JMP 134 rapidly reduces furfural through a Zn-dependent alcohol dehydrogenase," Biodegradation, 2011, 22:1215-1225.
Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.
Lin and Cronan, "Closing in on complete pathways of biotin biosynthesis," Molecular Biosystems, 2011, 7:1811-1821.
Lin et al., "Biotin Sythesis Begins by Hijacking the Fatty Acid Synthetic Pathway," Nature Chem Biol., Sep. 2010, 6:682-688.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin, "Biotin Synthesis in *Escherichia coli*," PhD Dissertation, University of Illinois at Urbana-Champaign, 2012, 140 pages.
Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.
Liu et al., "Two novel metal-independent long-chain alkyl alcohol dehydrogenases from Geobacillus thermodenitrificans NG80-2," Microbiology, 2009, 155:2078-2085.
Lopez-Sanchez et al., "Tetralin-Induced and ThnR-Regulated Aldehyde Dehydrogenase and β-Oxidation Genes in Sphingomonas macrogolitabida Strain TFA," Appl. Environ. Microbiol., 2010, 76(1):110-118.
Luo et al., "Production of 3-hydroxypropionic acid through propionaldehyde dehydrogenase PduP mediated biosynthetic pathway in Klebsiella pneumoniae," Bioresource Technology, 2012, 103:1-6.
Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.
Mack and Buckel, "Conversion of glutaconate CoA-transferase from Acidaminococcus fermentans into an acyl-CoA hydrolase by site-directed mutagenesis," FEBS Letters, 1997, 405:209-212.

Maeda et al., "Purification and characterization of a biodegradable plastic-degrading enzyme from Aspergillus oryzae," Applied and Environmental Biotechnology, 2005, 67: 778-788.
Mahadik et al., "Production of acidic lipase by Aspergillus niger in solid state fermentation," Process Biochemistry, 2002, 38: 715-721.
Martin and Prather, "High-titer production of monomeric hydroxyvalerates from levulinic acide Pseudomonas putida," J. Biotechnol., 2009, 139: 61-67.
Martinez et al., "Fusarium solani cutinase is a lipolytic enzyme with a catalytic serine accessible to solvent," Nature, 1992, 356:615-618.
Matsumoto et al., "A new pathway for poly(3-hydroxybutyrate) production in *Escherichia coli* and Corynebacterium glutamicum by functional expression of a new acetoacetyl-coenzyme A synthase," Biosci. Biotechnol. Biochem., 2011, 75(2):364-366.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Meijnen et al., "Improved p-hydroxybenzoate production by engineered Pseudomonas putida S12 by using a mixed-substrate feeding strategy," Appl. Microbiol. Biotechnol., 2011, 90:885-893.
Mhetras et al., "Purification and characterization of acidic lipase from Aspergillus niger NCIM 1207," Bioresource Technology, 2009, 100: 1486-1490.
Millar et al., "CUT1, an *Arabidopsis* Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.
Miyazaki et al., "Alpha-Aminoadipate aminotransferase from an extremely thermophilic bacterium, *Thermus thermophilus*," Microbiology, 2004, 150(7): 2327-2334.
Mo et al., "Connecting extracellular metabolomic measurements to intracellular flux states in yeast," BMC Systems Biology, 2009, 3(37):1-17.
Mouttaki et al., "Cyclohexane Carboxylate and Benzoate Formation from Crotonate in Sytrophus aciditrophicus," Applied and Environ Microbiology, Feb. 2007, 73(3):930-938.
Murphy et al., "Fusarium polycaprolactone depolymerase is cutinase," Appl. Environm. Microbiol., 1996, 62:456-460.
Mutti et al., "Amination of ketones by employing two new (S)-selective w-transaminases and the His-tagged w-TA from Vibrio fluvialis," Eur. J. Org. Chem, 2012, 1003-1007 (Abstract).
Naggert et al., "Cloning, sequencing, and characterization of *Escherichia coli* thioesterase II," J. Biol. Chem., 1991, 266(17):11044-11050.
Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.
Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.
Nicol et al., "Bioconversion of crude glycerol by fungi," Applied Microbiology and Biotechnology, Feb. 10, 2012, 93(5):1865-1875.
Nieder and Shapiro, "Physiological function of the Pseudomonas putida PpG6 (Pseudomonas oleovorans) alkane hydroxylase: monotelminal oxidation of alkanes and fatty acids," J. Bacteriol., 1975, 122(1):93-98.
Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.

(56) References Cited

OTHER PUBLICATIONS

Ohashi et al., "Continuous production of lactic acid from molasses by perfusion culture of Lactococcus lactis using a stirred ceramic membrane reactor," J. Bioscience and Bioengineering, 1999, 87(5):647-654.

Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.

Onakunle et al., "The formation and substrate specificity of bacterial lactonases capable of enantioselective resolution of racemic lactones," Enzyme and Microbial Technology, 1997, 21: 245-251.

Oppenheim and Dickerson, "Adipic Acid," Kirk-Othmer Encyclopedia of Chemical Technology, 2003.

Ouchi et al., "Dual roles of a conserved pair, Arg23 and Ser20, in recognition of multiple substrates in alpha-aminoadipate aminotransferase from Thermus thermoophilus," Biochem Biophys Res Commun, 2009, 388(1):21-27.

Palosaari and Rogers, "Purification and properties of the inducible coenzyme A-linked butyraldehyde dehydrogenase from Clostridium acetobutylicum," J. Bacteriol., 1988, 170(7):2971-2976.

Papanikolaou et al., "Citric acid production by Yarrowia lipolytica cultivated on olive-mill wastewater-based media," Bioresource Technol., 2008, 99(7):2419-2428.

Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.

Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.

Pérez-Pantoja et al., "Metabolic reconstruction of aromatic compounds degradation from the genome of the amazing pollutant-degrading bacterium *Cupriavidus necator* JMP134," FEMS Microbiol. Rev., 2008, 32:736-794.

Peterson et al., "The Thermal Stability of the Fusarium solani pisi Cutinase as a Function of pH," BioMed Research International, 2001, 1.2:62-69.

Pignede et al., "Autocloning and Amplification of LIP2 in Yarrowia lipolytica,"Appl. Environ. Microbiol, 2000 66:3283-3289.

Pignede et al., "Characterization of an extracellular lipase encoded by LIP2 in Yarrowia lipolytica," Journal of Bacteriology, 2000, 182: 2802-2810.

Ploux et al., "Investigation of the first step of biotin biosynthesis in Bacillus sphaericus: Purification and characterization of the pimloyl-CoA synthase, and uptake of pimelate," Biochem J., 1992, 287:685-690.

Prabhu et al., "Lactate and Acrylate Metabolism by Megasphaera elsdenii under Batch and Steady-State Conditions," Applied and Environ. Microbiology, Sep. 2012, 78(24): 8564-8570.

Prather et al., "De novo biosynthetic pathways: rational design of microbial chemical factories," Current Opinion in Biotechnology, 2008, 19:468-474.

Prybylski et al., "Third-generation feed stocks for the clean and sustainable biotechnological production of bulk chemicals: synthesis of 2-hydroxyisobutyric acid," Energy, Sustainability and Society, 2012, 2:11.

Qian et al., "Metabolic engineering of *Escherichia coli* for the production of cadaverine: a five carbon diamine," Biotechnol Bioeng, 2011, 108(1):93-103.

Qiu et al., "Crystal structure and substrate specificity of the β-ketoacyl-acyl carrier protein synthase III (FabH) from *Staphylococcus aureus*," Protein Sci, 2005, 14(8):2087-2094.

Rajashekhara et al., "Propionyl-coenzyme A synthetases of Ralstonia solanacearum and *Salmonella choleraesuis* display atypical kenetics," FEBS Letters, 2004, 556:143-147.

Ramsay et al., "Use of a Nylon Manufacturing Waste as an Industrial Feimentation Substrate," Applied and Environmental Microbiology, 1986, 52(1):152-156.

Ray et al., "Cocrystal structures of diaminopimelate decarboxylase: mechanism, evolution, and inhibition of an antibiotic resistance accessory factor," Structure, 2002, 10(11):1499-1508.

Rea et al., "Structure and Mechanism of HpcH: A Metal Ion Dependent Class II Aldolase from the Homoprotocatechuate Degradation Pathway of *Escherichia coli*," J. Mol. Biol., 2007, 373:866-876.

Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.

Rizzarelli et al., "Evidence for Selective Hydrolysis of Aliphatic Copolyesters Induced by Lipase Catalysis," Biomacromolecules, 2004, 5:433-444.

Rohdich et al., "Enoate reductases of Clostridia. Cloning, sequencing, and expression," J. Biol. Chem., 2001, 276:5779-5787.

Roje, "Vitamin B biosynthesis in plants," Phytochemistry, 2007, 68:1904-1921.

Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.

Ryu et al., "A novel synthesis of .beta.-trichlorostannyl ketones from siloxycyclopropanes and their facile dehydrostannation affording 2-methylene ketones," JOC, 1986, 51:2389-2391.

Salcher and Lingens, "Regulation of phospho-2-keto-3-deoxy-heptonate aldolase (DAHP synthase) and anthranilate synthase of Pseudomonas aureofaciens," J Gen Microbiol., 121(2):473-476, Dec. 1980.

Sambrook et al., Molecular Cloning—a Laboratory Manual, Cold Spring Harbor Laboratory Press, 2001.

Samsonova et al., "Molecular cloning and characterization of *Escherichia coli* K12 ygjG gene," BMC Microbiology, 2003, 3:2.

Sanders et al., "Characterization of the human ω-oxidation pathway for ω-hydroxy-very-long-chain fatty acids," FASEB Journal, 2008, 22(6):2064-2071.

Sanders et al., "Evidence for two enzymatic pathways for ω-oxidation of docosanoic acid in rat liver microsomes," J. Lipid Research, 2005, 46(5):1001-1008.

Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.

Scheller et al., "Generation of the Soluble and Functional Cytosolic Domain of Microsomal Cytochrome P450 52A3," J Biol Chem., 1994, 269(17):12779-12783.

Scheps et al., "Synthesis of omega-hydroxy dodecanoic acid based on an engineered CYP153A fusion construct," Microbial Biotechnology, 2013, 6:694-707.

Schirmer et al., "Microbial Biosynthesis of Alkanes," Science, 2010, 329:559-562.

Schwartz et al., "A proteomic view of the facultatively chemolithoautotrophic lifestyle of Ralstonia eutropha H16," Proteomics, 2009, 9:5132-5142.

Seedorf et al., "The genome of Clostridium kluyveri, a strict anaerobe with unique metabolic features," Proc. Natl. Acad. Sci. USA, 2008, 105(6):2128-2133.

Shapiro et al., "Remarkable Diversity in the Enzymes Catalyzing the Last Step in Synthesis of the Pimelate Moiety of Biotin," PLoSOne, Nov. 2012, 7(11):e49440, 11 pages.

Shen et al., "Driving Forces Enable High-Titer Anaerobic 1-Butanol Synthesis in *Escherichia coli*," Appl. Environ. Microbiol., 2011, 77(9):2905-2915.

Shikata et al., "A novel ADP-forming succinyl-CoA synthetase in Thermococcus kodakaraensis structurally related to the archaeal nucleoside diphosphate-forming acetyl-CoA synthetases," J. Biol. Chem, 2007, 282(37):26963-26970.

Siegert et al., "Exchanging the substrate specificities of pyruvate decarboxylase from Zymomonas mobilis and benzoylformate decarboxylase from Pseudomonas putida," Port. Eng. Des. Sel., 2005, 18:345-357.

Simon et al., "Chiral Compounds Synthesized by Biocatalytic Reductions [New Synthetic Methods (51)]," Angew Chem Ed Engl., 1985, 24:539-553.

(56) References Cited

OTHER PUBLICATIONS

Simon, "Properties and mechanistic aspects of newly found redox enzymes from anaerobes suitable for bioconversions on preparatory scale," Pure and Appl. Chem, 1992, 64:1181-1186.
Slater et al., "Multiple β-Ketothiolases Mediate Poly(β-Hydroxyalkanoate) Copolymer Synthesis in Ralstonia eutropha," J Bacteriol., 1998, 180(8):1979-1987.
Smith et al., "Complete genome sequence of Methanobacterium thermoautotrophicum deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI: A Carbon-Carbon Bond Cleaving Cytochrome P450 Involved in Biotin Biosynthesis in Bacillus Subtilis," Archives of Biochemistry and Biophysics, Dec. 2000, 384(2):351-360.
Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.
Suzuki et al., "Acetylputrescine deacetylase from Micrococcus luteus K-11," BBA—General Subjects, 1986, 882(1):140-142.
Kobayashi et al., "Antimicrobial Activity of Meropenem Against Main Bacterial Species Isolated from Patient Blood in 2006," Jpn J. Antibiot., 2007, 60(6):378-86 (with English abstract).
Suzuki et al., "GriC and GriD Constitute a Carboxylic Acid Reductase Involved in Grixazone Biosynthesis in Streptomyces griseus," J. Antibiot., 2007, 60(6):380-387.
Tomita et al., "Mechanism for multiple-substrates recognition of alpha-aminoadipate aminotransferase from Thermus theimophilus," Proteins, 2009, 75(2):348-359.
Tseng et al., "Biosynthesis of chiral 3-hydroxyvalerate from single propionate-unrelated carbon sources in metabolically engineered *E. coli*," Microbial Cell Factories, 2010, 9:96.
Uniprot Accession No. I5YEB8, Sep. 5, 2012, 1 page.
U.S. Non-Final Office Action in U.S. Appl. No. 13/524,883, dated Nov. 29, 2013, 13 pages.
U.S. Non-Final Office Action in U.S. Appl. No. 13/715,981, dated Jun. 27, 2014, 23 pages.
U.S. Notice of Allowance in U.S. Appl. No. 13/524,883, dated May 29, 2014, 7 pages.
U.S. Notice of Allowance in U.S. Appl. No. 13/715,981, dated Dec. 16, 2014, 23 pages.
U.S. Notice of Allowance in U.S. Appl. No. 13/715,981, dated Apr. 6, 2015, 10 pages.
U.S. Non-Final Office Action in U.S. Appl. No. 13/715,826, dated Jan. 30, 2015, 24 pages.
U.S. Non-Final Office Action in U.S. Appl. No. 14/106,033, dated Apr. 6, 2015, 37 pages.
U.S. Non-Final Office Action in U.S. Appl. No. 14/138,827, dated Apr. 24, 2015, 35 pages.
U.S. Non-Final Office Action in U.S. Appl. No. 14/138,971, dated Jun. 9, 2015, 44 pages.
U.S. Non-Final Office Action in U.S. Appl. No. 14/138,904, dated Jun. 9, 2015, 50 pages.
U.S. Non-Final Office Action in U.S. Appl. No. 14/490,270, dated Jul. 17, 2015, 49 pages.
U.S. Non-Final Office Action in U.S. Appl. No. 14/130,117, dated Aug. 21, 2015, 49 pages.
U.S. Notice of Allowance in U.S. Appl. No. 14/106,124, dated Dec. 24, 2014, 31 pages.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Vyazmensky et al., "Isolation and Characterization of Subunits of Acetohydroxy Acid Synthase Isozyme III and Reconstruction of the Holoenzyme," Biochemistry, 1996, 35:10339-10346.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga *Botryococcus braunii*," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White et al., "Carboxylic acid reductase: a new tungsten enzyme catalyses the reduction of non-activated carboxylic acids to aldehydes," Eur. J. Biochem., 1989, 184(1):89-96.
White, "Steps in the conversion of α-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of Streptomyces griseus: Purification and properties," Eur. J. Biochem., 1985, 146:101-106.
Zhang et al., "Expanding metabolism for biosynthesis of non-natural alcohols," Proc Natl Acad Sci U S A., 105(52):20653-20658 Epub Dec. 8, 2008.
Zhao et al., "Prediction and characterization of enzymatic activities guided by sequence similarity and genome neighborhood networks," E-Life, Jun. 2014, 3: 1-32.

(56) References Cited

OTHER PUBLICATIONS

Zhuang et al., "Divergence of function in the hot dog fold enzyme superfamily: the bacterial thioesterase YciA," Biochemistry, 2008, 47(9):2789-2796.
Zomorrodi et al., "Improving the iMM904 *S. cerevisiae* metabolic model using essentiality and synthetic lethality data," BMC Systems Biology, Dec. 2010, 4(1):1-15.
International Search Report and Written Opinion in International Application No. PCT/US2015/036074, dated Sep. 9, 2015, 14 pages.
Invitation to Pay Fees in International Application No. PCT/US2015/036086, dated Sep. 16, 2015, 7 pages.
Invitation to Pay Fees in International Application No. PCT/US2015/036092, dated Sep. 21, 2015, 8 pages.
Uniprot Accession No. P69909, Sep. 1, 2005, 1 page.
"Metabolic engineering," Wikipedia, Jun. 8, 2014 (Jun. 8, 2014), XP002744570, Retrieved from the Internet: URL://en.wikipedia.org/w/index.php?title=Metabolicengineering&oldid=612026466 [retrieved on Sep. 15, 2015] last paragraph.
Akatsuka et al., "The Serratia marcescens bioH gene encodes an esterase," Gene, Jan. 2003, 302:185-192.
Eriksen et al., "Protein Design for Pathway Engineering," Journal of Structural Biology, Apr. 2013, 185(2):234-242.
Invitation to Pay Fees in International Application No. PCT/US2015/036015, dated Oct. 2, 2015, 9 pages.
Invitation to Pay Fees in International Application No. PCT/US2015/036067, dated Sep. 18, 2015, 12 pages.
Klapa and Stephanopoulos, "Bioreaction Engineering: Modeling and Control," 2000, Springer Verlag, Heidelberg, pp. 106-124.
Moreno-Sanchez et al., "Experimental validation of metabolic pathway modeling—An illustration with glycolytic segments from Entamoeba histolytica," FEBS Journal, Jul. 2008, 275(13):3454-3469.
Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. O32472, Jun. 11, 2014, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
Chica, R. et al., "Semi-rational approaches to engineering enzyme activity: combining the benefits of directed evolution and rational design," *Curr. Opin. Biotechnol.*, 16 378-84 (2005).
Davids, T., et al. "Strategies for the discovery and engineering of enzymes for biocatalysis." *Curr. Opin. Chem. Biol.* 17(2):215-220 (2013).
Hsu, S. et al., "Addition of Autotrophic Carbon Fixation Pathways to Increase the Theoretical Heterotrophic Yield of Acetate,",The Fourth International Conference on Computational Systems Biology (ISB2010), Suzhou, China, Sep. 9-11, 2010, pp. 314-322.
Marchler-Bauer, A., et al. "CDD: specific functional annotation with the Conserved Domain Database." *Nucleic Acids Res.* 37.suppl 1: D205-D210 (2009).
Nawabi, P. et al., "Engineering *Escherichia coli* for Biodiesel Production Utilizing a Bacterial Fatty Acid Methyltransferase," *Appl. Environ. Microbiol.*, 77(22):8052-61 (2011), DOI 10.1128/AEM.05046-11.
PCT International Preliminary Report on Patentability dated Dec. 20, 2016, for International Application No. PCT/US2015/035947 (15 pages).
PCT International Preliminary Report on Patentability dated Dec. 20, 2016, for International Application No. PCT/US2015/036015 (13 pages).
PCT International Search Report dated Mar. 7, 2016, for International Application No. PCT/US2015/035947 (9 pages).
PCT International Search Report dated Dec. 8, 2015, for International Application No. PCT/US2015/036015 (9 pages).
Sen, S. et al., "Developments in Directed Evolution for Improving Enzyme Functions," *Appl. Biochem. Biotechnol.* 143:212-23 (2007), DOI 10.1007/s12010-007-8003-4.
UniProtKB Accession B2HHT4 Search Result, accessed Mar. 4, 2017 (2 pages).
UniProtKB Accession B2HN69 Search Result, accessed Mar. 4, 2017 (3 pages).
UniProtKB Accession C4ZUR7 Search Result, accessed Mar. 4, 2017 (3 pages).
UniProtKB Accession D21940 Search Result, accessed Mar. 4, 2017 (2 pages).
UniProtKB Accession M5AD45 Search Result, accessed Mar. 4, 2017 (2 pages).
UniProtKB Accession P69452 Search Result, accessed Mar. 4, 2017 (2 pages).
UniProtKB Accession P0AGG3 Search Result, accessed Mar. 4, 2017 (2 pages).
UniProtKB Accession Q59111 Search Result, accessed Mar. 4, 2017 (3 pages).
UniProtKB Accession Q73Q47 Search Result, accessed Mar. 4, 2017 (3 pages).
UniProtKB Accession Q7NWG4 Search Result, accessed Mar. 4, 2017 (3 pages).
Zhang, W. et al., "Construction of recombinant *Bacillus subtiiis* strains for efficient pimelic acid synthesis," *Electron. J. Biotechn.*, 14(6): 1-10 (2011), DOI: 10.2225/vol14-issue6-fulltext-1.
P25526 (GABD_ECOLI), UniProtKB (May 1, 2013), web.archive.org/web/20130820090622//www.uniprot.org/uniprot/P25526 (archived Aug. 20, 2013) (6 pages).
F9Y515 (F9Y515_KETVW), UniProtKB (Jun. 7, 2017), http://www.uniprot.org/uniprot/F9Y515 (3 pages).

| SEQ ID NO | Organism | GENBANK reference | Amino acid sequence |
|---|---|---|---|
| 1 | Mycobacterium marinum | ACC41782.1 | MPREIRLPESSVVVRPAPMESATYSQSSRLQAAGLSPAITLFEKAAQTVPLPDAPQPVVI ADYGVATGHNSLKPMMAAINALRRIREDRAIMVAHTDVPDNDFTALFRTLADDPDSYLH HDSASFASAVGRSFYTQILPSNTVSLGWSSWAIQWLSRIPAGAPELTDHVQVAYSKDFRA RAAYAHQAATDWQDFLAFRGRELCPGGRLVVLTMALDEHGHFGYRPMNDALVAALNDQVR DGLLRPEELRRMAIPVVARAEKDLRAPFAPRGWFEGLTIEQLDVFNAEDRFWAAFQSDGD AESFGAQWAGFARAALFPTLAAALDCGTGDPRATAFIEQLEASVADRLASQPEPMRIPLA SLVLAKRA |
| 2 | Mycobacterium smegmatis | ABK73223.1 | MPKFRVAVDPEPDDPTPKMRAPRPHAAGLNSAIALLEEAARTVPLPEAPYPIVIADYGVG TGRNSMRPIAAAIAALRGRTRPEHSVLVTHTDNADNDFTAVFRGLADNPDSYLRDTSTY PSAVGRSFYTQILPSKSVHVGWSAWAIVRVRGRMPMPVPDHVAASFSGDPQVVAAYARQAA FDWHEFVAFRGRELASGAQLVVLTAALGDDGDFGYRPLFAAVMDTLRELTADGVLRQDEL HRMSLPIVGRRANDFMAPFAPSGRFERLSISHLEVYDAEDVIYSSYQKDRDTDVFGLRWA DFCRFTFFSDLCTALDDDAARCTQFQDRLHAGIAARLSAQPEQMRIPLAQLVLERRRRSG |

FIG. 9A

| 3 | Pseudomonas putida | CAA39234.1 | MLAQLPPALQSLHLPLRLKLWDGNQFDLGPSPQVTILVKEPQLIGQLTHPSMEQLGTAFV EGKLELEGDIGEAIRVCDELSEALFTDEDEQPPERRSHDKRTDAEAISYHYDVSNAFYQL WLDQQMAYSCAYFREPDNTLDQAQQDKFDHLCRKLRLNAGDYLLDVGCGWGGLARFAARE YDAKVFGITLSKEQLKLGRQRVKAEGLTDKVDLQILDYRDLPQDGRFDKVVSVGMFEHVG HANLALYCQKLFGAVREGGLVMNHGITAKHVDGRPVGRGAGEFIDRYVFPHGELPHLSMI SASICEAGLEVVDVESLRLHYAKTLHHWSENLENQLHKAAALVPEKTLRIWRLYLAGCAY AFEKGWINLHQILAVKPYADGHHDLPWTREDMYR |
| 4 | Lactobacillus brevis | ABJ63754.1 | MAANEFSETHRVVYYEADDTGQLTLAMLINLFVLVSEDQNDALGLSTAFVQSHGVGWVVT QYHLHIDELPRTGAQVTIKTRATAYNRYFAYREYWLLDDAGQVLAYGEGIWVTMSYATRK ITTIPAEVMAPYHSEEQTRLPRLPRPDHFDEAVNQTLKPYTVRYFDIDGNGHVNNAHYFD WMLDVLPATFLRAHHPTDVKIRFENEVQYGHQVTSELSQAAALTTQHMIKVGDLTAVKAT IQWDNR |

FIG. 9B

| 5 | Lactobacillus plantarum | CCC78182.1 | MATLGANASLYSEQHRITYYECDRTGRATLTTLIDIAVLASEDQSDALGLITEMVQSHGV GWVVTQYAIDITRMPRQDEVVTIAVRGSAYNPYFAYREFWIRDADGQQLAYITSIWVMMS QTTRRIVKILPELVAPYQSEVVKRIIPRLPRPISFEATDTTITKPYHVRFFDIDPNRHVNN AHYFDWLVDTLPATFLLQHDLVHVDVRYENEVKYGQTVTAHANILPSEVADQVTTSHLIE VDDEKCCEVTIQWRTLPEPIQ |
| --- | --- | --- | --- |
| 6 | Escherichia coli | AAC76437.1 | MNNIWWQTKGQGNVHLVLLHGWGLNAEVWRCIDEELSSHFTLHLVDLPGFGRSRGFGALS LADMAEAVLQQAPDKAIWLGWSLGGLVASQIALTHPERVQALVTVASSPCFSARDEWPGI KPDVLAGFQQQLSDDFQRTVERFLALQTMGTETARQDARALKKTVLALPMAPEVDVLNGGL EILKTVDLRQPLQNVSMPFLRLYGYLDGLVPRKVVPMLDKLWPHSESYIFAKAAHAPFIS HPAEFCHLLVALKQRV |

FIG. 9C

| | | | |
|---|---|---|---|
| 7 | *Mycobacterium marinum* | ACC40567.1 | MSPITREERLERRIQDLYANDPQFAAAKPATAITAAIERPGLPLPQIIETVMTGYADRPA<br>LAQRSVEFVTDAGTGHTTLRLLPHFETISYGELWDRISALADVLSTEQTVKPGDRVCLLG<br>FNSVDYATIDMTLARLGAVAVPLQTSAAITQLQPIVAETQPTMIAASVDALADATELALS<br>GQTATRVLVFDHHRQVDAHRAAVESARERLAGSAVVETLAEAIARGDVPRGASAGSAPGT<br>DVSDDSLALLIYTSGSTGAPKGAMYPRRNVATFWRKRTWFEGGYEPSITLNFMPMSHVMG<br>RQILYGTLCNGGTAYFVAKSDLSTLFEDLALVRPTELTFVPRVWDMVFDEFQSEVDRRLV<br>DGADRVALEAQVKAEIRNDVLGGRYTSALTGSAPISDEMKAWVEELLDMHLVEGYGSTEA<br>GMILIDGAIRRPAVLDYKLVDVPDLGYFLTDRPHPRGELLVKTDSLFPGYYQRAEVTADV<br>FDADGFYRTGDIMAEVGPEQFVYLDRRNNVLKLSQGEFVTVSKLEAVFGDSPLVRQIYIY<br>GNSARAYLLAVIVPTQEALDAVPVEELKARLGDSLQEVAKAAGLQSYEIPRDFIIETTPW<br>TLENGLLTGIRKLARPQLKKHYGELLEQIYTDLAHGQADELRSLRQSGADAPVLVTVCRA<br>AAALLGGSASDVQPDAHFTDLGGDSLSALSFTNLLHEIFDIEVPVGVIVSPANDLQALAD<br>YVEAARKPGSSRPTFASVHGASNGQVTEVHAGDLSLDKFIDAATLAEAPRLPAANTQVRT<br>VLLTGATGFLGRYLALEWLERMDLVDGKLICLVRAKSDTEARARLDKTFDSGDPELLAHY<br>RALAGDHLEVLAGDKGEADLGLDRQTWQRLADTVDLIVDPAALVNHVLPYSQLFGPNALG<br>TAELLRLALTSKIKPYSYTSTIGVADQIPPSAFTEDADIRVISATRAVDDSYANGYSNSK<br>WAGEVLLREAHDLCGLPVAVFRCDMILADTTWAGQLNVPDMFTRMILSLAATGIAPGSFY<br>ELAADGARQRAHYDGLPVEFIAEAISTLGAQSQDGFHTYHVMNPYDDGIGLDEFVDWLNE<br>SGCPIQRIADYGDWLQRFETALRALPDRQRHSSLLPLLHNYRQPERPVRGSIAPTDRFRA<br>AVQEAKIGPDKDIPHVGAPIIVKYVSDLRLLGLL |

FIG. 9D

| 8 | Mycobacterium smegmatis | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALARAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDVKLIDVPELGYFSTDKPYPRGELLVRSQTLTPGYY KRPEVTASVFDRDGYYHTGDVMAETAPDHLVYVDRRNNVLKLAQGEFVAVANLEAVFSGA ALVRQJFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAAATILGTGSEVASDAHFTDLGGDSLSALTLSNLLSDFFGF

| 9 | Segniliparus rugosus | EFV11917.1 | MGDGEERAKRFFQRIGELSATDPQFAAAAPDPAVVEAVSDPSLSFTRYLDTLMRGYAERP
ALAHRVGAGYETISYGELWARVGAIAAAWQADGLAPGDFVATVGFTSPDYVAVDLAAARS
GLVSVPLQAGASLAQLVGILEETEPKVLAASASSLEGAVACALAAPSVQRLVVFDLRGPD
ASESAADERRGALADAEEQLARAGRAVVVETLADLAARGEALPEAPLFEPAEGEDPLALL
IYTSGSTGAPKGAMYSQRLVSQLWGRTPVVPGMPNISLHYMPLSHSYGRAVLAGALSAGG
TAHFTANSDLSTLFEDIALARPTFLALVPRVCEMLFQESQRGQDVAELRERVLGGRLLVA
VCGSAPLSPEMRAFMEEVLGFPLLDGYGSTEALGVMRNGIIQRPPVIDYKLVDVPELGYR
TTDKPYPRGELCIRSTSLISGYYKRPEITAEVFDAQGYYKTGDVMAEIAPDHLVYVDRSK
NVLKLSQGEFVAVAKLEAAYGTSPYVKQIFVYGNSERSFLLAVVPNAEVLGARDQEEAK
PLIAASLQKIAKEAGLQSYEVPROFLIETEPFTTQNGLLSEVGKLLRPKLKARYGEALEA
RYDEIAHGQADELRALRDGAGQRPVVETVVRAAVAISGSEGAEVGPEANFADLGGDSLSA
LSLANLLHDVFEVEVPVRIIIGPTASLAGIAKHIEAERAGASAPTAASVHGAGATRIRAS
ELTLEKFLPEDILAAAKGLPAADQVRTVLLTGANGWIGRFLALEQLERLARSGQDGGKLI
CLVRGKDAAAARRRIEETILGTDPALAARFAELAEGRLEVVPGDVGEPKFGLDDAAWDRLA
EEVDVIVHPAALVNHVLPYHQLFGPNVVGTAEIIRLAITAKRKPVTYLSTVAVAAGVEPS
SFEEDGDIRAVVPERPLGDGYANGYGNSKWAGEVLLREAHELVGLPVAVFRSDMILAHTR
YTGQLINVPDQFTRLVLSLLATGIAPKSFYQQGAAGERQRAHYDGIPVDFTAEAITTLGAE
PSWFDGGAGFRSFDVFNPHHDGVGLDEFVDWLIEAGHPISRIDDHKEWFARFETAVRGLP
EAQRQHSLLPLLRAYSFPHPPVDGSVYPTGKFQGAVKAAQVGSDHDVPHLGKALIVKYAD
DLKALGLL |

FIG. 9F

| 10 | Mycobacterium smegmatis | ABK75684.1 | MTIETREDRFNRRIDHLFETDPQFAAARPDEAISAAAADPELRLPAAVKQILAGYADRPA LGKRAVEFVTDEEGRTTAKLLPRFDTITYRQLAGRIQAVTNAWHNHPVNAGDRVAILGFT SVDYTTIDJALLELGAVSVPLQTSAPVAQLQPIVAETEPKVIASSVDFLADAVALVESGP APSRLVVFDYSHEVDDQREAFEAAKGKLAGTGVVVETITDALDRGRSLADAPLYVPDEAD PLTLLIJYTSGSTGTPKGAMYPESKTATMWQAGSKARWDETLGVRAPSITLNFMPMSHVMGR GILCSTLASGGTAYFAARSDLSTFLEDLALVRPTQLNFVPRIWDMLFQEYQSRLDNRRAE GSEDRAEAAVLEEVRTQLLGGRFVSALTGSAPISAEMKSWVEDLLDMHLLEGYGSTEAGA VFIDGQJQRPPVIDYKLVDPDLGYFATDRPYPRGELLVKSEQMFPGYYKRPEITAEMFD EDGYYRTGDIVAELGPDHLEYLDRRNNVLKLSQGEFVTVSKLEAVFGDSPLVRQIYVYGN SARSYLLAVVVPTEEALSRWDGDELKSRISDSLQDAARAAGLQSYEIPRDFLVETTPFTL ENGILLTGIRKLARPKLKAHYGERLEQLYTDLAEGQANELRELRRNGADRPVVETVSRAAV ALLGASVTDLRSDAHFTDLGGDSLSALSFSNLLHEIFDVDPVGVIVSPATDLAGVAAYI EGELRGSKRPTYASVHGRDATEVRARDLALGKFIDAKTLSAAPGLPRSGTEIRTVLLTGA TGFLGRYLALEWLERMDLVDGKVICLVRARSDDEARARLDATFDTGDATLLEHYRALAAD HLEVIAGDKGEADLGLDHDTWQRLADTVDLIVDPAALVNHVLPYSQMFGPNALGTAELIR IALTTTIKPYVVYVSTIGVGQGISPEAFVEDADIREISATRRVDDSYANGYGNSKWAGEVL LREAHDWCGLPVSVFRCDMILADTTYSGQJ.NLPDMFTRIMLSLVATGIAPGSFYELDADG NRQRAHYDGLPVEFIAEAISTIGSQVTDGFETFHVMNPYDDGIGLDEYVDWLIEAGYPVH RVDDYATWLSRFETALRALPERQRQASLLPLLHNYQQPSPPVCGAMAPTDRFRAAVQDAK IGPDKDIPHVTADVIVKYISNLQMLGLL |

FIG. 9G

| | | | |
|---|---|---|---|
| *11* | *Mycobacterium massiliense* | EIV11143.1 | MTNETNPQQEQLSRRIESLRESDPQFRAAQPDPAVAEQVLRPGLHLSEAIAALMTGYAER<br>PALGERARELVIDQDGRTTLRLLPRFDTTTYGELWSRTTSVAAAWHHDATHPVKAGDLVA<br>TLGFTSIDYTVLDLAIMILGGVAVPLQTSAPASQWTTILAEAEPNTLAVSIELIGAAMES<br>VRATPSIKQVVVFDYTPEVDDQREAFEAASTQLAGTGIALETLDAVIARGAALPAAPLYA<br>PSAGDDPLALLIYTSGSTGAPKGAMHSENIVRRWWIREDVMAGTENLPMIGLNFMPMSHI<br>MGRGTLTSTLSTGGTGYFAASSDMSTLFEDMELIRPTALALVPRVCDMVFQRFQTEVDRR<br>LASGDTASAEAVAAEVKADIRDNLFGGRVSAVMVGSAPLSEELGEFIESCFELNLTDGYG<br>STEAGMVFRDGIVQRPPVIDYKLVDVPELGYFSTDKPHPRGELLLKTDGMFLGYYKRPEV<br>TASVFDADGFYMTGDIVAELAHDNIEIIDRRNNVLKLSQGEFVAVATLEAEYANSPVVHQ<br>IYVYGSSERSYLLAVVVPTPEAVAAAKGDAAALKTTIADSLQDIAKEIQLQSYEVPRDFI<br>IEPQPFTQGNGLLTGIAKLARPNLKAHYGPRLEQMYAEIAEQQAAELRALHGVDPDKPAL<br>ETVLKAAQALLGVSSAELAADAHFTDLGGDSLSALSFSDLLRDIFAVEVPVGVIVSAAND<br>LGGVAKFVDEQRHSGGTRPTAETVHGAGHTEIRAADLTLDKFIDEATLHAAPSLPKAAGI<br>PHTVLLTGSNGYLGHYLALEWLERLDKTDGKLIVIVRGKNAEAAYGRLEEAFDTGDTELL<br>AHFRSLADKHLEVLAGDIGDPNLGLDADTWQRLADTVDVIVHPAALVNHVLPYNQLFGPN<br>VVGTAEIIKLAITTKIKPVTYLSTVAVAAYVDPTTFDEESDIRLISAVRPIDDGYANGYG<br>NAKWAGEVLLREAHDLCGLPVAVFRSDMILAHSRYTGQLNVPDQFTRLILSLIATGIAPG<br>SFYQAQTTGERPLAHYDGLPGDFTAEAITTLGTQVPEGSEGFVTYDCVNPHADGISLDNF<br>VDWLIEAGYPIARIDNYTEWFTRFDTAIRGLSEKQKQHSLLPLLHAFEQPSAAENHGVVP<br>AKRFQHAVQAAGIGPVGQDGTTDIPHLSRRLIVKYAKDLEQLGLL |

FIG. 9H

| 12 | *Segniliparus roturidus* | ADG98140.1 | MTQSHTQGPQASAAHSRLARRAEELLATDPQAAATLPDPEVVRQATRPGLRLAERVDAIL<br>SGYADRPALGQRSFQTVKDPITGRSSVELLPTFDTITYRELRERATAIASDLAHHPQAPA<br>KPGDFLASIGFISVDYVAIDIAGVFAGLTAVPLQTGATLATLTAITAETAPTLFAASIEH<br>LPTAVDAVLATPSVRRLLVFDYRAGSDEDREAVEAAKRKIADAGSSVLVDVLDEVIARGK<br>SAPKAPLPPATDAGDDSLSLLIYTSGSTGTPKGAMYPERNVAHFWGGVWAAAFDEDAAPP<br>VPAINITFLPLSHVASRLSLMPTLARGGLMHFVAKSDLSTLFEDLKLARPTNLFLVPRVV<br>EMLYQHYQSELDRRGVQDGTREAEAVKDDLRTGLLGGRILTAGFGSAPLSAELAGHESL<br>LQJHLVDGYGSTEAGPVWRDGYLVKPPVTDYKLIDVPELGYFSTDSPHPRGELAIKTQTI<br>LPGYYKRPETTAEVFDEDGFYLTGDVVAQIGPEQFAYVORRKNVLKLSQGEFVTLAKLEA<br>AYSSPLVRQLFVYGSSERSYLLAVIVPTPDALKKFGVGEAAKAALGESLQKIARDEGLQ<br>SYEVPRDFHIETDPFTVENGLLSDARKSLRPKLKEHYGERLEAMYKELADGQANELRDIR<br>RGVQQRPTLETVRRAAAAMLGASAAEIKPDAHFTDLGGDSLSALTFSNFLLHDLFEVDPVV<br>GVIVSAANTLGSVAEHIDAQLAGGRARPTFATVHGKGSTTIKASDLTLDKFIDEQTLEAA<br>KHLPKPADPPRTVLLTGANGWLGRFLALEWLERLAPAGGKLITIVRGKDAACQAKARLDAA<br>YESGDPKLAGHYQDLAATTLEVLAGDFSEPRLGLDEATWNRLADEVDFISHPGALVNHVL<br>PYNCQLFGPNVAGVAEIIKLAITTRIKPVTYLSTVAVAAGVEPSALDEDGDIRTVSAERSV<br>DEGYANGYGNSKWGGEVLLREAHDRTGLPVRVFRSDMILAHQKYTGQVNATDQFTRLVQS<br>LLATGLAPKSFYELDAQGNRQRAHYDGIPVDFTAESITTLGGDGLEGYRSYNVFNPHRDG<br>VGLDEFVDWLIEAGHPITRIDDYDQWLSRFETSLRGLPESKRQASVLPLLHAFARPGPAV<br>DGSPFRNTVFRTDVQKAKIGAEHDIPHLGKALVLKYADDIKQLGLL |

FIG. 9I

| 13 | Chromobacterium violaceum | AAQ59697.1 | MQKQRTTSQWRELDAAHHLHPFTDTASLNQAGARVMTRGEGVYLWDSEGNKIIDGMAGLW CVNVGYGRKDFAEAARRQMEELPFYNTFFKTTHPAVVELSSLLAEVTPAGFDRVFYTNSG SESVDTMIRMVRRYWDVQGKPEKTLIGRWNGYHGSTIGGASLGGMKYMHEQGDLPIPGM AHIEQPWWYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |
| 14 | Pseudomonas aeruginosa | AAG08191.1 | MNARLHATSPLGDADLVRADQAHYMHGYHVFDDHRVNGSLNIAAGDGAYIYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVITRINAYHGSTFLGMSLGGKSADRPAEF DFLDERIHHLACPYYYRAPEGLGEAEFLDGLVDEFERKILELGADRVGAFISEPVFGSGG VIVPPAGYHRRMWELCQRYDVLYISDEVVTSFGRLGHFFASQAVFGVQPDIILTAKGLTS GYQPLGACIFSRRIWEVIAEPDKGRCFSHGFTYSGHPVACAAALKNIEHEREGLLAHAD EVGRYFEERLQSLRDLPIVGDVRGMRFMACVEFVADKASKALFPESLNIGEWVHLRAQKR GLLVRPIVHLNVMSPPILTREQVDTVVRVLRESIEETVEDLVRAGHR |
| 15 | Pseudomonas syringae | AAY39893.1 | MSANNPQTLEWQALSSEHHLAPFSDYKQLKEKGPRIITRAEGVYLWDSEGNKILDGMSGL WCVAIGYGREELADAASKQMRELPYYNLFFQTAHPPVLELAKAISDIAPEGMNHVFFTGS GSEGNDTMLRMVRHYWALKGQPNKKTIISRVNGYHGSTVAGASLGGMTYMHEQGDLPIPG VVHPQPYWFGEGGDMTPDEFGIWAAEQLEKKILELGVENVGAFIAEPIQGAGGVIVPPD SYWPKIKEILSRYDILFAADEVICGFGRTSEWFGSDFYGLRPDMMTIAKGLTSGYVPMGG LIVRDEIVAVLNEGGDFNHGFTYSGHPVAAAVALENIRILREEKIVERVRSETAPYLQKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |

FIG. 9J

| 16 | Rhodobacter sphaeroides | ABA81135.1 | MTRNDATNAAGAVGAAMRDHILLPAQEMAKLGKSAQPVLTHAEGIYVHTEDGRRLIDGPA GMWCAQVGYGRREIVDAMAHQAMVLPYASPWYMATSPAARLAEKIATLTPGDLNRIFTT GGSTAVDSALRFSEFYNNVLGRPQKKRIIVRYDGYHGSTALTAACTGRTGNWPNFDIAQD RISFLSSPNPRHAGNRSQEAFLDDLVQEFEDRIESLGPDTIAAFLAEPILASGGVIIPPA GYHARFKAICEKHDILYISDEVTGFGRCGEWFASEKVFGVVPDIITFAKGVTSGYVPLG GLAISEAVLARISGENAKGSWFTNGYTYSNQPVACAAALANIELMEREGIVDQAREMADY FAAALASLRDLPGVAETRSVGLVGCVQCLLDPTRADGTAEDKAFTLKIDERCFELGLIVR PLGDLCVISPPLIISRAQIDEMVAIMRQAITEVSAAHGLTAKEPAAV |
| 17 | Escherichia coli | AAA57874.1 | MNRLPSSASALACSAHALNLIEKRTLDHEEMKALNREVIEYFKEHVNPGFLEYRKSVTAG GDYGAVEWQAGSLNTLVDTQGQEFIDCLGGFGIFNVGHRNPVVVSAVQNQLAKQPLHSQE LLDPLRAMLAKTLAALTPGKLIKYSFFCNSGTESVEAALKLAKAYQSPRGKFTFIATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDILCLAK ALGGGVMPIGATIATEEVFSVLFDNPFLHTTTFGGNPLACAAALATINVLLEQNLPAQAE QKGDMLLDGFRQLAREYPDLVQEARGKGMLMAIEFVDNEIGYNFASEMFRQRVLVAGTLN NAKTIRIEPPLTLTIEQCELVIKAARKALAAMRVSVEFA |
| 18 | Vibrio Fluvialis | AEA39183.1 | MNKPQSWEARAETYSLYGFTDMPSLHQRGTVVVTHGEGPYIVDVNGRRYLDANSGLWNMV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQFVARLARELEETIQREGADTIAGFFAEPVMGAGGVIPPAKGYFQ AILPLHRKYDIPVISDEVICGFGRTGNTWGCVTYDFTPDAIISKNLTAGFFPNMGAVILG PELSKRLETAIEAIEEFPHGFTASGHPVGCAIALKAIDVVMNEGLAENVRRLAPRFEERL KHIAERPNIGEYRGIGFMWALEAVKDKASKTPFDGNLSVSERIANTCTDLGLICRPLGQS VVLCPPFILTEAQMDEMFDKLEKALDKVFAEVA |

FIG. 9K

| 19 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEIAK RFFSKTEYSDLLAKDKDEQTDYFYHLWSMKESFIKQEGKGLSLPLDSFSVRLHQDGQVSI ELPDSHSPCYIKTYEVDPGYKMAVCAAHPDFPEDITMVSYEELL |
|---|---|---|---|
| 20 | Nocardia sp. NRRL 5646 | ABI83656.1 | MIETILPAGVESAELLEYPEDLKAHPAEEHLIAKSVEKRRDFIGARHCARLALAELGEP PVAIGKGERGAPIWPRGVVGSLTHCDGYRAAAVAHKMRFRSIGIDAEPHATLPEGVLDSV SLPPEREWLKTTDSALHLDRLLFCAKEATYKAWWPLTARWLGFEEAHITFEIEDGSADSG NGTFHSELLVPGQTNDGGTPLLSFDGRWLIADGFILTAJAYA |
| 21 | Escherichia coli | AAA24665.1 | MSQALKNLLTLLNLEKIEEGLFRGQSEDLGLRQVFGGQVVGQALYAAKETVPEERLVHSF HSYFLRPGDSKKPIIYDVETLRDGNSFSARRVAAIQNGKPIFYMTASFQAPEAGFEHQKT MPSAPAPDGLPSETQIAQSLAHILPPVLKDKFICDRPLEVRPVEFHNPLKGHVAEPHRQV WIRANGSVPDDLRVHQYLLGYASDLNFLPVALQPHGIGFLEPGIQIATIDHSMWFHRPFN LNEWLLYSVESTSASSARGFVRGEFYTQDGVLVASTVQEGVMRNHN |

FIG. 9L

| 22 | Escherichia coli | CAA50321.1 | MKKVWLNRYPADVPTEINPDRYQSLVDMFEQSVARYADQPAFVNMGEVMTFRKLEERSRA FAAYLQQGLGLKKGDRVALMMPNLLQYPVALFGILRAGMIVVNVNPLYTPRELEHQLNDS GASAIVSNFAHTLEKVVDKTAVQHVILTRMGDQLSTAKGTVVNFVVKYIKRLVPKYHL PDAISFRSALHNGYRMQYVKPELVPEDLAFLQYTGGTTGVAKGAMLTHRNMLANLEQVNA TYGPLLHPGKELVVTALPLYHIFALTINCLLFIELGGQNLLITNPRDIPGLVKELAKYPF TAITGVNTLFNALLNNKEFQQLDFSSLHLSAGGGMPVQQVVAERWVKLTGQYLLEGYGLT ECAPLVSVNPYDIDYHSGSIGLPVPSTEAKLVDDDNEVPPGQPGELCVKGPQVMLGYWQ RPDATDEIIKNGWLHTGDIAVMDEEGFLRIVDRKKDMILVSGFNVVPNEIEDVVMQHPGV QEVAAVGVPSGSSGEAVKIFVVKKDPSLTEESLVTFCRRQLTGYKVPKLVEFRDELPKSN VGKILRRELRDEARGKVDNKA |

FIG. 9M

| 23 | *Cupriavidus necator* | CAJ95550.1 | MHPHIHAQRTPEKPAVIMGGSGAVVTYRELDERSNQVAHLFRSQGLQPGDRVAFMVENHP RLFELCWGAQRSGIVVVCLSTRLNVADAAHINDSGARLLVTHAQAEVAAALAGQTPAL RGRLMLDGTMPGYDAYETALARCPATRIDDEVTGGDMLYSSGTTGRPKGVYAPPSSPNID DPTTLTSLCQRLYGFDAETRYLSPAPLYHAAPLRYNMTVQALGGTAVVMEHFDAEHYLQL VQQHRITHTQLVPTMFSRMLKLPEAQRQAYDVSSLRVAIHAAAPCPVQVKEAMIAWWGPV IWEYYAGTEGNGTVVVSTPEWLERKGTVGRAMVGKLRICGPDGALLPPGESGTTYFAEGR DFSYHNDEAKTAESRHPQQPDWSTIGDVGYGYVDADGYLYLTDRKANMIISGGVNIYPQEAE NLLMTHPKVMDVAVIGVPNEDFGEEVKAVVQPVDMSQAGPELAAELIAFCRANLSAIKCP RSVDFASELPRLPTGKLLKRLLRDRYWGGHANKLV |
| 24 | *Acidaminococcus fermentans* | CAA57199.1 | MSKVMTLKDAIAKYVHSGDHIALGGFTTDRKPYAAVFEILRQGITDLTGLGGAAGGDWDM LIGNGRVKAYINCYTANSGVTNVSRRFRKWFEAGKLTMEDYSQDVIYMMWHAAALGLPFL PVTLMQGSGLTDEWGISKEVRKTLDKVPDDKFKYIDNPFKPGEKVVAVPVPQVDVAIHA QQASPDGTVRIWGGKFQDVDIAEAAKYTIVTCEEIISDEEIRRDPTKNDIPGMCVDAVVL APYGAHPSQCYGLYDYDNPFLKVYDKVSKTQEDFDAFCKEWVFDLKDHDEYLNKLGATRL INLKVVPGLGYHIDMTKEDK |

FIG. 9N

| 25 | Acidaminococcus fermentans | CAA57200.1 | MADYTNYTNKEMQAVTIAKQIKNGQVVTVGTGLPLIGASVAKRVYAPDCHIVESGLMDC SPVEVPRSVGDLRFMAHCGCIWPNVRFVGFEINEYLHKANRLIAFIGGAQIDPYGNVNST SIGDYHHPKTRFTGSGGANGIATYSNTIIMMQHEKRRFMNKIDYVTSPGWIDGPGGRERL GLPGDVGPQLVVTDKGILKFDEKTKRMYLAAYYPTSSPEDVLENTGFDLDVSKAVELEAP DPAVIKLIREEIDPGQAFIQVPTEAK |
|---|---|---|---|
| 26 | Treponema denticola | AAS11092.1 | MIVKPMAVRNNICLNAHPQGCKKGVEDQIEYTKKRITAEVKAGAKAPKNVLILGCSNGYGL ASRITAAFGYGAATIGVSFEKAGSETKYGTPGWYNNLAFDEAAKREGLYSVTIDGDAFSD EIKAQVIEEAKKKGIKFDLIVYSLASPVRTDPDTGIMHKSVLKPFGKTFTGKTVDPFTGE LKEISAEPANDEEAAATVKVMGGEDWERWIKQLSKEGLLEEGCITLAYSYIGPEATQALY RKGTIGKAKEHLEATAHRLNKENPSIRAFVSVNKGLVTRASAVIPVLYLASLFKVMKE KGNHEGCIEQITRLYAERLYRKDGTIPVDEENRIRIDDWELEEDVQKAVSALMEKVTGEN AESLTDLAGYRHDFLASNGFDVEGINYEAEVERFDRI |

FIG. 9O

| 27 | Euglena gracilis | AAW66853.1 | MSCPASPSAAVVSAGALCLCVATVLLATGSNPTALSTASTRSPTSLVRGVDRGLMRPTTA<br>AALTTMREVPQMAEGFSGEATSAWAAAGPQWAAPLVAAASSALALWWWAARRSVRRPLAA<br>LAELPTAVTHLAPPMAMFTTAKVIQPKIRGFICTTHPIGCEKRVQEEIAYARAHPPTS<br>PGPKRVLVIGCSTGYGLSTRITAAFGYQAATLGVFLAGPPTKGRPAAAGWYNTVAFEKAA<br>LEAGLYARSLNGDAFDSTTKARTVEAIKRDLGTVDLVVYSIAAPKRTDPATGVLHKACLK<br>PIGATYTNRTVNTDKAEVTDVSIEPASPEEIADTVKVMGGEDWELWIQAISEAGVLAEGA<br>KTVAYSYIGPEMTWPVYWSGTIGEAKKDVEKAAKRITQQYGCPAYPVVAKALVTQASSAI<br>PVVPLYICLLYRVMKEKGTHEGCIEQMVRLLTTKLYPENGAPIVDEAGRVRDDWEMAED<br>VQQAVKDLWSQVSTANLKDISDFAGYQTEFLRLFGFGIDGVDYDQPVDVEADLPSAAQQ |
| 28 | Escherichia coli | AAB60068.1 | MSTTHNVPQGDLVLRTLAMPADTNANGDIFGGWLMSQMDIGGAILAKEIAHGRVVTVRVE<br>GMTFLRPVAVGDVVCCYARCVQKGTTSVSINIEVWVKKVASEPIGQRYKATEALFKYVAV<br>DPEGKPRALPVE |

FIG. 9P

| Sample ID | Analyte | Mwt [g/mol] | Peak Retention Time [min] | Peak Area @ 260nm [mAu] | Observed Mass (m/z) Negative mode (M-H) | Positive mode (M+H) | Comments |
|---|---|---|---|---|---|---|---|
| Reference Standard | adipyl-CoA methyl ester | 909 | 5.835 | 4755 | 908 | 910 | |
| Biotransformation at 1 [h] time point #1 | adipyl-CoA methyl ester | 909 | nd | nd | nd | nd | No substrate detected after 1 [h] |
| | adipyl-CoA | 896 | 5.172 | 2023.3 | 894 | 896 | |
| Biotransformation at 1 [h] time point #2 | adipyl-CoA methyl ester | 909 | nd | nd | nd | nd | No substrate detected after 1 [h] |
| | adipyl-CoA | 896 | 5.18 | 1499.7 | 894 | 896 | |
| Biotransformation at 1 [h] time point #3 | adipyl-CoA methyl ester | 909 | nd | nd | nd | nd | No substrate detected after 1 [h] |
| | adipyl-CoA | 896 | 5.17 | 2095.4 | 894 | 896 | |
| Substrate only control (no enzyme) at 1 [h] time point | adipyl-CoA methyl ester | 909 | 5.893 | 1511.2 | n/a | n/a | Trace amount of product detected. |
| | adipyl-CoA | 896 | 5.214 | 22.3 | 894 | 896 | |

FIG. 20

SEQUENCE LISTING

<160> NUMBER OF SEQ ID NOS: 28

<210> SEQ ID NO 1
<211> LENGTH: 368
<212> TYPE: PRT
<213> ORGANISM: Mycobacterium marinum

<400> SEQUENCE: 1

Met Pro Arg Glu Ile Arg Leu Pro Glu Ser Ser Val Val Arg Pro
1               5                   10                  15

Ala Pro Met Glu Ser Ala Thr Tyr Ser Gln Ser Ser Arg Leu Gln Ala
            20                  25                  30

Ala Gly Leu Ser Pro Ala Ile Thr Leu Phe Glu Lys Ala Ala Gln Thr
        35                  40                  45

Val Pro Leu Pro Asp Ala Pro Gln Pro Val Val Ile Ala Asp Tyr Gly
    50                  55                  60

Val Ala Thr Gly His Asn Ser Leu Lys Pro Met Met Ala Ala Ile Asn
65                  70                  75                  80

Ala Leu Arg Arg Arg Ile Arg Glu Asp Arg Ala Ile Met Val Ala His
                85                  90                  95

Thr Asp Val Pro Asp Asn Asp Phe Thr Ala Leu Phe Arg Thr Leu Ala
            100                 105                 110

Asp Asp Pro Asp Ser Tyr Leu His His Asp Ser Ala Ser Phe Ala Ser
        115                 120                 125

Ala Val Gly Arg Ser Phe Tyr Thr Gln Ile Leu Pro Ser Asn Thr Val
    130                 135                 140

Ser Leu Gly Trp Ser Ser Trp Ala Ile Gln Trp Leu Ser Arg Ile Pro
145                 150                 155                 160

Ala Gly Ala Pro Glu Leu Thr Asp His Val Gln Val Ala Tyr Ser Lys
                165                 170                 175

Asp Glu Arg Ala Arg Ala Ala Tyr Ala His Gln Ala Ala Thr Asp Trp
            180                 185                 190

Gln Asp Phe Leu Ala Phe Arg Gly Arg Glu Leu Cys Pro Gly Gly Arg
        195                 200                 205

Leu Val Val Leu Thr Met Ala Leu Asp Glu His Gly His Phe Gly Tyr
    210                 215                 220

Arg Pro Met Asn Asp Ala Leu Val Ala Ala Leu Asn Asp Gln Val Arg
225                 230                 235                 240

Asp Gly Leu Leu Arg Pro Glu Glu Leu Arg Arg Met Ala Ile Pro Val
                245                 250                 255

Val Ala Arg Ala Glu Lys Asp Leu Arg Ala Pro Phe Ala Pro Arg Gly
            260                 265                 270

Trp Phe Glu Gly Leu Thr Ile Glu Gln Leu Asp Val Phe Asn Ala Glu
        275                 280                 285

Asp Arg Phe Trp Ala Ala Phe Gln Ser Asp Gly Asp Ala Glu Ser Phe
    290                 295                 300

```
Gly Ala Gln Trp Ala Gly Phe Ala Arg Ala Ala Leu Phe Pro Thr Leu
305                 310                 315                 320

Ala Ala Ala Leu Asp Cys Gly Thr Gly Asp Pro Arg Ala Thr Ala Phe
            325                 330                 335

Ile Glu Gln Leu Glu Ala Ser Val Ala Asp Arg Leu Ala Ser Gln Pro
        340                 345                 350

Glu Pro Met Arg Ile Pro Leu Ala Ser Leu Val Leu Ala Lys Arg Ala
    355                 360                 365

<210> SEQ ID NO 2
<211> LENGTH: 360
<212> TYPE: PRT
<213> ORGANISM: Mycobacterium smegmatis

<400> SEQUENCE: 2

Met Pro Lys Phe Arg Val Ala Val Asp Pro Glu Pro Asp Asp Pro Thr
1               5                   10                  15

Pro Lys Met Arg Ala Pro Arg Pro His Ala Ala Gly Leu Asn Ser Ala
            20                  25                  30

Ile Ala Leu Leu Glu Glu Ala Ala Arg Thr Val Pro Leu Pro Glu Ala
        35                  40                  45

Pro Tyr Pro Ile Val Ile Ala Asp Tyr Gly Val Gly Thr Gly Arg Asn
    50                  55                  60

Ser Met Arg Pro Ile Ala Ala Ile Ala Ala Leu Arg Gly Arg Thr
65                  70                  75                  80

Arg Pro Glu His Ser Val Leu Val Thr His Thr Asp Asn Ala Asp Asn
                85                  90                  95

Asp Phe Thr Ala Val Phe Arg Gly Leu Ala Asp Asn Pro Asp Ser Tyr
            100                 105                 110

Leu Arg Arg Asp Thr Ser Thr Tyr Pro Ser Ala Val Gly Arg Ser Phe
        115                 120                 125

Tyr Thr Gln Ile Leu Pro Ser Lys Ser Val His Val Gly Trp Ser Ala
    130                 135                 140

Trp Ala Ile Val Arg Val Gly Arg Met Pro Met Pro Val Pro Asp His
145                 150                 155                 160

Val Ala Ala Ser Phe Ser Gly Asp Pro Gln Val Val Ala Ala Tyr Ala
                165                 170                 175

Arg Gln Ala Ala Phe Asp Trp His Glu Phe Val Ala Phe Arg Gly Arg
            180                 185                 190

Glu Leu Ala Ser Gly Ala Gln Leu Val Val Leu Thr Ala Ala Leu Gly
        195                 200                 205

Asp Asp Gly Asp Phe Gly Tyr Arg Pro Leu Phe Ala Ala Val Met Asp
    210                 215                 220

Thr Leu Arg Glu Leu Thr Ala Asp Gly Val Leu Arg Gln Asp Glu Leu
225                 230                 235                 240

His Arg Met Ser Leu Pro Ile Val Gly Arg Ala Asn Asp Phe Met
                245                 250                 255

Ala Pro Phe Ala Pro Ser Gly Arg Phe Glu Arg Leu Ser Ile Ser His
            260                 265                 270

Leu Glu Val Tyr Asp Ala Glu Asp Val Ile Tyr Ser Ser Tyr Gln Lys
        275                 280                 285

Asp Arg Asp Thr Asp Val Phe Gly Leu Arg Trp Ala Asp Phe Cys Arg
    290                 295                 300

Phe Thr Phe Phe Ser Asp Leu Cys Thr Ala Leu Asp Asp Asp Ala Ala
```

```
            305                 310                 315                 320
Arg Cys Thr Gln Phe Gln Asp Arg Leu His Ala Gly Ile Ala Ala Arg
                    325                 330                 335

Leu Ser Ala Gln Pro Glu Gln Met Arg Ile Pro Leu Ala Gln Leu Val
                340                 345                 350

Leu Glu Arg Arg Arg Ser Gly
            355                 360

<210> SEQ ID NO 3
<211> LENGTH: 394
<212> TYPE: PRT
<213> ORGANISM: Pseudomonas putida

<400> SEQUENCE: 3

Met Leu Ala Gln Leu Pro Pro Ala Leu Gln Ser Leu His Leu Pro Leu
  1               5                  10                  15

Arg Leu Lys Leu Trp Asp Gly Asn Gln Phe Asp Leu Gly Pro Ser Pro
             20                  25                  30

Gln Val Thr Ile Leu Val Lys Glu Pro Gln Leu Ile Gly Gln Leu Thr
         35                  40                  45

His Pro Ser Met Glu Gln Leu Gly Thr Ala Phe Val Glu Gly Lys Leu
     50                  55                  60

Glu Leu Glu Gly Asp Ile Gly Glu Ala Ile Arg Val Cys Asp Glu Leu
 65                  70                  75                  80

Ser Glu Ala Leu Phe Thr Asp Glu Asp Glu Gln Pro Pro Glu Arg Arg
                 85                  90                  95

Ser His Asp Lys Arg Thr Asp Ala Glu Ala Ile Ser Tyr His Tyr Asp
            100                 105                 110

Val Ser Asn Ala Phe Tyr Gln Leu Trp Leu Asp Gln Asp Met Ala Tyr
        115                 120                 125

Ser Cys Ala Tyr Phe Arg Glu Pro Asp Asn Thr Leu Asp Gln Ala Gln
    130                 135                 140

Gln Asp Lys Phe Asp His Leu Cys Arg Lys Leu Arg Leu Asn Ala Gly
145                 150                 155                 160

Asp Tyr Leu Leu Asp Val Gly Cys Gly Trp Gly Gly Leu Ala Arg Phe
                165                 170                 175

Ala Ala Arg Glu Tyr Asp Ala Lys Val Phe Gly Ile Thr Leu Ser Lys
            180                 185                 190

Glu Gln Leu Lys Leu Gly Arg Gln Arg Val Lys Ala Glu Gly Leu Thr
        195                 200                 205

Asp Lys Val Asp Leu Gln Ile Leu Asp Tyr Arg Asp Leu Pro Gln Asp
    210                 215                 220

Gly Arg Phe Asp Lys Val Val Ser Val Gly Met Phe Glu His Val Gly
225                 230                 235                 240

His Ala Asn Leu Ala Leu Tyr Cys Gln Lys Leu Phe Gly Ala Val Arg
                245                 250                 255

Glu Gly Gly Leu Val Met Asn His Gly Ile Thr Ala Lys His Val Asp
            260                 265                 270

Gly Arg Pro Val Gly Arg Gly Ala Gly Glu Phe Ile Asp Arg Tyr Val
        275                 280                 285

Phe Pro His Gly Glu Leu Pro His Leu Ser Met Ile Ser Ala Ser Ile
    290                 295                 300

Cys Glu Ala Gly Leu Glu Val Val Asp Val Glu Ser Leu Arg Leu His
305                 310                 315                 320
```

```
Tyr Ala Lys Thr Leu His His Trp Ser Glu Asn Leu Glu Asn Gln Leu
                325                 330                 335

His Lys Ala Ala Ala Leu Val Pro Glu Lys Thr Leu Arg Ile Trp Arg
            340                 345                 350

Leu Tyr Leu Ala Gly Cys Ala Tyr Ala Phe Glu Lys Gly Trp Ile Asn
        355                 360                 365

Leu His Gln Ile Leu Ala Val Lys Pro Tyr Ala Asp Gly His His Asp
    370                 375                 380

Leu Pro Trp Thr Arg Glu Asp Met Tyr Arg
385                 390

<210> SEQ ID NO 4
<211> LENGTH: 246
<212> TYPE: PRT
<213> ORGANISM: Lactobacillus brevis

<400> SEQUENCE: 4

Met Ala Ala Asn Glu Phe Ser Glu Thr His Arg Val Val Tyr Tyr Glu
  1               5                  10                  15

Ala Asp Asp Thr Gly Gln Leu Thr Leu Ala Met Leu Ile Asn Leu Phe
             20                  25                  30

Val Leu Val Ser Glu Asp Gln Asn Asp Ala Leu Gly Leu Ser Thr Ala
         35                  40                  45

Phe Val Gln Ser His Gly Val Gly Trp Val Val Thr Gln Tyr His Leu
     50                  55                  60

His Ile Asp Glu Leu Pro Arg Thr Gly Ala Gln Val Thr Ile Lys Thr
 65                  70                  75                  80

Arg Ala Thr Ala Tyr Asn Arg Tyr Phe Ala Tyr Arg Glu Tyr Trp Leu
                 85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245

<210> SEQ ID NO 5
<211> LENGTH: 261
<212> TYPE: PRT
<213> ORGANISM: Lactobacillus plantarum

<400> SEQUENCE: 5
```

```
Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
50                  55                  60

Thr Gln Tyr Ala Ile Asp Ile Thr Arg Met Pro Arg Gln Asp Glu Val
65                  70                  75                  80

Val Thr Ile Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
            100                 105                 110

Thr Ser Ile Trp Val Met Met Ser Gln Thr Thr Arg Arg Ile Val Lys
        115                 120                 125

Ile Leu Pro Glu Leu Val Ala Pro Tyr Gln Ser Glu Val Val Lys Arg
    130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
            180                 185                 190

Ala Thr Phe Leu Leu Gln His Asp Leu Val His Val Asp Val Arg Tyr
        195                 200                 205

Glu Asn Glu Val Lys Tyr Gly Gln Thr Val Thr Ala His Ala Asn Ile
    210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260

<210> SEQ ID NO 6
<211> LENGTH: 256
<212> TYPE: PRT
<213> ORGANISM: Escherichia coli

<400> SEQUENCE: 6

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
        35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110
```

```
Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255

<210> SEQ ID NO 7
<211> LENGTH: 1174
<212> TYPE: PRT
<213> ORGANISM: Mycobacterium marinum

<400> SEQUENCE: 7

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
    210                 215                 220

Arg Gly Asp Val Pro Arg Gly Ala Ser Ala Gly Ser Ala Pro Gly Thr
```

```
                225                 230                 235                 240
Asp Val Ser Asp Asp Ser Leu Ala Leu Leu Ile Tyr Thr Ser Gly Ser
                    245                 250                 255
Thr Gly Ala Pro Lys Gly Ala Met Tyr Pro Arg Arg Asn Val Ala Thr
                    260                 265                 270
Phe Trp Arg Lys Arg Thr Trp Phe Glu Gly Tyr Glu Pro Ser Ile
                275                 280                 285
Thr Leu Asn Phe Met Pro Met Ser His Val Met Gly Arg Gln Ile Leu
    290                 295                 300
Tyr Gly Thr Leu Cys Asn Gly Gly Thr Ala Tyr Phe Val Ala Lys Ser
305                 310                 315                 320
Asp Leu Ser Thr Leu Phe Glu Asp Leu Ala Leu Val Arg Pro Thr Glu
                    325                 330                 335
Leu Thr Phe Val Pro Arg Val Trp Asp Met Val Phe Asp Glu Phe Gln
                340                 345                 350
Ser Glu Val Asp Arg Arg Leu Val Asp Gly Ala Asp Arg Val Ala Leu
                355                 360                 365
Glu Ala Gln Val Lys Ala Glu Ile Arg Asn Asp Val Leu Gly Gly Arg
    370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                    405                 410                 415
Ser Thr Glu Ala Gly Met Ile Leu Ile Asp Gly Ala Ile Arg Arg Pro
                420                 425                 430
Ala Val Leu Asp Tyr Lys Leu Val Asp Val Pro Asp Leu Gly Tyr Phe
                435                 440                 445
Leu Thr Asp Arg Pro His Pro Arg Gly Glu Leu Val Lys Thr Asp
    450                 455                 460
Ser Leu Phe Pro Gly Tyr Tyr Gln Arg Ala Glu Val Thr Ala Asp Val
465                 470                 475                 480
Phe Asp Ala Asp Gly Phe Tyr Arg Thr Gly Asp Ile Met Ala Glu Val
                485                 490                 495
Gly Pro Glu Gln Phe Val Tyr Leu Asp Arg Arg Asn Asn Val Leu Lys
                500                 505                 510
Leu Ser Gln Gly Glu Phe Val Thr Val Ser Lys Leu Glu Ala Val Phe
                515                 520                 525
Gly Asp Ser Pro Leu Val Arg Gln Ile Tyr Ile Tyr Gly Asn Ser Ala
                530                 535                 540
Arg Ala Tyr Leu Leu Ala Val Ile Val Pro Thr Gln Glu Ala Leu Asp
545                 550                 555                 560
Ala Val Pro Val Glu Glu Leu Lys Ala Arg Leu Gly Asp Ser Leu Gln
                565                 570                 575
Glu Val Ala Lys Ala Ala Gly Leu Gln Ser Tyr Glu Ile Pro Arg Asp
                580                 585                 590
Phe Ile Ile Glu Thr Thr Pro Trp Thr Leu Glu Asn Gly Leu Leu Thr
                595                 600                 605
Gly Ile Arg Lys Leu Ala Arg Pro Gln Leu Lys Lys His Tyr Gly Glu
    610                 615                 620
Leu Leu Glu Gln Ile Tyr Thr Asp Leu Ala His Gly Gln Ala Asp Glu
625                 630                 635                 640
Leu Arg Ser Leu Arg Gln Ser Gly Ala Asp Ala Pro Val Leu Val Thr
                645                 650                 655
```

```
Val Cys Arg Ala Ala Ala Ala Leu Leu Gly Gly Ser Ala Ser Asp Val
                660                 665                 670

Gln Pro Asp Ala His Phe Thr Asp Leu Gly Gly Asp Ser Leu Ser Ala
                675                 680                 685

Leu Ser Phe Thr Asn Leu Leu His Glu Ile Phe Asp Ile Glu Val Pro
                690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
                740                 745                 750

Asp Leu Ser Leu Asp Lys Phe Ile Asp Ala Ala Thr Leu Ala Glu Ala
                755                 760                 765

Pro Arg Leu Pro Ala Ala Asn Thr Gln Val Arg Thr Val Leu Leu Thr
                770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
                820                 825                 830

Asp Pro Glu Leu Leu Ala His Tyr Arg Ala Leu Ala Gly Asp His Leu
                835                 840                 845

Glu Val Leu Ala Gly Asp Lys Gly Glu Ala Asp Leu Gly Leu Asp Arg
                850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
                900                 905                 910

Ile Lys Pro Tyr Ser Tyr Thr Ser Thr Ile Gly Val Ala Asp Gln Ile
                915                 920                 925

Pro Pro Ser Ala Phe Thr Glu Asp Ala Asp Ile Arg Val Ile Ser Ala
                930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
                980                 985                 990

Ala Gly Gln Leu Asn Val Pro Asp Met Phe Thr Arg Met Ile Leu Ser
                995                 1000                1005

Leu Ala Ala Thr Gly Ile Ala Pro Gly Ser Phe Tyr Glu Leu Ala Ala
                1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Asp Gly Ile Gly Leu Asp
                1060                1065                1070
```

-continued

```
Glu Phe Val Asp Trp Leu Asn Glu Ser Gly Cys Pro Ile Gln Arg Ile
        1075                1080                1085

Ala Asp Tyr Gly Asp Trp Leu Gln Arg Phe Glu Thr Ala Leu Arg Ala
        1090                1095                1100

Leu Pro Asp Arg Gln Arg His Ser Ser Leu Leu Pro Leu Leu His Asn
1105                1110                1115                1120

Tyr Arg Gln Pro Glu Arg Pro Val Arg Gly Ser Ile Ala Pro Thr Asp
        1125                1130                1135

Arg Phe Arg Ala Ala Val Gln Glu Ala Lys Ile Gly Pro Asp Lys Asp
        1140                1145                1150

Ile Pro His Val Gly Ala Pro Ile Ile Val Lys Tyr Val Ser Asp Leu
        1155                1160                1165

Arg Leu Leu Gly Leu Leu
        1170

<210> SEQ ID NO 8
<211> LENGTH: 1173
<212> TYPE: PRT
<213> ORGANISM: Mycobacterium smegmatis

<400> SEQUENCE: 8

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
            85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
            165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
            245                 250                 255

Leu Ala Met Ile Leu Tyr Thr Ser Gly Ser Thr Gly Ala Pro Lys Gly
            260                 265                 270
```

```
Ala Met Tyr Thr Glu Ala Met Val Ala Arg Leu Trp Thr Met Ser Phe
            275                 280                 285
Ile Thr Gly Asp Pro Thr Pro Val Ile Asn Val Asn Phe Met Pro Leu
        290                 295                 300
Asn His Leu Gly Gly Arg Ile Pro Ile Ser Thr Ala Val Gln Asn Gly
305                 310                 315                 320
Gly Thr Ser Tyr Phe Val Pro Glu Ser Asp Met Ser Thr Leu Phe Glu
                325                 330                 335
Asp Leu Ala Leu Val Arg Pro Thr Glu Leu Gly Leu Val Pro Arg Val
                340                 345                 350
Ala Asp Met Leu Tyr Gln His His Leu Ala Thr Val Asp Arg Leu Val
            355                 360                 365
Thr Gln Gly Ala Asp Glu Leu Thr Ala Glu Lys Gln Ala Gly Ala Glu
        370                 375                 380
Leu Arg Glu Gln Val Leu Gly Arg Val Ile Thr Gly Phe Val Ser
385                 390                 395                 400
Thr Ala Pro Leu Ala Ala Glu Met Arg Ala Phe Leu Asp Ile Thr Leu
                405                 410                 415
Gly Ala His Ile Val Asp Gly Tyr Gly Leu Thr Glu Thr Gly Ala Val
            420                 425                 430
Thr Arg Asp Gly Val Ile Val Arg Pro Pro Val Ile Asp Tyr Lys Leu
        435                 440                 445
Ile Asp Val Pro Glu Leu Gly Tyr Phe Ser Thr Asp Lys Pro Tyr Pro
450                 455                 460
Arg Gly Glu Leu Leu Val Arg Ser Gln Thr Leu Thr Pro Gly Tyr Tyr
465                 470                 475                 480
Lys Arg Pro Glu Val Thr Ala Ser Val Phe Asp Arg Asp Gly Tyr Tyr
                485                 490                 495
His Thr Gly Asp Val Met Ala Glu Thr Ala Pro Asp His Leu Val Tyr
            500                 505                 510
Val Asp Arg Arg Asn Asn Val Leu Lys Leu Ala Gln Gly Glu Phe Val
        515                 520                 525
Ala Val Ala Asn Leu Glu Ala Val Phe Ser Gly Ala Ala Leu Val Arg
    530                 535                 540
Gln Ile Phe Val Tyr Gly Asn Ser Glu Arg Ser Phe Leu Leu Ala Val
545                 550                 555                 560
Val Val Pro Thr Pro Glu Ala Leu Glu Gln Tyr Asp Pro Ala Ala Leu
                565                 570                 575
Lys Ala Ala Leu Ala Asp Ser Leu Gln Arg Thr Ala Arg Asp Ala Glu
            580                 585                 590
Leu Gln Ser Tyr Glu Val Pro Ala Asp Phe Ile Val Glu Thr Glu Pro
        595                 600                 605
Phe Ser Ala Ala Asn Gly Leu Leu Ser Gly Val Gly Lys Leu Leu Arg
610                 615                 620
Pro Asn Leu Lys Asp Arg Tyr Gly Gln Arg Leu Glu Gln Met Tyr Ala
625                 630                 635                 640
Asp Ile Ala Ala Thr Gln Ala Asn Gln Leu Arg Glu Leu Arg Arg Ala
                645                 650                 655
Ala Ala Thr Gln Pro Val Ile Asp Thr Leu Thr Gln Ala Ala Ala Thr
            660                 665                 670
Ile Leu Gly Thr Gly Ser Glu Val Ala Ser Asp Ala His Phe Thr Asp
        675                 680                 685
```

-continued

```
Leu Gly Gly Asp Ser Leu Ser Ala Leu Thr Leu Ser Asn Leu Leu Ser
    690                 695                 700

Asp Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
                740                 745                 750

Glu Ile Arg Ala Ser Glu Leu Thr Leu Asp Lys Phe Ile Asp Ala Glu
                755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
                820                 825                 830

Ala Tyr Asp Thr Asp Pro Glu Leu Ser Arg Arg Phe Ala Glu Leu Ala
                835                 840                 845

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
                900                 905                 910

Leu Thr Glu Arg Ile Lys Pro Val Thr Tyr Leu Ser Thr Val Ser Val
                915                 920                 925

Ala Met Gly Ile Pro Asp Phe Glu Glu Asp Gly Asp Ile Arg Thr Val
                930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
                980                 985                 990

Arg Tyr Arg Gly Gln Val Asn Val Pro Asp Met Phe Thr Arg Leu Leu
                995                 1000                1005

Leu Ser Leu Leu Ile Thr Gly Val Ala Pro Arg Ser Phe Tyr Ile Gly
    1010                1015                1020

Asp Gly Glu Arg Pro Arg Ala His Tyr Pro Gly Leu Thr Val Asp Phe
1025                1030                1035                1040

Val Ala Glu Ala Val Thr Thr Leu Gly Ala Gln Gln Arg Glu Gly Tyr
                1045                1050                1055

Val Ser Tyr Asp Val Met Asn Pro His Asp Asp Gly Ile Ser Leu Asp
                1060                1065                1070

Val Phe Val Asp Trp Leu Ile Arg Ala Gly His Pro Ile Asp Arg Val
                1075                1080                1085

Asp Asp Tyr Asp Asp Trp Val Arg Arg Phe Glu Thr Ala Leu Thr Ala
                1090                1095                1100

Leu Pro Glu Lys Arg Arg Ala Gln Thr Val Leu Pro Leu Leu His Ala
```

```
                  1105                1110                1115                1120
        Phe Arg Ala Pro Gln Ala Pro Leu Arg Gly Ala Pro Glu Pro Thr Glu
                            1125                1130                1135

Val Phe His Ala Ala Val Arg Thr Ala Lys Val Gly Pro Gly Asp Ile
                    1140                1145                1150

Pro His Leu Asp Glu Ala Leu Ile Asp Lys Tyr Ile Arg Asp Leu Arg
                1155                1160                1165

Glu Phe Gly Leu Ile
            1170

<210> SEQ ID NO 9
<211> LENGTH: 1148
<212> TYPE: PRT
<213> ORGANISM: Segniliparus rugosus

<400> SEQUENCE: 9

Met Gly Asp Gly Glu Glu Arg Ala Lys Arg Phe Phe Gln Arg Ile Gly
        1               5                   10                  15

Glu Leu Ser Ala Thr Asp Pro Gln Phe Ala Ala Ala Pro Asp Pro
                    20                  25                  30

Ala Val Val Glu Ala Val Ser Asp Pro Ser Leu Ser Phe Thr Arg Tyr
                    35                  40                  45

Leu Asp Thr Leu Met Arg Gly Tyr Ala Glu Arg Pro Ala Leu Ala His
            50                  55                  60

Arg Val Gly Ala Gly Tyr Glu Thr Ile Ser Tyr Gly Glu Leu Trp Ala
        65                  70                  75                  80

Arg Val Gly Ala Ile Ala Ala Ala Trp Gln Ala Asp Gly Leu Ala Pro
                        85                  90                  95

Gly Asp Phe Val Ala Thr Val Gly Phe Thr Ser Pro Asp Tyr Val Ala
                    100                 105                 110

Val Asp Leu Ala Ala Ala Arg Ser Gly Leu Val Ser Val Pro Leu Gln
                    115                 120                 125

Ala Gly Ala Ser Leu Ala Gln Leu Val Gly Ile Leu Glu Glu Thr Glu
                130                 135                 140

Pro Lys Val Leu Ala Ala Ser Ala Ser Ser Leu Glu Gly Ala Val Ala
        145                 150                 155                 160

Cys Ala Leu Ala Ala Pro Ser Val Gln Arg Leu Val Val Phe Asp Leu
                        165                 170                 175

Arg Gly Pro Asp Ala Ser Glu Ser Ala Ala Asp Glu Arg Arg Gly Ala
                    180                 185                 190

Leu Ala Asp Ala Glu Glu Gln Leu Ala Arg Ala Gly Arg Ala Val Val
                    195                 200                 205

Val Glu Thr Leu Ala Asp Leu Ala Ala Arg Gly Glu Ala Leu Pro Glu
                210                 215                 220

Ala Pro Leu Phe Glu Pro Ala Glu Gly Glu Asp Pro Leu Ala Leu Leu
        225                 230                 235                 240

Ile Tyr Thr Ser Gly Ser Thr Gly Ala Pro Lys Gly Ala Met Tyr Ser
                        245                 250                 255

Gln Arg Leu Val Ser Gln Leu Trp Gly Arg Thr Pro Val Val Pro Gly
                    260                 265                 270

Met Pro Asn Ile Ser Leu His Tyr Met Pro Leu Ser His Ser Tyr Gly
                    275                 280                 285

Arg Ala Val Leu Ala Gly Ala Leu Ser Ala Gly Gly Thr Ala His Phe
                290                 295                 300
```

```
Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
            325                 330                 335

Gln Glu Ser Gln Arg Gly Gln Asp Val Ala Glu Leu Arg Glu Arg Val
        340                 345                 350

Leu Gly Gly Arg Leu Leu Val Ala Val Cys Gly Ser Ala Pro Leu Ser
    355                 360                 365

Pro Glu Met Arg Ala Phe Met Glu Glu Val Leu Gly Phe Pro Leu Leu
370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
            405                 410                 415

Leu Gly Tyr Arg Thr Thr Asp Lys Pro Tyr Pro Arg Gly Glu Leu Cys
        420                 425                 430

Ile Arg Ser Thr Ser Leu Ile Ser Gly Tyr Tyr Lys Arg Pro Glu Ile
    435                 440                 445

Thr Ala Glu Val Phe Asp Ala Gln Gly Tyr Tyr Lys Thr Gly Asp Val
450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
            485                 490                 495

Glu Ala Ala Tyr Gly Thr Ser Pro Tyr Val Lys Gln Ile Phe Val Tyr
        500                 505                 510

Gly Asn Ser Glu Arg Ser Phe Leu Leu Ala Val Val Pro Asn Ala
    515                 520                 525

Glu Val Leu Gly Ala Arg Asp Gln Glu Glu Ala Lys Pro Leu Ile Ala
530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
            565                 570                 575

Gly Leu Leu Ser Glu Val Gly Lys Leu Leu Arg Pro Lys Leu Lys Ala
        580                 585                 590

Arg Tyr Gly Glu Ala Leu Glu Ala Arg Tyr Asp Glu Ile Ala His Gly
    595                 600                 605

Gln Ala Asp Glu Leu Arg Ala Leu Arg Asp Gly Ala Gly Gln Arg Pro
610                 615                 620

Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
            645                 650                 655

Ser Leu Ser Ala Leu Ser Leu Ala Asn Leu Leu His Asp Val Phe Glu
        660                 665                 670

Val Glu Val Pro Val Arg Ile Ile Gly Pro Thr Ala Ser Leu Ala
    675                 680                 685

Gly Ile Ala Lys His Ile Glu Ala Glu Arg Ala Gly Ser Ala Pro
690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
```

```
                    725                 730                 735
Lys Gly Leu Pro Ala Ala Asp Gln Val Arg Thr Val Leu Leu Thr Gly
                740                 745                 750

Ala Asn Gly Trp Leu Gly Arg Phe Leu Ala Leu Glu Gln Leu Glu Arg
            755                 760                 765

Leu Ala Arg Ser Gly Gln Asp Gly Gly Lys Leu Ile Cys Leu Val Arg
        770                 775                 780

Gly Lys Asp Ala Ala Ala Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Val Ile Val His
        835                 840                 845

Pro Ala Ala Leu Val Asn His Val Leu Pro Tyr His Gln Leu Phe Gly
    850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                885                 890                 895

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
        915                 920                 925

Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                 1000                1005

Phe Thr Ala Glu Ala Ile Thr Thr Leu Gly Ala Glu Pro Ser Trp Phe
    1010                1015                1020

Asp Gly Gly Ala Gly Phe Arg Ser Phe Asp Val Phe Asn Pro His His
1025                1030                1035                1040

Asp Gly Val Gly Leu Asp Glu Phe Val Asp Trp Leu Ile Glu Ala Gly
                1045                1050                1055

His Pro Ile Ser Arg Ile Asp Asp His Lys Glu Trp Phe Ala Arg Phe
            1060                1065                1070

Glu Thr Ala Val Arg Gly Leu Pro Glu Ala Gln Arg Gln His Ser Leu
        1075                1080                1085

Leu Pro Leu Leu Arg Ala Tyr Ser Phe Pro His Pro Pro Val Asp Gly
    1090                1095                1100

Ser Val Tyr Pro Thr Gly Lys Phe Gln Gly Ala Val Lys Ala Ala Gln
1105                1110                1115                1120

Val Gly Ser Asp His Asp Val Pro His Leu Gly Lys Ala Leu Ile Val
                1125                1130                1135

Lys Tyr Ala Asp Asp Leu Lys Ala Leu Gly Leu Leu
            1140                1145
```

<210> SEQ ID NO 10
<211> LENGTH: 1168
<212> TYPE: PRT
<213> ORGANISM: Mycobacterium smegmatis

<400> SEQUENCE: 10

```
Met Thr Ile Glu Thr Arg Glu Asp Arg Phe Asn Arg Ile Asp His
 1               5                  10                  15

Leu Phe Glu Thr Asp Pro Gln Phe Ala Ala Arg Pro Asp Glu Ala
                20                  25                  30

Ile Ser Ala Ala Ala Asp Pro Glu Leu Arg Leu Pro Ala Ala Val
                35                  40                  45

Lys Gln Ile Leu Ala Gly Tyr Ala Asp Arg Pro Ala Leu Gly Lys Arg
 50                  55                  60

Ala Val Glu Phe Val Thr Asp Glu Glu Gly Arg Thr Thr Ala Lys Leu
 65                  70                  75                  80

Leu Pro Arg Phe Asp Thr Ile Thr Tyr Arg Gln Leu Ala Gly Arg Ile
                 85                  90                  95

Gln Ala Val Thr Asn Ala Trp His Asn His Pro Val Asn Ala Gly Asp
                100                 105                 110

Arg Val Ala Ile Leu Gly Phe Thr Ser Val Asp Tyr Thr Thr Ile Asp
                115                 120                 125

Ile Ala Leu Leu Glu Leu Gly Ala Val Ser Val Pro Leu Gln Thr Ser
                130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
                180                 185                 190

Glu Val Asp Asp Gln Arg Glu Ala Phe Glu Ala Ala Lys Gly Lys Leu
                195                 200                 205

Ala Gly Thr Gly Val Val Glu Thr Ile Thr Asp Ala Leu Asp Arg
                210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
                260                 265                 270

Ser Lys Ala Arg Trp Asp Glu Thr Leu Gly Val Met Pro Ser Ile Thr
                275                 280                 285

Leu Asn Phe Met Pro Met Ser His Val Met Gly Arg Gly Ile Leu Cys
                290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
                340                 345                 350

Arg Leu Asp Asn Arg Arg Ala Glu Gly Ser Glu Asp Arg Ala Glu Ala
                355                 360                 365

Ala Val Leu Glu Glu Val Arg Thr Gln Leu Leu Gly Gly Arg Phe Val
```

```
                370                 375                 380
Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
            435                 440                 445

Asp Arg Pro Tyr Pro Arg Gly Glu Leu Leu Val Lys Ser Glu Gln Met
        450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
530                 535                 540

Tyr Leu Ala Val Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
            595                 600                 605

Arg Lys Leu Ala Arg Pro Lys Leu Lys Ala His Tyr Gly Glu Arg Leu
        610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
            675                 680                 685

Phe Ser Asn Leu Leu His Glu Ile Phe Asp Val Asp Val Pro Val Gly
        690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
                725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Pro Gly Leu Pro Arg Ser
            755                 760                 765

Gly Thr Glu Ile Arg Thr Val Leu Leu Thr Gly Ala Thr Gly Phe Leu
        770                 775                 780

Gly Arg Tyr Leu Ala Leu Glu Trp Leu Glu Arg Met Asp Leu Val Asp
785                 790                 795                 800
```

Gly Lys Val Ile Cys Leu Val Arg Ala Arg Ser Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
                835                 840                 845

Lys Gly Glu Ala Asp Leu Gly Leu Asp His Asp Thr Trp Gln Arg Leu
            850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
            915                 920                 925

Glu Asp Ala Asp Ile Arg Glu Ile Ser Ala Thr Arg Arg Val Asp Asp
            930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
            995                 1000                1005

Ala Pro Gly Ser Phe Tyr Glu Leu Asp Ala Asp Gly Asn Arg Gln Arg
            1010                1015                1020

Ala His Tyr Asp Gly Leu Pro Val Glu Phe Ile Ala Glu Ala Ile Ser
1025                1030                1035                1040

Thr Ile Gly Ser Gln Val Thr Asp Gly Phe Glu Thr Phe His Val Met
                1045                1050                1055

Asn Pro Tyr Asp Asp Gly Ile Gly Leu Asp Glu Tyr Val Asp Trp Leu
            1060                1065                1070

Ile Glu Ala Gly Tyr Pro Val His Arg Val Asp Asp Tyr Ala Thr Trp
            1075                1080                1085

Leu Ser Arg Phe Glu Thr Ala Leu Arg Ala Leu Pro Glu Arg Gln Arg
            1090                1095                1100

Gln Ala Ser Leu Leu Pro Leu Leu His Asn Tyr Gln Gln Pro Ser Pro
1105                1110                1115                1120

Pro Val Cys Gly Ala Met Ala Pro Thr Asp Arg Phe Arg Ala Ala Val
                1125                1130                1135

Gln Asp Ala Lys Ile Gly Pro Asp Lys Asp Ile Pro His Val Thr Ala
            1140                1145                1150

Asp Val Ile Val Lys Tyr Ile Ser Asn Leu Gln Met Leu Gly Leu Leu
            1155                1160                1165

<210> SEQ ID NO 11
<211> LENGTH: 1185
<212> TYPE: PRT
<213> ORGANISM: Mycobacterium massiliense

<400> SEQUENCE: 11

Met Thr Asn Glu Thr Asn Pro Gln Gln Glu Gln Leu Ser Arg Arg Ile

```
                1               5                    10                       15
            Glu Ser Leu Arg Glu Ser Asp Pro Gln Phe Arg Ala Ala Gln Pro Asp
                            20                  25                  30

Pro Ala Val Ala Glu Gln Val Leu Arg Pro Gly Leu His Leu Ser Glu
                            35                  40                  45

Ala Ile Ala Ala Leu Met Thr Gly Tyr Ala Glu Arg Pro Ala Leu Gly
                50                          55                  60

Glu Arg Ala Arg Glu Leu Val Ile Asp Gln Asp Gly Arg Thr Thr Leu
             65                         70                  75                  80

Arg Leu Leu Pro Arg Phe Asp Thr Thr Tyr Gly Glu Leu Trp Ser
                            85                  90                  95

Arg Thr Thr Ser Val Ala Ala Ala Trp His His Asp Ala Thr His Pro
                            100                 105                 110

Val Lys Ala Gly Asp Leu Val Ala Thr Leu Gly Phe Thr Ser Ile Asp
                            115                 120                 125

Tyr Thr Val Leu Asp Leu Ala Ile Met Ile Leu Gly Gly Val Ala Val
                130                         135                 140

Pro Leu Gln Thr Ser Ala Pro Ala Ser Gln Trp Thr Thr Ile Leu Ala
            145                         150                 155                 160

Glu Ala Glu Pro Asn Thr Leu Ala Val Ser Ile Glu Leu Ile Gly Ala
                            165                 170                 175

Ala Met Glu Ser Val Arg Ala Thr Pro Ser Ile Lys Gln Val Val Val
                            180                 185                 190

Phe Asp Tyr Thr Pro Glu Val Asp Asp Gln Arg Glu Ala Phe Glu Ala
                            195                 200                 205

Ala Ser Thr Gln Leu Ala Gly Thr Gly Ile Ala Leu Glu Thr Leu Asp
                210                         215                 220

Ala Val Ile Ala Arg Gly Ala Ala Leu Pro Ala Ala Pro Leu Tyr Ala
            225                         230                 235                 240

Pro Ser Ala Gly Asp Asp Pro Leu Ala Leu Leu Ile Tyr Thr Ser Gly
                            245                 250                 255

Ser Thr Gly Ala Pro Lys Gly Ala Met His Ser Glu Asn Ile Val Arg
                            260                 265                 270

Arg Trp Trp Ile Arg Glu Asp Val Met Ala Gly Thr Glu Asn Leu Pro
                            275                 280                 285

Met Ile Gly Leu Asn Phe Met Pro Met Ser His Ile Met Gly Arg Gly
                            290                 295                 300

Thr Leu Thr Ser Thr Leu Ser Thr Gly Gly Thr Gly Tyr Phe Ala Ala
            305                         310                 315                 320

Ser Ser Asp Met Ser Thr Leu Phe Glu Asp Met Glu Leu Ile Arg Pro
                            325                 330                 335

Thr Ala Leu Ala Leu Val Pro Arg Val Cys Asp Met Val Phe Gln Arg
                            340                 345                 350

Phe Gln Thr Glu Val Asp Arg Arg Leu Ala Ser Gly Asp Thr Ala Ser
                            355                 360                 365

Ala Glu Ala Val Ala Ala Glu Val Lys Ala Asp Ile Arg Asp Asn Leu
                            370                 375                 380

Phe Gly Gly Arg Val Ser Ala Val Met Val Gly Ser Ala Pro Leu Ser
            385                         390                 395                 400

Glu Glu Leu Gly Glu Phe Ile Glu Ser Cys Phe Glu Leu Asn Leu Thr
                            405                 410                 415

Asp Gly Tyr Gly Ser Thr Glu Ala Gly Met Val Phe Arg Asp Gly Ile
                            420                 425                 430
```

```
Val Gln Arg Pro Pro Val Ile Asp Tyr Lys Leu Val Asp Val Pro Glu
        435                 440                 445
Leu Gly Tyr Phe Ser Thr Asp Lys Pro His Pro Arg Gly Glu Leu Leu
    450                 455                 460
Leu Lys Thr Asp Gly Met Phe Leu Gly Tyr Tyr Lys Arg Pro Glu Val
465                 470                 475                 480
Thr Ala Ser Val Phe Asp Ala Asp Gly Phe Tyr Met Thr Gly Asp Ile
                485                 490                 495
Val Ala Glu Leu Ala His Asp Asn Ile Glu Ile Ile Asp Arg Arg Asn
            500                 505                 510
Asn Val Leu Lys Leu Ser Gln Gly Glu Phe Val Ala Val Ala Thr Leu
        515                 520                 525
Glu Ala Glu Tyr Ala Asn Ser Pro Val Val His Gln Ile Tyr Val Tyr
    530                 535                 540
Gly Ser Ser Glu Arg Ser Tyr Leu Leu Ala Val Val Val Pro Thr Pro
545                 550                 555                 560
Glu Ala Val Ala Ala Ala Lys Gly Asp Ala Ala Ala Leu Lys Thr Thr
                565                 570                 575
Ile Ala Asp Ser Leu Gln Asp Ile Ala Lys Glu Ile Gln Leu Gln Ser
            580                 585                 590
Tyr Glu Val Pro Arg Asp Phe Ile Ile Glu Pro Gln Pro Phe Thr Gln
        595                 600                 605
Gly Asn Gly Leu Leu Thr Gly Ile Ala Lys Leu Ala Arg Pro Asn Leu
    610                 615                 620
Lys Ala His Tyr Gly Pro Arg Leu Glu Gln Met Tyr Ala Glu Ile Ala
625                 630                 635                 640
Glu Gln Gln Ala Ala Glu Leu Arg Ala Leu His Gly Val Asp Pro Asp
                645                 650                 655
Lys Pro Ala Leu Glu Thr Val Leu Lys Ala Ala Gln Ala Leu Leu Gly
            660                 665                 670
Val Ser Ser Ala Glu Leu Ala Ala Asp Ala His Phe Thr Asp Leu Gly
        675                 680                 685
Gly Asp Ser Leu Ser Ala Leu Ser Phe Ser Asp Leu Leu Arg Asp Ile
    690                 695                 700
Phe Ala Val Glu Val Pro Val Gly Val Ile Val Ser Ala Ala Asn Asp
705                 710                 715                 720
Leu Gly Gly Val Ala Lys Phe Val Asp Glu Gln Arg His Ser Gly Gly
                725                 730                 735
Thr Arg Pro Thr Ala Glu Thr Val His Gly Ala Gly His Thr Glu Ile
            740                 745                 750
Arg Ala Ala Asp Leu Thr Leu Asp Lys Phe Ile Asp Glu Ala Thr Leu
        755                 760                 765
His Ala Ala Pro Ser Leu Pro Lys Ala Ala Gly Ile Pro His Thr Val
    770                 775                 780
Leu Leu Thr Gly Ser Asn Gly Tyr Leu Gly His Tyr Leu Ala Leu Glu
785                 790                 795                 800
Trp Leu Glu Arg Leu Asp Lys Thr Asp Gly Lys Leu Ile Val Ile Val
                805                 810                 815
Arg Gly Lys Asn Ala Glu Ala Ala Tyr Gly Arg Leu Glu Glu Ala Phe
            820                 825                 830
Asp Thr Gly Asp Thr Glu Leu Leu Ala His Phe Arg Ser Leu Ala Asp
        835                 840                 845
```

-continued

```
Lys His Leu Glu Val Leu Ala Gly Asp Ile Gly Asp Pro Asn Leu Gly
    850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
        915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
        995                 1000                1005

Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
1025                1030                1035                1040

Gly Asp Phe Thr Ala Glu Ala Ile Thr Thr Leu Gly Thr Gln Val Pro
                1045                1050                1055

Glu Gly Ser Glu Gly Phe Val Thr Tyr Asp Cys Val Asn Pro His Ala
            1060                1065                1070

Asp Gly Ile Ser Leu Asp Asn Phe Val Asp Trp Leu Ile Glu Ala Gly
        1075                1080                1085

Tyr Pro Ile Ala Arg Ile Asp Asn Tyr Thr Glu Trp Phe Thr Arg Phe
    1090                1095                1100

Asp Thr Ala Ile Arg Gly Leu Ser Glu Lys Gln Lys Gln His Ser Leu
1105                1110                1115                1120

Leu Pro Leu Leu His Ala Phe Glu Gln Pro Ser Ala Ala Glu Asn His
                1125                1130                1135

Gly Val Val Pro Ala Lys Arg Phe Gln His Ala Val Gln Ala Ala Gly
            1140                1145                1150

Ile Gly Pro Val Gly Gln Asp Gly Thr Thr Asp Ile Pro His Leu Ser
        1155                1160                1165

Arg Arg Leu Ile Val Lys Tyr Ala Lys Asp Leu Glu Gln Leu Gly Leu
    1170                1175                1180

Leu
1185

<210> SEQ ID NO 12
<211> LENGTH: 1186
<212> TYPE: PRT
<213> ORGANISM: Segniliparus rotundus

<400> SEQUENCE: 12

Met Thr Gln Ser His Thr Gln Gly Pro Gln Ala Ser Ala Ala His Ser
 1               5                  10                  15

Arg Leu Ala Arg Arg Ala Ala Glu Leu Leu Ala Thr Asp Pro Gln Ala
            20                  25                  30
```

```
Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
            115                 120                 125

Ile Gly Phe Ile Ser Val Asp Tyr Val Ala Ile Asp Ile Ala Gly Val
        130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
            195                 200                 205

Asp Arg Glu Ala Val Glu Ala Ala Lys Arg Lys Ile Ala Asp Ala Gly
        210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
            275                 280                 285

Trp Ala Ala Ala Phe Asp Glu Asp Ala Ala Pro Val Pro Ala Ile
        290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln
            355                 360                 365

Ser Glu Leu Asp Arg Arg Gly Val Gln Asp Gly Thr Arg Glu Ala Glu
        370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
            435                 440                 445
```

```
Thr Asp Tyr Lys Leu Ile Asp Val Pro Glu Leu Gly Tyr Phe Ser Thr
450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
                500                 505                 510

Glu Gln Phe Ala Tyr Val Asp Arg Arg Lys Asn Val Leu Lys Leu Ser
                515                 520                 525

Gln Gly Glu Phe Val Thr Leu Ala Lys Leu Glu Ala Ala Tyr Ser Ser
530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
                580                 585                 590

Ile Ala Arg Asp Glu Gly Leu Gln Ser Tyr Glu Val Pro Arg Asp Phe
            595                 600                 605

Ile Ile Glu Thr Asp Pro Phe Thr Val Glu Asn Gly Leu Leu Ser Asp
            610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Ala Met Leu Gly Ala Ser Ala Ala Glu Ile Lys
            675                 680                 685

Pro Asp Ala His Phe Thr Asp Leu Gly Gly Asp Ser Leu Ser Ala Leu
            690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
            755                 760                 765

Asp Lys Phe Ile Asp Glu Gln Thr Leu Glu Ala Lys His Leu Pro
770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
                820                 825                 830

Ala Lys Ala Arg Leu Asp Ala Tyr Glu Ser Gly Asp Pro Lys Leu
            835                 840                 845

Ala Gly His Tyr Gln Asp Leu Ala Ala Thr Thr Leu Glu Val Leu Ala
850                 855                 860

Gly Asp Phe Ser Glu Pro Arg Leu Gly Leu Asp Glu Ala Thr Trp Asn
```

Arg Leu Ala Asp Glu Val Asp Phe Ile Ser His Pro Gly Ala Leu Val
            865                 870                 875                 880

Asn His Val Leu Pro Tyr Asn Gln Leu Phe Gly Pro Asn Val Ala Gly
            885                 890                 895

Val Ala Glu Ile Ile Lys Leu Ala Ile Thr Thr Arg Ile Lys Pro Val
            900                 905                 910

Thr Tyr Leu Ser Thr Val Ala Ala Gly Val Glu Pro Ser Ala
            915                 920                 925

930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
            965                 970                 975

Val Leu Leu Arg Glu Ala His Asp Arg Thr Gly Leu Pro Val Arg Val
            980                 985                 990

Phe Arg Ser Asp Met Ile Leu Ala His Gln Lys Tyr Thr Gly Gln Val
            995                 1000                1005

Asn Ala Thr Asp Gln Phe Thr Arg Leu Val Gln Ser Leu Leu Ala Thr
     1010                1015                1020

Gly Leu Ala Pro Lys Ser Phe Tyr Glu Leu Asp Ala Gln Gly Asn Arg
1025                1030                1035                1040

Gln Arg Ala His Tyr Asp Gly Ile Pro Val Asp Phe Thr Ala Glu Ser
            1045                1050                1055

Ile Thr Thr Leu Gly Gly Asp Gly Leu Glu Gly Tyr Arg Ser Tyr Asn
            1060                1065                1070

Val Phe Asn Pro His Arg Asp Gly Val Gly Leu Asp Glu Phe Val Asp
            1075                1080                1085

Trp Leu Ile Glu Ala Gly His Pro Ile Thr Arg Ile Ala Asp Tyr Asp
            1090                1095                1100

Gln Trp Leu Ser Arg Phe Glu Thr Ser Leu Arg Gly Leu Pro Glu Ser
1105                1110                1115                1120

Lys Arg Gln Ala Ser Val Leu Pro Leu Leu His Ala Phe Ala Arg Pro
            1125                1130                1135

Gly Pro Ala Val Asp Gly Ser Pro Phe Arg Asn Thr Val Phe Arg Thr
            1140                1145                1150

Asp Val Gln Lys Ala Lys Ile Gly Ala Glu His Asp Ile Pro His Leu
            1155                1160                1165

Gly Lys Ala Leu Val Leu Lys Tyr Ala Asp Asp Ile Lys Gln Leu Gly
            1170                1175                1180

Leu Leu
1185

<210> SEQ ID NO 13
<211> LENGTH: 459
<212> TYPE: PRT
<213> ORGANISM: Chromobacterium violaceum

<400> SEQUENCE: 13

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

-continued

```
Gly Asn Lys Ile Ile Asp Gly Met Ala Gly Leu Trp Cys Val Asn Val
 50                  55                  60
Gly Tyr Gly Arg Lys Asp Phe Ala Glu Ala Arg Arg Gln Met Glu
 65                  70                  75                  80
Glu Leu Pro Phe Tyr Asn Thr Phe Phe Lys Thr Thr His Pro Ala Val
                 85                  90                  95
Val Glu Leu Ser Ser Leu Leu Ala Glu Val Thr Pro Ala Gly Phe Asp
            100                 105                 110
Arg Val Phe Tyr Thr Asn Ser Gly Ser Glu Ser Val Asp Thr Met Ile
            115                 120                 125
Arg Met Val Arg Arg Tyr Trp Asp Val Gln Gly Lys Pro Glu Lys Lys
130                 135                 140
Thr Leu Ile Gly Arg Trp Asn Gly Tyr His Gly Ser Thr Ile Gly Gly
145                 150                 155                 160
Ala Ser Leu Gly Gly Met Lys Tyr Met His Glu Gln Gly Asp Leu Pro
                165                 170                 175
Ile Pro Gly Met Ala His Ile Glu Gln Pro Trp Trp Tyr Lys His Gly
            180                 185                 190
Lys Asp Met Thr Pro Asp Glu Phe Gly Val Val Ala Ala Arg Trp Leu
            195                 200                 205
Glu Glu Lys Ile Leu Glu Ile Gly Ala Asp Lys Val Ala Ala Phe Val
210                 215                 220
Gly Glu Pro Ile Gln Gly Ala Gly Gly Val Ile Val Pro Pro Ala Thr
225                 230                 235                 240
Tyr Trp Pro Glu Ile Glu Arg Ile Cys Arg Lys Tyr Asp Val Leu Leu
                245                 250                 255
Val Ala Asp Glu Val Ile Cys Gly Phe Gly Arg Thr Gly Glu Trp Phe
            260                 265                 270
Gly His Gln His Phe Gly Phe Gln Pro Asp Leu Phe Thr Ala Ala Lys
            275                 280                 285
Gly Leu Ser Ser Gly Tyr Leu Pro Ile Gly Ala Val Phe Val Gly Lys
290                 295                 300
Arg Val Ala Glu Gly Leu Ile Ala Gly Gly Asp Phe Asn His Gly Phe
305                 310                 315                 320
Thr Tyr Ser Gly His Pro Val Cys Ala Ala Val Ala His Ala Asn Val
                325                 330                 335
Ala Ala Leu Arg Asp Glu Gly Ile Val Gln Arg Val Lys Asp Asp Ile
            340                 345                 350
Gly Pro Tyr Met Gln Lys Arg Trp Arg Glu Thr Phe Ser Arg Phe Glu
            355                 360                 365
His Val Asp Asp Val Arg Gly Val Gly Met Val Gln Ala Phe Thr Leu
370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Arg
                405                 410                 415
Ala Cys Gly Asp His Ile Val Ser Ala Pro Pro Leu Val Met Thr Arg
            420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
450                 455
```

```
<210> SEQ ID NO 14
<211> LENGTH: 468
<212> TYPE: PRT
<213> ORGANISM: Pseudomonas aeruginosa

<400> SEQUENCE: 14
```

| | | | | | | | | | | | | | | |
|---|---|---|---|---|---|---|---|---|---|---|---|---|---|---|
| Met | Asn | Ala | Arg | Leu | His | Ala | Thr | Ser | Pro | Leu | Gly | Asp | Ala | Asp | Leu |
| 1 | | | | 5 | | | | | 10 | | | | | 15 | |

Val Arg Ala Asp Gln Ala His Tyr Met His Gly Tyr His Val Phe Asp
          20                  25                  30

Asp His Arg Val Asn Gly Ser Leu Asn Ile Ala Ala Gly Asp Gly Ala
              35                  40                  45

Tyr Ile Tyr Asp Thr Ala Gly Asn Arg Tyr Leu Asp Ala Val Gly Gly
 50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                  85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
370                 375                 380

```
Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
            405                 410                 415

Ala Gln Lys Arg Gly Leu Leu Val Arg Pro Ile Val His Leu Asn Val
        420                 425                 430

Met Ser Pro Pro Leu Ile Leu Thr Arg Glu Gln Val Asp Thr Val Val
    435                 440                 445

Arg Val Leu Arg Glu Ser Ile Glu Glu Thr Val Glu Asp Leu Val Arg
450                 455                 460

Ala Gly His Arg
465

<210> SEQ ID NO 15
<211> LENGTH: 454
<212> TYPE: PRT
<213> ORGANISM: Pseudomonas syringae

<400> SEQUENCE: 15

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190

Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Gly Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285
```

Lys Gly Leu Thr Ser Gly Tyr Val Pro Met Gly Gly Leu Ile Val Arg
            290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
            355                 360                 365

Leu Val Gly Glu Val Arg Gly Val Gly Leu Leu Gly Ala Ile Glu Leu
            370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
                420                 425                 430

Gln Ile Asp Glu Leu Val Glu Lys Ala Arg Thr Cys Leu Asp Leu Thr
            435                 440                 445

Leu Ala Val Leu Gln Gly
    450

<210> SEQ ID NO 16
<211> LENGTH: 467
<212> TYPE: PRT
<213> ORGANISM: Rhodobacter sphaeroides

<400> SEQUENCE: 16

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu

```
                195                 200                 205
Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465

<210> SEQ ID NO 17
<211> LENGTH: 459
<212> TYPE: PRT
<213> ORGANISM: Escherichia coli

<400> SEQUENCE: 17

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95
```

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
            165                 170                 175

Ser Gly Ala Phe His Gly Lys Ser Leu Gly Ala Leu Ser Ala Thr Ala
        180                 185                 190

Lys Ser Thr Phe Arg Lys Pro Phe Met Pro Leu Leu Pro Gly Phe Arg
    195                 200                 205

His Val Pro Phe Gly Asn Ile Glu Ala Met Arg Thr Ala Leu Asn Glu
            210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
            245                 250                 255

Val Arg Lys Leu Cys Asp Glu Phe Gly Ala Leu Met Ile Leu Asp Glu
        260                 265                 270

Val Gln Thr Gly Met Gly Arg Thr Gly Lys Met Phe Ala Cys Glu His
    275                 280                 285

Glu Asn Val Gln Pro Asp Ile Leu Cys Leu Ala Lys Ala Leu Gly Gly
            290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Phe Gly Gly Asn
            325                 330                 335

Pro Leu Ala Cys Ala Ala Ala Leu Ala Thr Ile Asn Val Leu Leu Glu
        340                 345                 350

Gln Asn Leu Pro Ala Gln Ala Glu Gln Lys Gly Asp Met Leu Leu Asp
    355                 360                 365

Gly Phe Arg Gln Leu Ala Arg Glu Tyr Pro Asp Leu Val Gln Glu Ala
370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
            405                 410                 415

Gly Thr Leu Asn Asn Ala Lys Thr Ile Arg Ile Glu Pro Pro Leu Thr
        420                 425                 430

Leu Thr Ile Glu Gln Cys Glu Leu Val Ile Lys Ala Ala Arg Lys Ala
    435                 440                 445

Leu Ala Ala Met Arg Val Ser Val Glu Glu Ala
        450                 455

<210> SEQ ID NO 18
<211> LENGTH: 453
<212> TYPE: PRT
<213> ORGANISM: Vibrio Fluvialis

<400> SEQUENCE: 18

Met Asn Lys Pro Gln Ser Trp Glu Ala Arg Ala Glu Thr Tyr Ser Leu
1               5                   10                  15

-continued

```
Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430
```

```
Gln Met Asp Glu Met Phe Asp Lys Leu Glu Lys Ala Leu Asp Lys Val
            435                 440                 445
Phe Ala Glu Val Ala
        450
```

<210> SEQ ID NO 19
<211> LENGTH: 224
<212> TYPE: PRT
<213> ORGANISM: Bacillus subtilis

<400> SEQUENCE: 19

```
Met Lys Ile Tyr Gly Ile Tyr Met Asp Arg Pro Leu Ser Gln Glu Glu
 1               5                  10                  15
Asn Glu Arg Phe Met Ser Phe Ile Ser Pro Glu Lys Arg Glu Lys Cys
                20                  25                  30
Arg Arg Phe Tyr His Lys Glu Asp Ala His Arg Thr Leu Leu Gly Asp
            35                  40                  45
Val Leu Val Arg Ser Val Ile Ser Arg Gln Tyr Gln Leu Asp Lys Ser
        50                  55                  60
Asp Ile Arg Phe Ser Thr Gln Glu Tyr Gly Lys Pro Cys Ile Pro Asp
 65                  70                  75                  80
Leu Pro Asp Ala His Phe Asn Ile Ser His Ser Gly Arg Trp Val Ile
                85                  90                  95
Cys Ala Phe Asp Ser Gln Pro Ile Gly Ile Asp Ile Glu Lys Thr Lys
            100                 105                 110
Pro Ile Ser Leu Glu Ile Ala Lys Arg Phe Phe Ser Lys Thr Glu Tyr
        115                 120                 125
Ser Asp Leu Leu Ala Lys Asp Lys Asp Glu Gln Thr Asp Tyr Phe Tyr
    130                 135                 140
His Leu Trp Ser Met Lys Glu Ser Phe Ile Lys Gln Glu Gly Lys Gly
145                 150                 155                 160
Leu Ser Leu Pro Leu Asp Ser Phe Ser Val Arg Leu His Gln Asp Gly
                165                 170                 175
Gln Val Ser Ile Glu Leu Pro Asp Ser His Ser Pro Cys Tyr Ile Lys
            180                 185                 190
Thr Tyr Glu Val Asp Pro Gly Tyr Lys Met Ala Val Cys Ala Ala His
        195                 200                 205
Pro Asp Phe Pro Glu Asp Ile Thr Met Val Ser Tyr Glu Glu Leu Leu
    210                 215                 220
```

<210> SEQ ID NO 20
<211> LENGTH: 222
<212> TYPE: PRT
<213> ORGANISM: Nocardia sp. NRRL 5646

<400> SEQUENCE: 20

```
Met Ile Glu Thr Ile Leu Pro Ala Gly Val Glu Ser Ala Glu Leu Leu
 1               5                  10                  15
Glu Tyr Pro Glu Asp Leu Lys Ala His Pro Ala Glu Glu His Leu Ile
                20                  25                  30
Ala Lys Ser Val Glu Lys Arg Arg Arg Asp Phe Ile Gly Ala Arg His
            35                  40                  45
Cys Ala Arg Leu Ala Leu Ala Glu Leu Gly Glu Pro Pro Val Ala Ile
        50                  55                  60
Gly Lys Gly Glu Arg Gly Ala Pro Ile Trp Pro Arg Gly Val Val Gly
 65                  70                  75                  80
```

```
Ser Leu Thr His Cys Asp Gly Tyr Arg Ala Ala Val Ala His Lys
             85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
130             135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220
```

<210> SEQ ID NO 21
<211> LENGTH: 286
<212> TYPE: PRT
<213> ORGANISM: Escherichia coli

<400> SEQUENCE: 21

```
Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gln Val Val Gly Gln Ala Leu Tyr Ala Ala Lys
            35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65              70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
            115                 120                 125

Gly Leu Pro Ser Glu Thr Gln Ile Ala Gln Ser Leu Ala His Leu Leu
        130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240
```

-continued

Leu Asn Glu Trp Leu Leu Tyr Ser Val Glu Ser Thr Ser Ala Ser Ser
            245                 250                 255

Ala Arg Gly Phe Val Arg Gly Glu Phe Tyr Thr Gln Asp Gly Val Leu
        260                 265                 270

Val Ala Ser Thr Val Gln Glu Gly Val Met Arg Asn His Asn
        275                 280                 285

<210> SEQ ID NO 22
<211> LENGTH: 561
<212> TYPE: PRT
<213> ORGANISM: Escherichia coli

<400> SEQUENCE: 22

Met Lys Lys Val Trp Leu Asn Arg Tyr Pro Ala Asp Val Pro Thr Glu
 1               5                  10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
 50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
    130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro

```
                325                 330                 335
Val Gln Gln Val Val Ala Glu Arg Trp Val Lys Leu Thr Gly Gln Tyr
            340                 345                 350
Leu Leu Glu Gly Tyr Gly Leu Thr Glu Cys Ala Pro Leu Val Ser Val
            355                 360                 365
Asn Pro Tyr Asp Ile Asp Tyr His Ser Gly Ser Ile Gly Leu Pro Val
370                 375                 380
Pro Ser Thr Glu Ala Lys Leu Val Asp Asp Asp Asn Glu Val Pro
385                 390                 395                 400
Pro Gly Gln Pro Gly Glu Leu Cys Val Lys Gly Pro Gln Val Met Leu
                405                 410                 415
Gly Tyr Trp Gln Arg Pro Asp Ala Thr Asp Glu Ile Ile Lys Asn Gly
            420                 425                 430
Trp Leu His Thr Gly Asp Ile Ala Val Met Asp Glu Glu Gly Phe Leu
            435                 440                 445
Arg Ile Val Asp Arg Lys Lys Asp Met Ile Leu Val Ser Gly Phe Asn
450                 455                 460
Val Tyr Pro Asn Glu Ile Glu Asp Val Val Met Gln His Pro Gly Val
465                 470                 475                 480
Gln Glu Val Ala Ala Val Gly Val Pro Ser Gly Ser Gly Glu Ala
                485                 490                 495
Val Lys Ile Phe Val Val Lys Lys Asp Pro Ser Leu Thr Glu Glu Ser
                500                 505                 510
Leu Val Thr Phe Cys Arg Arg Gln Leu Thr Gly Tyr Lys Val Pro Lys
            515                 520                 525
Leu Val Glu Phe Arg Asp Glu Leu Pro Lys Ser Asn Val Gly Lys Ile
            530                 535                 540
Leu Arg Arg Glu Leu Arg Asp Glu Ala Arg Gly Lys Val Asp Asn Lys
545                 550                 555                 560
Ala

<210> SEQ ID NO 23
<211> LENGTH: 515
<212> TYPE: PRT
<213> ORGANISM: Cupriavidus necator

<400> SEQUENCE: 23

Met His Pro His Ile His Ala Gln Arg Thr Pro Glu Lys Pro Ala Val
1               5                   10                  15
Ile Met Gly Gly Ser Gly Ala Val Val Thr Tyr Arg Glu Leu Asp Glu
                20                  25                  30
Arg Ser Asn Gln Val Ala His Leu Phe Arg Ser Gln Gly Leu Gln Pro
            35                  40                  45
Gly Asp Arg Val Ala Phe Met Val Glu Asn His Pro Arg Leu Phe Glu
50                  55                  60
Leu Cys Trp Gly Ala Gln Arg Ser Gly Ile Val Tyr Val Cys Leu Ser
65                  70                  75                  80
Thr Arg Leu Asn Val Ala Asp Ala Ala His Ile Ile Asn Asp Ser Gly
                85                  90                  95
Ala Arg Leu Leu Val Thr His Ala Gln Ala Glu Val Ala Ala Ala
                100                 105                 110
Leu Ala Gly Gln Thr Pro Ala Leu Arg Gly Arg Leu Met Leu Asp Gly
            115                 120                 125
Thr Met Pro Gly Tyr Asp Ala Tyr Glu Thr Ala Leu Ala Arg Cys Pro
```

```
            130                 135                 140
Ala Thr Arg Ile Asp Asp Glu Val Thr Gly Gly Asp Met Leu Tyr Ser
145                 150                 155                 160

Ser Gly Thr Thr Gly Arg Pro Lys Gly Val Tyr Ala Pro Ser Ser
                165                 170                 175

Pro Asn Ile Asp Asp Pro Thr Thr Leu Thr Ser Leu Cys Gln Arg Leu
            180                 185                 190

Tyr Gly Phe Asp Ala Glu Thr Arg Tyr Leu Ser Pro Ala Pro Leu Tyr
        195                 200                 205

His Ala Ala Pro Leu Arg Tyr Asn Met Thr Val Gln Ala Leu Gly Gly
    210                 215                 220

Thr Ala Val Val Met Glu His Phe Asp Ala Glu His Tyr Leu Gln Leu
225                 230                 235                 240

Val Gln Gln His Arg Ile Thr His Thr Gln Leu Val Pro Thr Met Phe
                245                 250                 255

Ser Arg Met Leu Lys Leu Pro Glu Ala Gln Arg Gln Ala Tyr Asp Val
            260                 265                 270

Ser Ser Leu Arg Val Ala Ile His Ala Ala Pro Cys Pro Val Gln
        275                 280                 285

Val Lys Glu Ala Met Ile Ala Trp Trp Gly Pro Val Ile Trp Glu Tyr
    290                 295                 300

Tyr Ala Gly Thr Glu Gly Asn Gly Val Thr Val Val Ser Thr Pro Glu
305                 310                 315                 320

Trp Leu Glu Arg Lys Gly Thr Val Gly Arg Ala Met Val Gly Lys Leu
                325                 330                 335

Arg Ile Cys Gly Pro Asp Gly Ala Leu Leu Pro Pro Gly Glu Ser Gly
            340                 345                 350

Thr Ile Tyr Phe Ala Glu Gly Arg Asp Phe Ser Tyr His Asn Asp Glu
        355                 360                 365

Ala Lys Thr Ala Glu Ser Arg His Pro Gln Gln Pro Asp Trp Ser Thr
    370                 375                 380

Ile Gly Asp Val Gly Tyr Val Asp Ala Asp Gly Tyr Leu Tyr Leu Thr
385                 390                 395                 400

Asp Arg Lys Ala Asn Met Ile Ile Ser Gly Gly Val Asn Ile Tyr Pro
                405                 410                 415

Gln Glu Ala Glu Asn Leu Leu Met Thr His Pro Lys Val Met Asp Val
            420                 425                 430

Ala Val Ile Gly Val Pro Asn Glu Asp Phe Gly Glu Glu Val Lys Ala
        435                 440                 445

Val Val Gln Pro Val Asp Met Ser Gln Ala Gly Pro Glu Leu Ala Ala
    450                 455                 460

Glu Leu Ile Ala Phe Cys Arg Ala Asn Leu Ser Ala Ile Lys Cys Pro
465                 470                 475                 480

Arg Ser Val Asp Phe Ala Ser Glu Leu Pro Arg Leu Pro Thr Gly Lys
                485                 490                 495

Leu Leu Lys Arg Leu Leu Arg Asp Arg Tyr Trp Gly Gly His Ala Asn
            500                 505                 510

Lys Leu Val
        515

<210> SEQ ID NO 24
<211> LENGTH: 320
<212> TYPE: PRT
<213> ORGANISM: Acidaminococcus fermentans
```

<400> SEQUENCE: 24

```
Met Ser Lys Val Met Thr Leu Lys Asp Ala Ile Ala Lys Tyr Val His
1               5                   10                  15

Ser Gly Asp His Ile Ala Leu Gly Gly Phe Thr Thr Asp Arg Lys Pro
            20                  25                  30

Tyr Ala Ala Val Phe Glu Ile Leu Arg Gln Gly Ile Thr Asp Leu Thr
        35                  40                  45

Gly Leu Gly Gly Ala Ala Gly Asp Trp Asp Met Leu Ile Gly Asn
    50                  55                  60

Gly Arg Val Lys Ala Tyr Ile Asn Cys Tyr Thr Ala Asn Ser Gly Val
65                  70                  75                  80

Thr Asn Val Ser Arg Arg Phe Arg Lys Trp Phe Glu Ala Gly Lys Leu
                85                  90                  95

Thr Met Glu Asp Tyr Ser Gln Asp Val Ile Tyr Met Met Trp His Ala
            100                 105                 110

Ala Ala Leu Gly Leu Pro Phe Leu Pro Val Thr Leu Met Gln Gly Ser
        115                 120                 125

Gly Leu Thr Asp Glu Trp Gly Ile Ser Lys Glu Val Arg Lys Thr Leu
    130                 135                 140

Asp Lys Val Pro Asp Asp Lys Phe Lys Tyr Ile Asp Asn Pro Phe Lys
145                 150                 155                 160

Pro Gly Glu Lys Val Val Ala Val Pro Val Pro Gln Val Asp Val Ala
                165                 170                 175

Ile Ile His Ala Gln Gln Ala Ser Pro Asp Gly Thr Val Arg Ile Trp
            180                 185                 190

Gly Gly Lys Phe Gln Asp Val Asp Ile Ala Glu Ala Lys Tyr Thr
        195                 200                 205

Ile Val Thr Cys Glu Glu Ile Ile Ser Asp Glu Glu Ile Arg Arg Asp
210                 215                 220

Pro Thr Lys Asn Asp Ile Pro Gly Met Cys Val Asp Ala Val Val Leu
225                 230                 235                 240

Ala Pro Tyr Gly Ala His Pro Ser Gln Cys Tyr Gly Leu Tyr Asp Tyr
                245                 250                 255

Asp Asn Pro Phe Leu Lys Val Tyr Asp Lys Val Ser Lys Thr Gln Glu
            260                 265                 270

Asp Phe Asp Ala Phe Cys Lys Glu Trp Val Phe Asp Leu Lys Asp His
        275                 280                 285

Asp Glu Tyr Leu Asn Lys Leu Gly Ala Thr Arg Leu Ile Asn Leu Lys
    290                 295                 300

Val Val Pro Gly Leu Gly Tyr His Ile Asp Met Thr Lys Glu Asp Lys
305                 310                 315                 320
```

<210> SEQ ID NO 25
<211> LENGTH: 266
<212> TYPE: PRT
<213> ORGANISM: Acidaminococcus fermentans

<400> SEQUENCE: 25

```
Met Ala Asp Tyr Thr Asn Tyr Thr Asn Lys Glu Met Gln Ala Val Thr
1               5                   10                  15

Ile Ala Lys Gln Ile Lys Asn Gly Gln Val Val Thr Val Gly Thr Gly
            20                  25                  30

Leu Pro Leu Ile Gly Ala Ser Val Ala Lys Arg Val Tyr Ala Pro Asp
        35                  40                  45
```

```
Cys His Ile Ile Val Glu Ser Gly Leu Met Asp Cys Ser Pro Val Glu
        50                  55                  60

Val Pro Arg Ser Val Gly Asp Leu Arg Phe Met Ala His Cys Gly Cys
 65                  70                  75                  80

Ile Trp Pro Asn Val Arg Phe Val Gly Phe Glu Ile Asn Glu Tyr Leu
                85                  90                  95

His Lys Ala Asn Arg Leu Ile Ala Phe Ile Gly Gly Ala Gln Ile Asp
            100                 105                 110

Pro Tyr Gly Asn Val Asn Ser Thr Ser Ile Gly Asp Tyr His His Pro
        115                 120                 125

Lys Thr Arg Phe Thr Gly Ser Gly Gly Ala Asn Gly Ile Ala Thr Tyr
130                 135                 140

Ser Asn Thr Ile Ile Met Met Gln His Glu Lys Arg Arg Phe Met Asn
145                 150                 155                 160

Lys Ile Asp Tyr Val Thr Ser Pro Gly Trp Ile Asp Gly Pro Gly Gly
                165                 170                 175

Arg Glu Arg Leu Gly Leu Pro Gly Asp Val Gly Pro Gln Leu Val Val
            180                 185                 190

Thr Asp Lys Gly Ile Leu Lys Phe Asp Glu Lys Thr Lys Arg Met Tyr
        195                 200                 205

Leu Ala Ala Tyr Tyr Pro Thr Ser Ser Pro Glu Asp Val Leu Glu Asn
210                 215                 220

Thr Gly Phe Asp Leu Asp Val Ser Lys Ala Val Glu Leu Glu Ala Pro
225                 230                 235                 240

Asp Pro Ala Val Ile Lys Leu Ile Arg Glu Glu Ile Asp Pro Gly Gln
                245                 250                 255

Ala Phe Ile Gln Val Pro Thr Glu Ala Lys
            260                 265

<210> SEQ ID NO 26
<211> LENGTH: 397
<212> TYPE: PRT
<213> ORGANISM: Treponema denticola

<400> SEQUENCE: 26

Met Ile Val Lys Pro Met Val Arg Asn Asn Ile Cys Leu Asn Ala His
 1               5                  10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
 50                  55                  60

Thr Ala Ala Phe Gly Tyr Gly Ala Ala Thr Ile Gly Val Ser Phe Glu
 65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
```

```
                145                 150                 155                 160
Val Leu Lys Pro Phe Gly Lys Thr Phe Thr Gly Lys Thr Val Asp Pro
                    165                 170                 175

Phe Thr Gly Glu Leu Lys Glu Ile Ser Ala Glu Pro Ala Asn Asp Glu
                    180                 185                 190

Glu Ala Ala Thr Val Lys Val Met Gly Gly Glu Asp Trp Glu Arg
                    195                 200                 205

Trp Ile Lys Gln Leu Ser Lys Glu Gly Leu Leu Glu Glu Gly Cys Ile
    210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                    245                 250                 255

His Arg Leu Asn Lys Glu Asn Pro Ser Ile Arg Ala Phe Val Ser Val
                    260                 265                 270

Asn Lys Gly Leu Val Thr Arg Ala Ser Ala Val Ile Pro Val Ile Pro
                    275                 280                 285

Leu Tyr Leu Ala Ser Leu Phe Lys Val Met Lys Glu Lys Gly Asn His
    290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Asn Arg Ile Arg Ile
                    325                 330                 335

Asp Asp Trp Glu Leu Glu Glu Asp Val Gln Lys Ala Val Ser Ala Leu
                    340                 345                 350

Met Glu Lys Val Thr Gly Glu Asn Ala Glu Ser Leu Thr Asp Leu Ala
                    355                 360                 365

Gly Tyr Arg His Asp Phe Leu Ala Ser Asn Gly Phe Asp Val Glu Gly
                    370                 375                 380

Ile Asn Tyr Glu Ala Glu Val Glu Arg Phe Asp Arg Ile
385                 390                 395

<210> SEQ ID NO 27
<211> LENGTH: 539
<212> TYPE: PRT
<213> ORGANISM: Euglena gracilis

<400> SEQUENCE: 27

Met Ser Cys Pro Ala Ser Pro Ser Ala Ala Val Val Ser Ala Gly Ala
1               5                   10                  15

Leu Cys Leu Cys Val Ala Thr Val Leu Ala Thr Gly Ser Asn Pro
                20                  25                  30

Thr Ala Leu Ser Thr Ala Ser Thr Arg Ser Pro Thr Ser Leu Val Arg
                35                  40                  45

Gly Val Asp Arg Gly Leu Met Arg Pro Thr Thr Ala Ala Ala Leu Thr
            50                  55                  60

Thr Met Arg Glu Val Pro Gln Met Ala Glu Gly Phe Ser Gly Glu Ala
65                  70                  75                  80

Thr Ser Ala Trp Ala Ala Ala Gly Pro Gln Trp Ala Ala Pro Leu Val
                    85                  90                  95

Ala Ala Ala Ser Ser Ala Leu Ala Leu Trp Trp Trp Ala Ala Arg Arg
                100                 105                 110

Ser Val Arg Arg Pro Leu Ala Ala Leu Ala Glu Leu Pro Thr Ala Val
                115                 120                 125
```

```
Thr His Leu Ala Pro Pro Met Ala Met Phe Thr Thr Thr Ala Lys Val
    130                 135                 140
Ile Gln Pro Lys Ile Arg Gly Phe Ile Cys Thr Thr His Pro Ile
145                 150                 155                 160
Gly Cys Glu Lys Arg Val Gln Glu Ile Ala Tyr Ala Arg Ala His
                165                 170                 175
Pro Pro Thr Ser Pro Gly Pro Lys Arg Val Leu Val Ile Gly Cys Ser
            180                 185                 190
Thr Gly Tyr Gly Leu Ser Thr Arg Ile Thr Ala Ala Phe Gly Tyr Gln
                195                 200                 205
Ala Ala Thr Leu Gly Val Phe Leu Ala Gly Pro Pro Thr Lys Gly Arg
    210                 215                 220
Pro Ala Ala Gly Trp Tyr Asn Thr Val Ala Phe Glu Lys Ala Ala
225                 230                 235                 240
Leu Glu Ala Gly Leu Tyr Ala Arg Ser Leu Asn Gly Asp Ala Phe Asp
                245                 250                 255
Ser Thr Thr Lys Ala Arg Thr Val Glu Ala Ile Lys Arg Asp Leu Gly
                260                 265                 270
Thr Val Asp Leu Val Val Tyr Ser Ile Ala Ala Pro Lys Arg Thr Asp
    275                 280                 285
Pro Ala Thr Gly Val Leu His Lys Ala Cys Leu Lys Pro Ile Gly Ala
    290                 295                 300
Thr Tyr Thr Asn Arg Thr Val Asn Thr Asp Lys Ala Glu Val Thr Asp
305                 310                 315                 320
Val Ser Ile Glu Pro Ala Ser Pro Glu Glu Ile Ala Asp Thr Val Lys
                325                 330                 335
Val Met Gly Gly Glu Asp Trp Glu Leu Trp Ile Gln Ala Leu Ser Glu
                340                 345                 350
Ala Gly Val Leu Ala Glu Gly Ala Lys Thr Val Ala Tyr Ser Tyr Ile
                355                 360                 365
Gly Pro Glu Met Thr Trp Pro Val Tyr Trp Ser Gly Thr Ile Gly Glu
                370                 375                 380
Ala Lys Lys Asp Val Glu Lys Ala Ala Lys Arg Ile Thr Gln Gln Tyr
385                 390                 395                 400
Gly Cys Pro Ala Tyr Pro Val Val Ala Lys Ala Leu Val Thr Gln Ala
                405                 410                 415
Ser Ser Ala Ile Pro Val Val Pro Leu Tyr Ile Cys Leu Leu Tyr Arg
                420                 425                 430
Val Met Lys Glu Lys Gly Thr His Glu Gly Cys Ile Glu Gln Met Val
                435                 440                 445
Arg Leu Leu Thr Thr Lys Leu Tyr Pro Glu Asn Gly Ala Pro Ile Val
    450                 455                 460
Asp Glu Ala Gly Arg Val Arg Val Asp Asp Trp Glu Met Ala Glu Asp
465                 470                 475                 480
Val Gln Gln Ala Val Lys Asp Leu Trp Ser Gln Val Ser Thr Ala Asn
                485                 490                 495
Leu Lys Asp Ile Ser Asp Phe Ala Gly Tyr Gln Thr Glu Phe Leu Arg
                500                 505                 510
Leu Phe Gly Phe Gly Ile Asp Gly Val Asp Tyr Asp Gln Pro Val Asp
                515                 520                 525
Val Glu Ala Asp Leu Pro Ser Ala Ala Gln Gln
    530                 535
```

```
<210> SEQ ID NO 28
<211> LENGTH: 132
<212> TYPE: PRT
<213> ORGANISM: Escherichia coli

<400> SEQUENCE: 28

Met Ser Thr Thr His Asn Val Pro Gln Gly Asp Leu Val Leu Arg Thr
 1               5                  10                  15

Leu Ala Met Pro Ala Asp Thr Asn Ala Asn Gly Asp Ile Phe Gly Gly
            20                  25                  30

Trp Leu Met Ser Gln Met Asp Ile Gly Gly Ala Ile Leu Ala Lys Glu
        35                  40                  45

Ile Ala His Gly Arg Val Val Thr Val Arg Val Glu Gly Met Thr Phe
    50                  55                  60

Leu Arg Pro Val Ala Val Gly Asp Val Val Cys Cys Tyr Ala Arg Cys
65                  70                  75                  80

Val Gln Lys Gly Thr Thr Ser Val Ser Ile Asn Ile Glu Val Trp Val
                85                  90                  95

Lys Lys Val Ala Ser Glu Pro Ile Gly Gln Arg Tyr Lys Ala Thr Glu
            100                 105                 110

Ala Leu Phe Lys Tyr Val Ala Val Asp Pro Glu Gly Lys Pro Arg Ala
        115                 120                 125

Leu Pro Val Glu
    130
```

METHODS, REAGENTS AND CELLS FOR BIOSYNTHESIZING COMPOUNDS

CROSS-REFERENCE TO RELATED APPLICATIONS

This application claims the benefit of U.S. Application Nos. 62/012,674 and 62/012,735, both of which were filed on Jun. 16, 2014, the disclosures of which are incorporated by reference herein in their entireties.

TECHNICAL FIELD

This invention relates to methods of shielding a carbon chain aliphatic backbone, functionalized with terminal carboxyl groups, in a recombinant host using a polypeptide having the activity of a fatty acid O-methyltransferase. This invention also relates to methods for biosynthesizing 2,3-dehydroadipyl-CoA methyl ester in a host using one or more of: (i) a polypeptide having fatty acid O-methyltransferase activity (ii) a polypeptide having thioesterase activity or CoA-transferase activity, or (iii) a polypeptide having CoA ligase activity, and to recombinant host cells expressing one or more such exogenous enzymes. This invention also relates to methods for enzymatically converting 2,3-dehydroadipyl-CoA methyl ester to adipyl-CoA using a polypeptide having trans-enoyl-CoA reductase activity and/or a polypeptide having pimeloyl-[acp] methyl ester esterase activity, and recombinant host cells that express one or more such exogenous enzymes. In addition, the invention also relates to enzymatically converting adipyl-CoA to one or more of adipic acid, 6-aminohexanoic acid, hexamethylenediamine, caprolactam, 6-hydroxyhexanoate, and 1,6-hexanediol (hereafter "C6 building blocks") and recombinant hosts that produce such C6 building blocks.

BACKGROUND

Nylons are polyamides which are sometimes synthesized by the condensation polymerisation of a diamine with a dicarboxylic acid. Similarly, nylons may be produced by the condensation polymerisation of lactams. A ubiquitous nylon is nylon 6,6, which is produced by reaction of hexamethylenediamine (HMD) and adipic acid. Nylon 6 is produced by a ring opening polymerisation of caprolactam. Therefore, adipic acid, hexamethylenediamine and caprolactam are important intermediates in the production of nylons (Anton & Baird, Polyamides Fibers, Encyclopedia of Polymer Science and Technology, 2001).

Industrially, adipic acid and caprolactam are produced via air oxidation of cyclohexane. The air oxidation of cyclohexane produces, in a series of steps, a mixture of cyclohexanone (K) and cyclohexanol (A), designated as KA oil. Nitric acid oxidation of KA oil produces adipic acid (Musser, Adipic acid, Ullmann's Encyclopedia of Industrial Chemistry, 2000). Caprolactam is produced from cyclohexanone via its oxime and subsequent acid rearrangement (Fuchs, Kieczka and Moran, Caprolactam, Ullmann's Encyclopedia of Industrial Chemistry, 2000).

Industrially, hexamethylenediamine (HMD) is produced by hydrocyanation of C6 Building Block to adiponitrile, followed by hydrogenation to HMD (Herzog and Smiley, Hexamethylenediamine, Ullmann's Encyclopedia of Industrial Chemistry, 2012).

Given a reliance on petrochemical feedstocks; biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

Accordingly, against this background, it is clear that there is a need for sustainable methods for producing adipic acid, caprolactam, 6-aminohexanoic acid, hexamethylenediamine and 1,6-hexanediol (hereafter "C6 building bocks") wherein the methods are biocatalyst-based (Jang et al., Biotechnology & Bioengineering, 2012, 109(10), 2437-2459).

However, no wild-type prokaryote or eukaryote naturally overproduces or excretes C6 Building Blocks to the extracellular environment. Nevertheless, the metabolism of adipic acid and caprolactam has been reported (Ramsay et al., Appl. Environ. Microbiol., 1986, 52(1), 152-156; Kulkarni and Kanekar, Current Microbiology, 1998, 37, 191-194).

The dicarboxylic acid, adipic acid, is converted efficiently as a carbon source by a number of bacteria and yeasts via β-oxidation into central metabolites. β-oxidation of adipate to 3-oxoadipate facilitates further catabolism via, for example, the ortho-cleavage pathway associated with aromatic substrate degradation. The catabolism of 3-oxoadipyl-CoA to acetyl-CoA and succinyl-CoA by several bacteria and fungi has been characterised comprehensively (Harwood and Parales, Annual Review of Microbiology, 1996, 50, 553-590). Both adipate and 6-aminohexanoate are intermediates in the catabolism of caprolactam, finally degraded via 3-oxoadipyl-CoA to central metabolites.

Potential metabolic pathways have been suggested for producing adipic acid from biomass-sugar: (1) biochemically from glucose to cis,cis muconic acid via the ortho-cleavage aromatic degradation pathway, followed by chemical catalysis to adipic acid; (2) a reversible adipic acid degradation pathway via the condensation of succinyl-CoA and acetyl-CoA; and (3) combining β-oxidation, fatty acid synthase and ω-oxidation. However, no information using these strategies has been reported (Jang et al., Biotechnology & Bioengineering, 2012, 109(10), 2437-2459).

An optimality principle states that microorganisms regulate their biochemical networks to support maximum biomass growth. Beyond the need for expressing heterologous pathways in a host organism, directing carbon flux towards C6 Building Blocks that serve as carbon sources rather than as biomass growth constituents, contradicts the optimality principle. For example, transferring the 1-butanol pathway from Clostridium species into other production strains has often fallen short by an order of magnitude compared to the production performance of native producers (Shen et al., Appl. Environ. Microbiol., 2011, 77(9), 2905-2915).

The efficient synthesis of a six carbon aliphatic backbone as central precursor is a key consideration in synthesizing C6 building blocks prior to forming terminal functional groups, such as carboxyl, amine or hydroxyl groups, on the C6 aliphatic backbone.

SUMMARY

This document is based at least in part on the discovery that it is possible to construct biochemical pathways via 2,3-dehydroadipyl-CoA methyl ester for producing a six carbon chain aliphatic backbone precursor, in which one or two functional groups. i.e., carboxyl, amine, or hydroxyl, can be formed, leading to the synthesis of adipic acid, 6-aminohexanoic acid, 6-hydroxyhexanoic acid, caprolactam, hexamethylenediamine, or 1,6-hexanediol (hereafter "C6 building blocks"). Adipic acid and adipate, 6-hydroxyhexanoic acid and 6-hydroxyhexanoate, and 6-aminohexanoic and 6-aminohexanoate are used interchangeably herein to refer to the relevant compound in any of its neutral or ionized forms, including any salt forms thereof. It is understood by those skilled in the art that the specific form will depend on pH. These pathways, metabolic engineering and cultivation strategies described herein rely on producing 2,3-dehydroadipate methyl ester from 2,3-dehydroadipate using, for example, a fatty acid O-methyltransferase and producing 2,3-dehydroadipyl-CoA methyl ester from 2,3-dehydroadipate methyl ester using, for example, a CoA ligase. Adipyl-CoA can be produced from 2,3-dehydroadipyl-CoA methyl ester using, for example, a trans-2-enoyl-CoA reductase and a pimelyl-[acp] methyl ester esterase. 2,3-dehydroadipate can be produced, for example, from (i) 2-oxoglutarate or succinyl-CoA, or (ii) from 2-oxoadipate as shown in FIGS. 1 and 2, respectively.

In the face of the optimality principle, it surprisingly has been discovered that appropriate non-natural pathways, feedstocks, host microorganisms, attenuation strategies to the host's biochemical network and cultivation strategies may be combined to efficiently produce one or more C6 building blocks.

In some embodiments, a terminal carboxyl group can be enzymatically formed using a thioesterase, an aldehyde dehydrogenase, a 7-oxoheptanoate dehydrogenase, a 6-oxohexanoate dehydrogenase, a 5-oxopentanoate dehydrogenase, a reversible CoA-ligase (e.g., a reversible succinyl-CoA-ligase), or a CoA-transferase (e.g., a glutaconate CoA-transferase). See, FIG. 3.

In some embodiments, a terminal amine group can be enzymatically formed using a ω-transaminase or a deacetylase. See, FIGS. 4, 5, and 6.

In some embodiments, a terminal hydroxyl group can be enzymatically formed using a 4-hydroxybutyrate dehydrogenase, 5-hydroxypentanoate dehydrogenase, a 6-hydroxyhexanoate dehydrogenase, or an alcohol dehydrogenase. See, FIGS. 7 and 8.

The two terminal functional groups can be the same (e.g., amine or hydroxyl) or can be different (e.g., a terminal amine and a terminal carboxyl group; or a terminal hydroxyl group and a terminal carboxyl group).

Any of the methods can be performed in a recombinant host by fermentation. The host can be subjected to a cultivation strategy under anaerobic, micro-aerobic or mixed oxygen/denitrification cultivation conditions. The host can be cultured under conditions of nutrient limitation, such as one or more of phosphate, nitrogen and oxygen. The host can be retained using a ceramic membrane to maintain a high cell density during fermentation. The final electron acceptor can be an alternative to oxygen such as nitrates.

In any of the methods, the host's tolerance to high concentrations of a C6 building block can be improved through continuous cultivation in a selective environment.

The principal carbon source fed to the fermentation can derive from biological or non-biological feedstocks. In some embodiments, the biological feedstock is, includes, or derives from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock is or derives from natural gas, syngas, $CO_2/H_2$, methanol, ethanol, benzoate, non-volatile residue (NVR) or a caustic wash waste stream from cyclohexane oxidation processes, or a terephthalic acid/isophthalic acid mixture waste stream.

This document features a recombinant host that includes at least one exogenous nucleic acid encoding (i) a fatty acid O-methyltransferase; and (ii) a thioesterase or CoA-transferase, the host producing 2,3-dehydroadipate methyl ester. The host can further include an exogenous CoA ligase, the host further producing 2,3-dehydroadipyl-CoA methyl ester. In some embodiments, the host can further include an exogenous trans-2-enoyl-CoA reductase and/or an exogenous pimeloyl-[acp] methyl ester methylesterase, and produce adipyl-CoA.

This document also features a recombinant host that includes at least one exogenous nucleic acid encoding (i) a fatty acid O-methyltransferase; and (ii) a CoA ligase, the host producing 2,3-dehydroadipyl-CoA methyl ester. Such a host further can include an exogenous thioesterase or CoA-transferase. In some embodiments, the host can further include an exogenous trans-2-enoyl-CoA reductase and/or an exogenous pimeloyl-[acp] methyl ester methylesterase, and produce adipyl-CoA.

A recombinant host producing adipyl-CoA further can include at least one exogenous nucleic acid encoding one or more of a thioesterase, an aldehyde dehydrogenase, a 7-oxoheptanoate dehydrogenase, a 6-oxohexanoate dehydrogenase, a 5-oxopentanoate dehydrogenase, a CoA-transferase, a reversible CoA-ligase (e.g., a reversible succinyl-CoA-ligase), an acetylating aldehyde dehydrogenase, or a carboxylate reductase, the host producing adipic acid or adipate semialdehyde. In any of the recombinant hosts expressing a carboxylate reductase, a phosphopantetheinyl transferase also can be expressed to enhance the activity of the carboxylate reductase.

A recombinant host producing adipate semialdehyde further can include at least one exogenous nucleic acid encoding a ω-transaminase, and further produce 6-aminohexanoate.

A recombinant host producing adipate semialdehyde further can include at least one exogenous nucleic acid encoding a 4-hydroxybutyrate dehydrogenase, a 5-hydroxypentanoate dehydrogenase or a 6-hydroxyhexanoate dehydrogenase, the host further producing 6-hydroxyhexanoic acid.

A recombinant host producing adipate semialdehyde, 6-aminohexanoate, or 6-hydroxyhexanoic acid further can include a carboxylate reductase, a ω-transaminase, a deacetylase, an N-acetyl transferase, or an alcohol dehydrogenase, the host further producing hexamethylenediamine.

A recombinant host producing 6-hydroxyhexanoic acid further can include at least one exogenous nucleic acid encoding a carboxylate reductase or an alcohol dehydrogenase, the host further producing 1,6-hexanediol.

In some embodiments, the host microorganism is a prokaryote. For example, the prokaryote can be from the bacterial genus *Escherichia* such as *Escherichia coli*; from the bacterial genus *Clostridia* such as *Clostridium ljungdahlii*, *Clostridium autoethanogenum* or *Clostridium kluyveri*; from the bacterial genus *Corynebacteria* such as *Corynebacterium glutamicum*; from the bacterial genus *Cupriavidus* such as *Cupriavidus necator* or *Cupriavidus metallidurans*; from the bacterial genus *Pseudomonas* such as *Pseudomonas fluorescens*, *Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus* such as *Lactobacillus delbrueckii*; or from the bacterial genus *Lactococcus* such as *Lactococcus lactis*. Such prokaryotes also can be a source of genes to construct recombinant host cells described herein that are capable of producing one or more C6 building blocks.

In some embodiments, the host microorganism is an eukaryote (e.g., a fungus such as a yeast). For example, the eukaryote can be from the fungus genus *Aspergillus* such as *Aspergillus niger*; from the yeast genus *Saccharomyces* such as *Saccharomyces cerevisiae*; from the yeast genus *Pichia* such as *Pichia pastoris*; from the yeast genus *Yarrowia* such as *Yarrowia lipolytica*; from the yeast genus *Issatchenkia* such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*. Such eukaryotes also can be a source of genes to construct recombinant host cells described herein that are capable of producing one or more C6 building blocks.

Any of the recombinant hosts described herein further can include one or more of the following attenuated enzymes: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, a transhydrogenase dissipating the NADPH imbalance, an glutamate dehydrogenase dissipating the NADPH imbalance, a NADH/NADPH-utilizing glutamate dehydrogenase, a pimeloyl-CoA dehydrogenase; an acyl-CoA dehydrogenase accepting C7 building blocks and central precursors as substrates; a glutaryl-CoA dehydrogenase; or a adipyl-CoA synthetase.

Any of the recombinant hosts described herein further can overexpress one or more genes encoding: an acetyl-CoA synthetase; a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a fructose 1,6 diphosphatase a L-alanine dehydrogenase; a formate dehydrogenase; a PEP carboxylase, a pyruvate carboxylase, PEP carboxykinase, PEP synthase, a L-glutamate dehydrogenase specific to the NADPH used to generate the co-factor imbalance; an alcohol oxidase, a methanol dehydrogenase, a formaldehyde dehydrogenase, a lysine transporter; a dicarboxylate transporter; an S-adenosylmethionine synthetase, a 3-phosphoglycerate dehydrogenase, a 3-phosphoserine aminotransferase, a phosphoserine phosphatase and/or a multidrug transporter.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Many of the enzymes described herein catalyze reversible reactions, and the reaction of interest may be the reverse of the described reaction. The schematic pathways shown in FIGS. 1 to 8 illustrate the reaction of interest for each of the intermediates.

In one aspect, this document features a method for producing a bioderived six carbon compound. The method for producing a bioderived six carbon compound can include culturing or growing a recombinant host as described herein under conditions and for a sufficient period of time to produce the bioderived six carbon compound, wherein, optionally, the bioderived six carbon compound is selected from the group consisting of adipic acid, adipate semialdehyde, 6-aminohexanoic acid, 6-hydroxyhexanoic acid, caprolactam, hexamethylenediamine, 1,6-hexanediol, and combinations thereof.

In one aspect, this document features composition comprising a bioderived six carbon compound as described herein and a compound other than the bioderived six carbon compound, wherein the bioderived six carbon compound is selected from the group consisting of adipic acid, adipate semialdehyde, 6-aminohexanoic acid, 6-hydroxyhexanoic acid, caprolactam, hexamethylenediamine, 1,6-hexanediol, and combinations thereof. For example, the bioderived six carbon compound can be a cellular portion of a host cell or an organism.

This document also features a biobased polymer comprising the bioderived adipic acid, adipate semialdehyde, 6-aminohexanoic acid, 6-hydroxyhexanoic acid, caprolactam, hexamethylenediamine, 1,6-hexanediol, and combinations thereof.

This document also features a biobased resin comprising the bioderived adipic acid, adipate semialdehyde, 6-aminohexanoic acid, 6-hydroxyhexanoic acid, caprolactam, hexamethylenediamine, 1,6-hexanediol, and combinations thereof, as well as a molded product obtained by molding a biobased resin.

In another aspect, this document features a process for producing a biobased polymer that includes chemically reacting the bioderived adipic acid, adipate semialdehyde, 6-aminohexanoic acid, 6-hydroxyhexanoic acid, caprolactam, hexamethylenediamine, or 1,6-hexanediol, with itself or another compound in a polymer producing reaction.

In another aspect, this document features a process for producing a biobased resin that includes chemically reacting the bioderived adipic acid, adipate semialdehyde, 6-aminohexanoic acid, 6-hydroxyhexanoic acid, caprolactam, hexamethylenediamine, or 1,6-hexanediol, with itself or another compound in a resin producing reaction.

Also, described herein is a biochemical network comprising a polypeptide having fatty acid O-methyltransferase activity, wherein the polypeptide having fatty acid O-methyltransferase activity enzymatically converts 2,3-dehydroadipic acid to 2,3-dehydroadipate methyl ester. The biochemical network can further include a polypeptide having CoA ligase activity, wherein the polypeptide having CoA ligase activity enzymatically converts 2,3-dehydroadipate methyl ester to 2,3-dehydroadipyl-CoA methyl ester. The biochemical network can further include a polypeptide having trans-2-enoyl-CoA reductase activity, wherein the polypeptide having trans-2-enoyl-CoA reductase activity enzymatically converts 2,3-dehydroadipyl-CoA methyl ester to adipyl-CoA methyl ester. The biochemical network can further include a polypeptide having pimelyl-[acp] methyl ester esterase activity, wherein the polypeptide having pimelyl-[acp] methyl ester esterase activity enzymatically converts adipyl-CoA methyl ester to adipyl-CoA.

The biochemical network can further include one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or alcohol dehydrogenase activity, wherein the one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or alcohol dehydrogenase activity enzymatically convert adipyl-CoA to a product selected from the group consisting of adipic acid, 6-aminohexanoate, 6-hydroxyhexanoate, caprolactam, hexamethylenediamine, and 1,6-hexanediol.

Also, described herein is a means for obtaining 2,3-dehydroadipyl-CoA methyl ester, 2,3-dehydroadipate methyl ester, adipic acid, 6 aminohexanoate, 6-hydroxyhexanoate, caprolactam, hexamethylenediamine, and 1,6 hexanediol using one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, carboxylate reductase, or alcohol dehydrogenase activity.

In another aspect, this document features a composition comprising one or more polypeptides having fatty acid O-methyltransferase, dehydrogenase, CoA-transferase, CoA-dehydratase, dehydratase, reductase, mutase, CoA-ligase, lyase, thioesterase, aminotransferase, hydrolase, transaminase, or N-acetyltransferase activity and at least one of 2,3-dehydroadipyl-CoA methyl ester, 2,3-dehydroadipate methyl ester, adipic acid, 6-aminohexanoic acid, caprolactam, hexamethylenediamine, 6-hydroxyhexanoic acid, and 1,6-hexanediol. The composition can be cellular.

In another aspect, this document features a bio-derived product, bio-based product or fermentation-derived product, wherein said product comprises i. a composition comprising at least one bio-derived, bio-based or fermentation-derived compound according to any one of claims 1-62, or any one of FIGS. 1-9, or any combination thereof, ii. a bio-derived, bio-based or fermentation-derived polymer comprising the bio-derived, bio-based or fermentation-derived composition or compound of i., or any combination thereof, iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof, iv. a molded substance obtained by molding the bio-derived, bio-based or fermentation-derived polymer of ii. or the bio-derived, bio-based or fermentation-derived resin of iii., or any combination thereof, v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein including GenBank and NCBI submissions with accession numbers are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIGS. 9A-9P contain the amino acid sequences of a *Mycobacterium marinum* fatty acid O-methyltransferase (GenBank Accession No. ACC41782.1; SEQ ID NO: 1), a *Mycobacterium smegmatis* str. MC2 fatty acid O-methyltransferase (GenBank Accession No. ABK73223.1; SEQ ID NO: 2), a *Pseudomonas putida* fatty acid O-methyltransferase (GenBank Accession No. CAA39234.1; SEQ ID NO: 3), a *Lactobacillus brevis* acyl-[acp] thioesterase (GenBank Accession No. ABJ63754.1, SEQ ID NO: 4), a *Lactobacillus plantarum* acyl-[acp] thioesterase (GenBank Accession No. CCC78182.1, SEQ ID NO: 5), an *Escherichia coli* pimelyl-[acp] methyl ester esterase (see GenBank Accession No. AAC76437.1, SEQ ID NO: 6), a *Mycobacterium marinum* carboxylate reductase (See Genbank Accession No. ACC40567.1, SEQ ID NO: 7), a *Mycobacterium smegmatis* carboxylate reductase (see Genbank Accession No. ABK71854.1, SEQ ID NO: 8), a *Segniliparus rugosus* carboxylate reductase (see Genbank Accession No. EFV11917.1, SEQ ID NO: 9), a *Mycobacterium smegmatis* carboxylate reductase (see Genbank Accession No. ABK75684.1, SEQ ID NO: 10), a *Mycobacterium massiliense* carboxylate reductase (see Genbank Accession No. EIV11143.1, SEQ ID NO: 11), a *Segniliparus rotundus* carboxylate reductase (see Genbank Accession No. ADG98140.1, SEQ ID NO: 12), a *Chromobacterium violaceum* ω-transaminase (see Genbank Accession No. AAQ59697.1, SEQ ID NO: 13), a *Pseudomonas aeruginosa* ω-transaminase (see Genbank Accession No. AAG08191.1, SEQ ID NO: 14), a *Pseudomonas syringae* ω-transaminase (see Genbank Accession No. AAY39893.1, SEQ ID NO: 15), a *Rhodobacter sphaeroides* ω-transaminase (see Genbank Accession No. ABA81135.1, SEQ ID NO: 16), an *Escherichia coli* ω-transaminase (see Genbank Accession No. AAA57874.1, SEQ ID NO: 17), a *Vibrio fluvialis* ω-transaminase (see Genbank Accession No. AEA39183.1, SEQ ID NO: 18), a *Bacillus subtilis* phosphopantetheinyl transferase (see Genbank Accession No. CAA44858.1, SEQ ID NO: 19), a *Nocardia* sp. NRRL 5646 phosphopantetheinyl transferase (see Genbank Accession No. ABI83656.1, SEQ ID NO: 20), an *Escherichia coli* thioesterase encoded by tesB (See GenBank Accession No. AAA24665.1, SEQ ID NO: 21), an *Escherichia coli* long-chain-fatty-acid-CoA ligase (Genbank Accession No. CAA50321.1, SEQ ID NO: 22), a *Cupriavidus necator* long-chain-fatty-acid-CoA ligase (Genbank Accession No. CAJ95550.1, SEQ ID NO: 23), an *Acidaminococcus fermentans* glutaconate CoA-transferase (see, e.g., Genbank Accession No. CAA57199.1 (GctA) and CAA57200.1 (GctB), SEQ ID NOs: 24 and 25, respectively), a *Treponema denticola* enoyl-CoA reductase (see, e.g., Genbank Accession No. AAS11092.1, SEQ ID NO: 26), and an *Euglena gracilis* enoyl-CoA reductase (see, e.g., Genbank Accession No. AAW66853.1, SEQ ID NO: 27).

FIG. 20 is a table of the conversion after 1 hour of adipyl-CoA methyl ester to adipyl-CoA by pimeloyl-[acp] methyl ester methylesterase.

DETAILED DESCRIPTION

Figure 1:
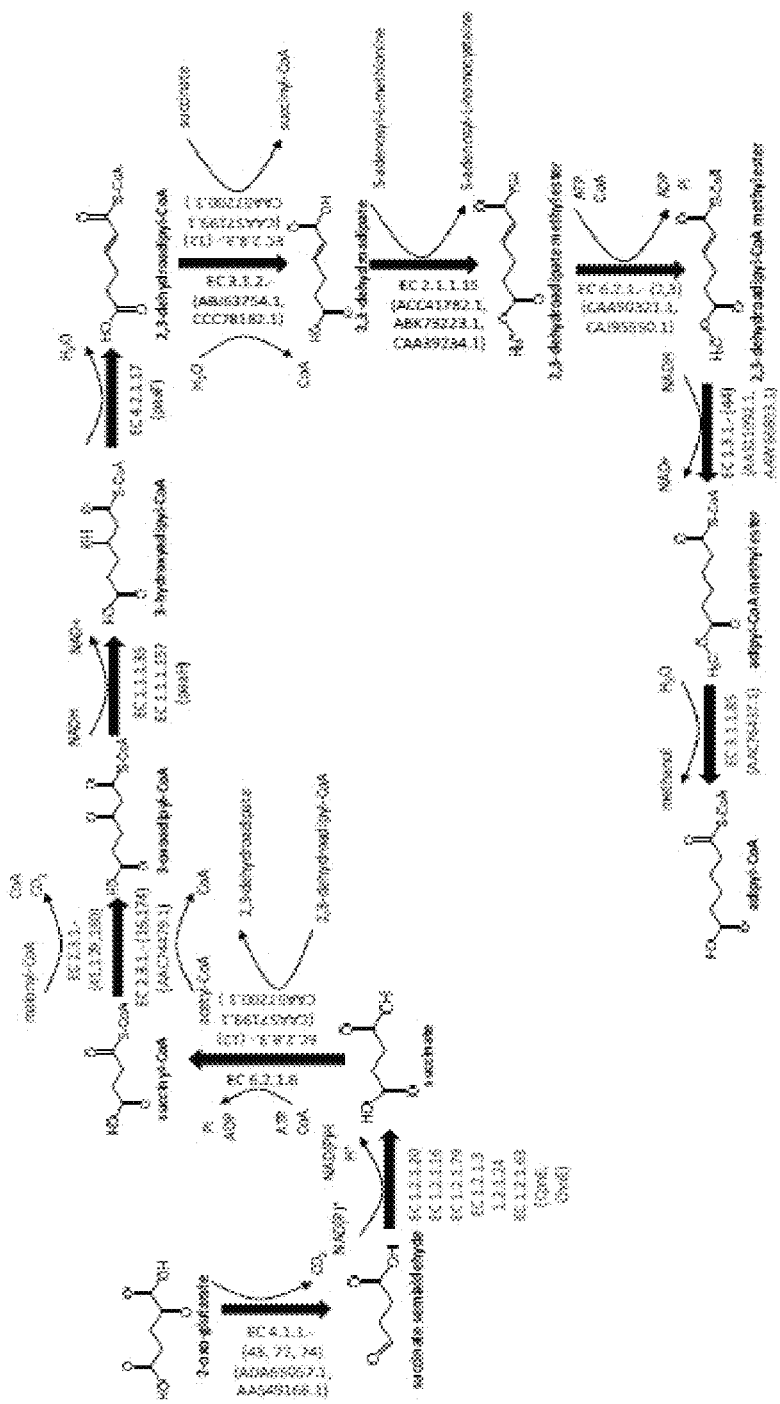
FIG. 1 is a schematic of an exemplary biochemical pathway leading to adipyl-CoA using succinyl-CoA as a central metabolite.

This document provides enzymes, non-natural pathways, cultivation strategies, feedstocks, host microorganisms and attenuations to the host's biochemical network, which generate a six carbon chain aliphatic backbone from central metabolites such as succinyl-CoA or 2-oxoadipate, in which one or two terminal functional groups may be formed leading to the synthesis of adipic acid, 6-aminohexanoic acid, 6-hydroxyhexanoate, caprolactam, hexamethylenediamine or 1,6-hexanediol. As used herein, the term "central precursor" is used to denote a key metabolite in a pathway leading to the synthesis of a C6 building block. The term "central metabolite" is used herein to denote a metabolite that is produced in microorganisms to support growth.

Host microorganisms described herein can include endogenous pathways that can be manipulated such that one or more C6 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, a recombinant host can express an exogenous polypeptide having fatty acid O-methyltransferase activity.

For example, depending on the host and the compounds produced by the host, one or more of the following polypeptides may be expressed in the host in addition to a polypeptide having (i) fatty acid O-methyltransferase activity, (ii) thioesterase activity or CoA-transferase activity, and (iii) CoA ligase activity: a pimelyl-[acp] methyl ester esterase, a thiolase, a β-ketothiolase, an acetyl-CoA C-acyltransferase, a 3-hydroxyacyl-CoA dehydrogenase, an enoyl-CoA hydratase, a trans-2-enoyl-CoA reductase, a 2-hydroxyglutarate dehydrogenase, a 2-hydroxyglutaryl-CoA dehydratase, a thioesterase, an aldehyde dehydrogenase, a 5-oxopentanoate dehydrogenase, a 6-oxohexanoate dehydrogenase, a 7-oxoheptanoate dehydrogenase, a reversible CoA-ligase (e.g., a reversible succinyl-CoA-ligase), a CoA-transferase (e.g., a glutaconate CoA-transferase), an acetylating aldehyde dehydrogenase, a carboxylate reductase, 4-hydroxybutyrate dehydrogenase, a 5-hydroxypentanoate dehydrogenase, a 6-hydroxyhexanoate dehydrogenase, a ω-transaminase, a N-acetyl transferase, an alcohol dehydrogenase, or a deacetylase. In recombinant hosts expressing a carboxylate reductase, a phosphopantetheinyl transferase also can be expressed as it enhances activity of the carboxylate reductase.

For example, a recombinant host can include at least one exogenous nucleic acid encoding a (i) fatty acid O-methyltransferase, (ii) a thioesterase and a CoA-transferase, and/or (iii) a CoA ligase. In some embodiments, a recombinant host includes an exogenous nucleic acid encoding a (i) fatty acid O-methyltransferase and a (ii) thioesterase or CoA-transferase, wherein the host produces 2,3-dehydroadipate methyl ester. In some embodiments, a recombinant host includes an exogenous nucleic acid encoding a fatty acid O-methyltransferase and a CoA ligase, wherein the host produces 2,3-dehydroadipate methyl ester. In some embodiments, the recombinant host includes an exogenous nucleic acid encoding (i) a fatty acid O-methyltransferase, (ii) a thioesterase or CoA-transferase, and (iii) a CoA ligase, and produces 2,3-dehydroadipyl-CoA methyl ester. Such a host further can include an exogenous trans-2-enoyl-CoA reductase and an exogenous pimeloyl-[acp] methyl ester methylesterase, and further produce adipyl-CoA.

In some embodiments, the recombinant host can include one of more of the following exogenous enzymes used to produce adipyl CoA from 2-oxoglutarate or succinyl-CoA as shown in FIG. 1: (a) a β-ketothiolase (b) a 3-hydroxyacyl-CoA dehydrogenase, (c) an enoyl-CoA hydratase, (d) a thioesterase or CoA-transferase, (e) a fatty acid O-methyltransferase, (f) a CoA ligase, (g) a trans-2-enoyl-CoA reductase, and (h) a pimeloyl-[acp] methyl ester methylesterase.

Figure 2:
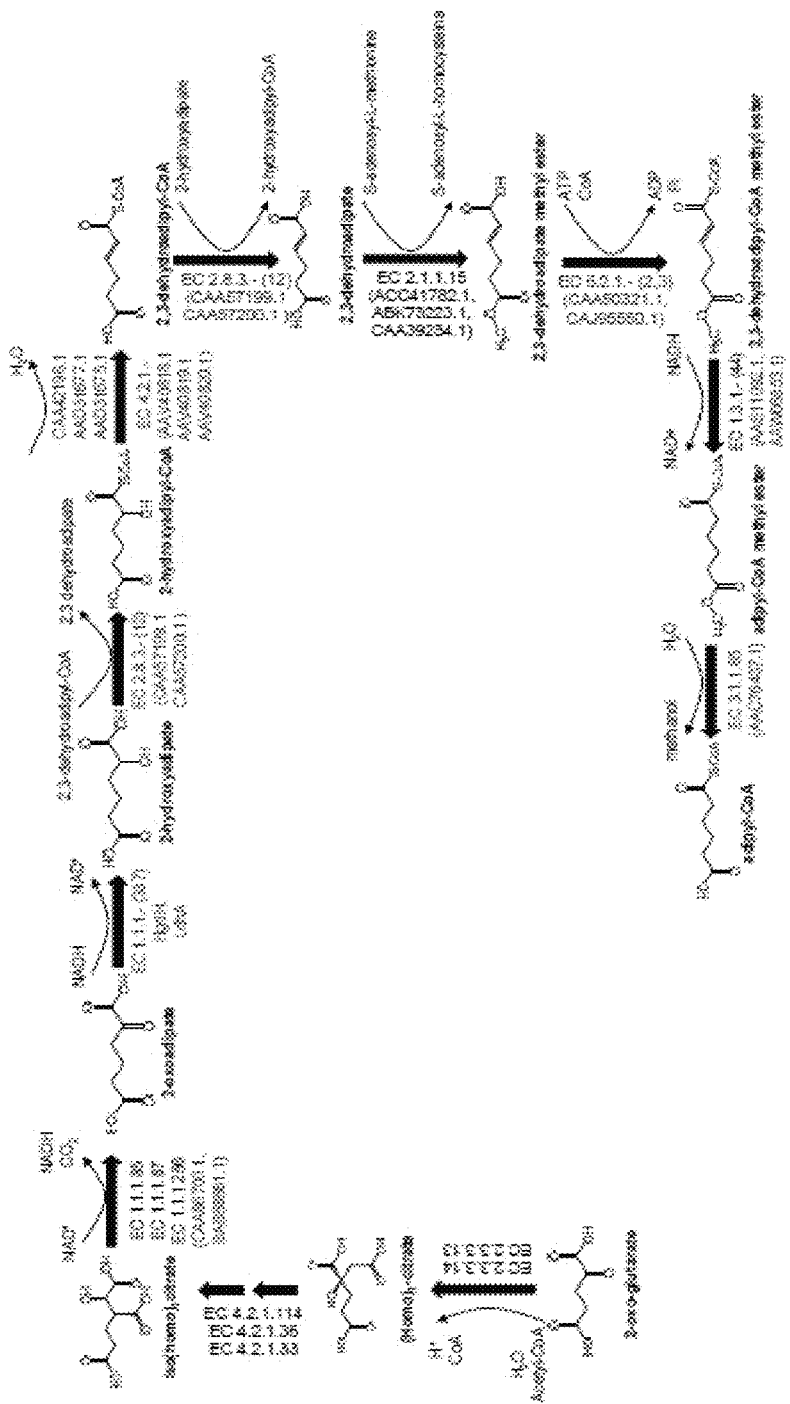
FIG. 2 is a schematic of an exemplary biochemical pathway leading to adipyl-CoA using 2-oxoadipate as a central metabolite.

In some embodiments, the host can include one or more of the following exogenous enzymes used to convert 2-oxoglutarate to adipyl CoA as shown in FIG. 2: (a) a homocitrate synthase, (b) a homocitrate dehydratase, (c) a homoaconitate hydratase, an (d) isohomocitrate dehydrogenase, (e) a 2-hydroxyglutarate dehydrogenase, (f) a CoA-transferase (e.g., a glutaconate CoA-transferase), (g) a 2-hydroxyglutaryl-CoA dehydratase, (h) a fatty acid O-methyltransferase, (i) a CoA ligase, (i) a trans-2-enoyl-CoA reductase, and (j) a pimeloyl-[acp] methyl ester methylesterase.

Such recombinant hosts producing adipyl CoA can include at least one exogenous nucleic acid encoding one or more of a thioesterase, an aldehyde dehydrogenase, a 7-oxoheptanoate dehydrogenase, a 5-oxopentanoate dehydrogenase, a 6-oxohexanoate dehydrogenase, a CoA-transferase, a reversible CoA-ligase, an acetylating aldehyde dehydrogenase, or a carboxylate reductase and produce adipic acid. For example, a recombinant host producing adipyl-CoA can include a thioesterase, a reversible CoA-ligase (e.g., a reversible succinyl-CoA ligase), or a CoA transferase (e.g., a glutaconate CoA-transferase) and produce adipic acid. For example, a recombinant host producing adipyl-CoA further can include an acetylating aldehyde dehydrogenase and produce adipate semialdehyde. For example, a recombinant host producing adipate further can include a carboxylate reductase and produce adipate semialdehyde. A recombinant host producing adipate semialdehyde can include an exogenous 7-oxoheptanoate dehydrogenase, 6-oxohexanoate dehydrogenase, a 5-oxopentanoate dehydrogenase, or an aldehyde dehydrogenase and produce adipic acid.

A recombinant host producing adipic acid or adipyl-CoA can include one or more of the following exogenous enzymes: an acetylating aldehyde dehydrogenase, a ω-transaminase, or a carboxylate reductase, and produce 6-aminohexanoate. In some embodiments, a recombinant host producing adipic acid includes an exogenous carboxylate reductase and an exogenous ω-transaminase to produce 6-aminohexanoate. In some embodiments, a recombinant host producing adipyl-CoA includes an exogenous acetylating aldehyde dehydrogenase and an exogenous ω-transaminase to produce 6-aminohexanoate.

A recombinant host producing 6-aminohexanoate further can include an exogenous hydroxy-cyclohexan-1-one amidohydrolase classified under EC 3.5.2.- and produce caprolactam.

A recombinant host producing adipate or adipate semialdehyde further can include at least one exogenous nucleic acid encoding a carboxylate reductase, a 6-hydroxyhexanoate dehydrogenase, a 5-hydroxypentanoate dehydrogenase or a 4-hydroxybutyrate dehydrogenase, and produce 6-hydroxyhexanoic acid. In some embodiments, a recombinant host producing adipyl-CoA includes an exogenous acetylating aldehyde dehydrogenase, and an exogenous 6-hydroxyhexanoate dehydrogenase, an exogenous 5-hydroxypentanoate dehydrogenase or an exogenous 4-hydroxybutyrate dehydrogenase to produce 6-hydroxyhexanoate. In some embodiments, a recombinant host producing adipate includes an exogenous carboxylate reductase and an exogenous 6-hydroxyhexanoate dehydrogenase, an exogenous 5-hydroxypentanoate dehydrogenase or an exogenous 4-hydroxybutyrate dehydrogenase to produce 6-hydroxyhexanoate.

A recombinant host producing 6-aminohexanoate, 6-hydroxyhexanoate, or adipate semialdehyde can include at least one exogenous nucleic acid encoding a carboxylate reductase, a ω-transaminase, a deacetylase, an N-acetyl transferase, or an alcohol dehydrogenase, and produce hexamethylenediamine. For example, a recombinant host producing 6-hydroxyhexanoate can include a carboxylate reductase with a phosphopantetheine transferase enhancer, at least one ω-transaminase, and an alcohol dehydrogenase. For example, a recombinant host producing 6-hydroxyhexanoate can include a carboxylate reductase with a phosphopantetheine transferase enhancer and a ω-transaminase. For example, a recombinant host producing 6-aminohexanoate can include a lysine N-acetyltransferase, a carboxylate reductase with a phosphopantetheine transferase enhancer, a ω-transaminase, and a deacetylase.

A recombinant host producing 6-hydroxyhexanoic acid can include one or more of the following exogenous enzymes: a carboxylate reductase with a phosphopantetheine transferase enhancer, a 6-hydroxyhexanoate dehydrogenase, a 5-hydroxypentanoate dehydrogenase, a 4-hydroxybutyrate dehydrogenase, or an alcohol dehydrogenase and an alcohol dehydrogenase, and produce 1,6-hexanediol.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C6 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a polypeptide having fatty acid O-methyltransferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see GenBank Accession No. ACC41782.1, SEQ ID NO: 1), a *Mycobacterium smegmatis* (see GenBank Accession No. ABK73223.1, SEQ ID NO: 2), or a *Pseudomonas putida* (see GenBank Accession No. CAA39234.1, SEQ ID NO: 3) methyltransferase. See FIGS. 9A-9B. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a polypeptide having thioesterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Lactobacillus brevis* (GenBank Accession No. ABJ63754.1, SEQ ID NO: 4) or a *Lactobacillus plantarum* (GenBank Accession No. CCC78182.1, SEQ ID NO: 5) acyl-[acp] thioesterase. See FIGS. 9B-9C.

For example, a polypeptide having pimelyl-[acp] methyl ester esterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* pimelyl-[acp] methyl ester esterase (see GenBank Accession No. AAC76437.1, SEQ ID NO: 6). See FIG. 9C.

For example, a polypeptide having carboxylate reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 7), a *Mycobacterium smegmatis* (see Genbank Accession No. ABK71854.1, SEQ ID NO: 8), a *Segniliparus rugosus* (see Genbank Accession No. EFV11917.1, SEQ ID NO: 9), a *Mycobacterium smegmatis* (see Genbank Accession No. ABK75684.1, SEQ ID NO: 10), a *Mycobacterium massiliense* (see Genbank Accession No. EIV11143.1, SEQ ID NO: 11), or a *Segniliparus rotundus* (see Genbank Accession No. ADG98140.1, SEQ ID NO: 12) carboxylate reductase. See FIGS. 9D-9I.

For example, a polypeptide having ω-transaminase activity described herein can have at least 70% sequence identity (homology) (e.g., at least 75%, 80%, 85%, 90%, 91%, 92%, 930%, 94%, 95%, 96%, 97%, 98%, 99%, or 100%) to the amino acid sequence of a *Chromobacterium violaceum* (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18) ω-transaminase. Some of these ω-transaminases are diamine ω-transaminases.

For example, a polypeptide having phosphopmanetheinyl transferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus subtilis* phosphopantetheinyl transferase (see Genbank Accession No. CAA44858.1, SEQ ID NO: 19) or a *Nocardia* sp. NRRL 5646 phosphopantetheinyl transferase (see Genbank Accession No. ABI83656.1, SEQ ID NO: 20). See FIG. 9L.

For example, a polypeptide having thioesterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* thioesterase encoded by tesB (see GenBank Accession No. AAA24665.1, SEQ ID NO: 21). See FIG. 9L.

For example, a polypeptide having long-chain-fatty-acid-CoA ligase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* long-chain-fatty-acid-CoA ligase (see Genbank Accession No. CAA50321.1, SEQ ID NO: 22), or a *Cupriavidus necator* long-chain-fatty-acid-CoA ligase (see Genbank Accession No. CAJ95550.1, SEQ ID NO: 23).

For example, a polypeptide having glutaconate CoA-transferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Acidaminococcus fermentans* glutaconate CoA-transferase (see, e.g., Genbank Accession No. CAA57199.1 (GctA) and CAA57200.1 (GctB), SEQ ID NOs: 24 and 25, respectively).

For example, a polypeptide having enoyl-CoA reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Treponema denticola* enoyl-CoA reductase (see, e.g., Genbank Accession No. AAS11092.1, SEQ ID NO: 26) or to the amino acid sequence of an *Euglena gracilis* enoyl-CoA reductase (see, e.g., Genbank Accession No. AAW66853.1, SEQ ID NO: 27).

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 91%; 92%; 93%; 94%; 95%; 96%; 97%; 98%; 99%; 100%; or even greater than 100%) of the activity of the corresponding mature, full-length, wild-type protein. The functional fragment can generally, but not always, be comprised of a continuous region of the protein, wherein the region has functional activity. Functional fragments are shorter than corresponding mature proteins but are generally at least 25 (e.g., at least: 30; 40; 50; 60; 70; 80, 90; 100; 120; 150; 200; 250; 300; 450; 500; 800; or more) amino acids long.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltose binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a methyltransferase, an esterase, a dehydratase, a hydratase, a dehydrogenase, a thioesterase, a reversible CoA-ligase, a CoA-transferase, a reductase, a deacetylase, a N-acetyl transferase or a ω-transaminase, as described in more detail below.

In addition, the production of one or more C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Biosynthetic Methods

The present document provides methods of shielding a carbon chain aliphatic backbone, functionalized with terminal carboxyl groups, in a recombinant host. The method can include enzymatically converting a n-carboxy-2-enoic acid to a n-carboxy-2-enoate methyl ester in the host using a polypeptide having the activity of a fatty acid O-methyltransferase, wherein n+1 reflects length of the carbon chain aliphatic backbone. For example, the n-carboxy-2-enoic acid can be four to 18, four to 16, four to 14, four to 12, four to 10, five to 10, five to nine, or five to eight carbons in length, e.g., 2,3-dehydroadipic acid, and can be enzymatically converted to the corresponding methyl ester, e.g., 2,3-dehydroadipate methyl ester. In some embodiments, the method further includes enzymatically converting 2,3-dehydroadipate methyl ester to adipyl-CoA. The polypeptide having fatty acid O-methyltransferase activity can be classified under EC 2.1.1.15. In some embodiments, the polypeptide having fatty acid O-methyltransferase activity has at least 70% sequence identity to an amino acid sequence set forth in SEQ ID NO: 1, SEQ ID NO: 2, or SEQ ID NO: 3.

In some embodiments, the method further includes enzymatically converting adipyl-CoA to a product selected from the group consisting of adipic acid, 6-aminohexanoate, 6-hydroxyhexanoate, caprolactam, hexamethylenediamine, and 1,6-hexanediol. For example, adipyl-CoA can be converted to the product using one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or alcohol dehydrogenase activity.

The present document further provides methods of producing 2,3-dehydroadipyl-CoA methyl ester in a recombinant host. The method can include enzymatically converting 2,3-dehydroadipate to 2,3-dehydroadipate methyl ester, wherein 2,3-dehydroadipate is enzymatically converted to 2,3-dehydroadipate methyl ester in the recombinant host using a polypeptide having fatty acid O-methyltransferase activity. The polypeptide having fatty acid O-methyltransferase activity can be classified under EC 2.1.1.15. In some embodiments, the polypeptide having fatty acid O-methyltransferase activity has at least 70% sequence identity to an amino acid sequence set forth in SEQ ID NO: 1, SEQ ID NO: 2, or SEQ ID NO: 3.

In some embodiments, the method further includes enzymatically converting 2,3-dehydroadipate methyl ester to adipyl-CoA methyl ester.

In some embodiments, 2,3-dehydroadipate is enzymatically produced from 2,3-dehydroadipyl-CoA. For example, a polypeptide having thioesterase or CoA-transferase activity can enzymatically convert 2,3-dehydroadipyl-CoA to 2,3-dehydroadipate. In some embodiments, the polypeptide having thioesterase activity has at least 70% sequence identity to an amino acid sequence set forth in SEQ ID NO: 4 or SEQ ID NO: 5. In some embodiments, the polypeptide having CoA-transferase activity has at least 70% sequence identity to an amino acid sequence set forth in SEQ ID NO: 24 or SEQ ID NO: 25.

In some embodiments, 2,3-dehydroadipate methyl ester is enzymatically converted to 2,3-dehydroadipyl-CoA methyl ester using a polypeptide having CoA ligase activity classified under EC 6.2.1.-. In some embodiments, the polypeptide having CoA ligase activity is classified under EC 6.2.1.2 or EC 6.2.1.3.

In some embodiments, the method further includes enzymatically converting 2,3-dehydroadipyl-CoA methyl ester to adipyl-CoA methyl ester. In some embodiments, a polypeptide having trans-2-enoyl-CoA reductase activity enzymatically converts 2,3-dehydroadipyl-CoA methyl ester to adipyl-CoA methyl ester.

In some embodiments, the method further includes enzymatically converting adipyl-CoA methyl ester to adipyl-CoA. In some embodiments, a polypeptide having pimelyl-[acp] methyl ester esterase activity enzymatically converts adipyl-CoA methyl ester to adipyl-CoA. In some embodiments, the polypeptide having pimelyl-[acp] methyl ester esterase activity has at least 70% sequence identity to the amino acid sequence set forth in SEQ ID NO: 6. In some embodiments, the method further includes enzymatically converting adipyl-CoA to a product selected from the group consisting of adipic acid, 6-aminohexanoate, caprolactam, 6-hydroxyhexanoate, hexamethylenediamine, and 1,6-hexanediol.

In some embodiments, the method includes enzymatically converting adipyl-CoA to adipic acid using a polypeptide having thioesterase, reversible CoA-ligase, or glutaconate CoA-transferase activity. In some embodiments, the method further includes enzymatically converting adipic acid to adipate semialdehyde using a polypeptide having carboxylate reductase activity. In some embodiments, the method includes enzymatically converting adipyl-CoA to adipate semialdehyde using a polypeptide having acetylating aldehyde dehydrogenase activity. In some embodiments, the method further includes enzymatically converting adipate semialdehyde to adipic acid using a polypeptide having 5-oxopentanoate dehydrogenase, 6-oxohexanoate dehydrogenase, 7-oxoheptanoate dehydrogenase, or aldehyde dehydrogenase activity. In some embodiments, the method further includes enzymatically converting adipate semialdehyde to 6-aminohexanoate using a polypeptide having ω-transaminase activity. In some embodiments, the method further includes enzymatically converting adipate semialdehyde to hexamethylenediamine using a polypeptide having ω-transaminase activity. In some embodiments, the method further includes enzymatically converting adipate semialdehyde to 6-hydroxyhexanoate using a polypeptide having 6-hydroxyhexanoate dehydrogenase, 5-hydroxypentanoate dehydrogenase, 4-hydroxybutyrate dehydrogenase, or alcohol dehydrogenase activity. In some embodiments, the method further includes enzymatically converting 6-hydroxyhexanoate to 1,6-hexanediol using a polypeptide having carboxylate reductase or alcohol dehydrogenase activity.

In some embodiments, one or more steps of the method are performed by fermentation. In some embodiments, the host is subjected to a cultivation strategy under aerobic, anaerobic, micro-aerobic, or mixed oxygen/denitrification cultivation conditions. In some embodiments, the host is cultured under conditions of phosphate, oxygen, and/or nitrogen limitation. In some embodiments, the host is retained using a ceramic membrane to maintain a high cell density during fermentation.

In some embodiments, the principal carbon source fed to the fermentation derives from biological or non-biological feedstocks. In some embodiments, the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste. In some embodiments, the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

In some embodiments, the host comprises one or more polypeptides having attenuated polyhydroxyalkanoate synthase, acetyl-CoA thioesterase, acetyl-CoA specific β-ketothiolase, phosphotransacetylase forming acetate, acetate kinase, lactate dehydrogenase, menaquinol-fumarate oxidoreductase, 2-oxoacid decarboxylase producing isobutanol, alcohol dehydrogenase forming ethanol, triose phosphate isomerase, pyruvate decarboxylase, glucose-6-phosphate isomerase, transhydrogenase dissipating the NADPH imbalance, glutamate dehydrogenase dissipating the NADPH imbalance, NADH/NADPH-utilizing glutamate dehydrogenase, pimeloyl-CoA dehydrogenase; acyl-CoA dehydrogenase accepting C7 building blocks and central precursors as substrates; glutaryl-CoA dehydrogenase; or pimeloyl-CoA synthetase activity.

In some embodiments, the host overexpresses one or more genes encoding a polypeptide having acetyl-CoA synthetase; 6-phosphogluconate dehydrogenase; transketolase; puridine nucleotide transhydrogenase; formate dehydrogenase; glyceraldehyde-3P-dehydrogenase; malic enzyme; glucose-6-phosphate dehydrogenase; fructose 1,6 diphosphatase; L-alanine dehydrogenase; PEP carboxylase; pyruvate carboxylase; PEP carboxykinase; PEP synthase; L-glutamate dehydrogenase specific to the NADPH used to generate a co-factor imbalance; methanol dehydrogenase; formaldehyde dehydrogenase; lysine transporter; dicarboxylate transporter; S-adenosylmethionine synthetase; 3-phosphoglycerate dehydrogenase; 3-phosphoserine aminotransferase; phosphoserine phosphatase; or a multidrug transporter activity.

In some embodiments, the host is a prokaryote, e.g., *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis,* and *Rhodococcus equi.*

In some embodiments, the host is a eukaryote, e.g., *Aspergillus niger, Saccharomyces cerevisiae, Pichia pastoris, Yarrowia lipolytica, Issathenkia orientalis, Debaryomyces hansenii, Arrula adenoinivorans,* and *Kluyveromyces lactis.*

Enzymes Generating the C6 Aliphatic Backbone for Conversion to C6 Building Blocks As depicted in FIGS. 1 and 2, adipyl-CoA can be produced from succinyl-CoA or 2-oxoadipate via 2,3-dehydroadipate methyl ester and 2,3-dehydroadipyl-CoA methyl ester intermediates. 2,3-dehydroadipate methyl ester can be formed from 2,3-dehydroadipate using a fatty acid O-methyltransferase, such as the fatty acid O-methyltransferase classified, for example, under EC 2.1.1.15. For example, the fatty acid O-methyltransferase can be obtained from *Mycobacterium marinum* (GenBank Accession No. ACC41782.1, SEQ ID NO: 1), *Mycobacterium smegmatis* (see GenBank Accession No. ABK73223.1, SEQ ID NO: 2), or *Pseudomonas putida* (see GenBank Accession No. CAA39234.1, SEQ ID NO: 3).

2,3-dehydroadipate methyl ester can be converted to 2,3-dehydroadipyl-CoA methyl ester using, for example, a CoA ligase classified, for example, under EC 6.2.1.-. In some embodiments, a butyrate-CoA ligase classified under EC 6.2.1.2 or a long-chain-fatty-acid-CoA ligase classified under EC 6.2.1.3 such as the long chain fatty acid CoA-ligase from *Escherichia coli* (Genbank Accession No. CAA50321.1, SEQ ID NO: 22) or *Cupriavidus necator* (Genbank Accession No. CAJ95550.1, SEQ ID NO: 23) can be used to convert 2,3-dehydroadipate methyl ester to 2,3-dehydroadipyl-CoA methyl ester. See, FIGS. 1 and 2.

2,3-dehydroadipyl-CoA methyl ester can be converted to adipyl-CoA using a trans-2-enoyl-CoA reductase and an esterase. See FIGS. 1 and 2. In some embodiments, a trans-2-enoyl-CoA reductase can be classified under EC 1.3.1.44, such as the gene product of ter (Genbank Accession No. AAW66853.1) (Nishimaki et al., J. Biochem., 1984, 95, 1315-1321; Shen et al., *Appl. Environ. Microbiol.*, 2011, 77(9), 2905-2915) or tdter (Genbank Accession No. AAS11092.1) (Bond-Watts et al., *Biochemistry,* 51, 6827-6837). See, FIGS. 1 and 2.

In some embodiments, a pimelyl-[acp] methyl ester esterase can be classified under EC 3.1.1.85 such as the gene product of bioH (GenBank Accession No. AAC76437.1, SEQ ID NO: 6). See, FIGS. 1 and 2.

In some embodiments, 2,3-dehydroadipate can be formed from 2,3-dehydroadipyl-CoA using, for example, a thioesterase classified under EC 3.1.2.-, such as the acyl-[acp] thioesterase from *Lactobacillus brevis* (GenBank Accession No. ABJ63754.1, SEQ ID NO: 4) or from *Lactobacillus plantarum* (GenBank Accession No. CCC78182.1, SEQ ID NO: 5). Such acyl-[acp] thioesterases have C6-C8 chain length specificity (see, for example, Jing et al., 2011, *BMC Biochemistry,* 12(44)). See, e.g., FIG. 1.

In some embodiments, 2,3-dehydroadipate can be formed from 2,3-dehydroadipyl-CoA using, for example, a CoA-transferase (e.g., a glulaconate CoA-transferase) classified, for example, under EC 2.8.3.12 such as the gene product of GctAB from *Acidaminococcus fermentans.* See, for example, Buckel et al., 1981, *Eur. J. Biochem.* 118:315-321. See, e.g., FIG. 2.

In some embodiments, 2,3-dehydroadipyl-CoA can be produced from succinyl-CoA using a thiolase, a 3-hydroxyacyl-CoA dehydrogenase, and an enoyl-CoA hydratase. See, FIG. 1. A thiolase can be β-ketothiolase classified, for example, under EC. 2.3.1.174 such as encoded by of paaJ (See, e.g., Genbank Accession No. AAC74479.1), catF and pcaF or an acetyl-CoA C-acyltransferase classified, for example, under EC 2.3.1.16. The β-ketothiolase encoded by paaJ condenses acetyl-CoA and succinyl-CoA to form 3-oxoadipyl-CoA (see, for example, Fuchs et al., 2011, *Nature Reviews Microbiology* 9, 803-816). See, FIG. 1.

In some embodiments, a 3-hydroxyacyl-CoA dehydrogenase can be classified under EC 1.1.1.-. For example, a 3-hydroxyacyl-CoA dehydrogenase can be classified under EC 1.1.1.35 or EC 1.1.1.157, such as the gene product of paaH (Teufel et al., 2010, *Proc. Natl. Acad. Sci.* 107(32), 14390-14395). See, FIG. 1.

In some embodiments, an enoyl-CoA hydratase can be classified under EC 4.2.1.17, such as the gene product of paaF (Teufel et al., 2010, supra). See, FIG. 1.

In some embodiments, 2,3-dehydroadipyl-CoA can be produced from 2-oxoadipate using a 2-hydroxyglutarate dehydrogenase, a CoA-transferase (e.g., a glutaconate CoA-transferase), and a 2-hydroxyglutaryl-CoA dehydratase. See, FIG. 2. A 2-hydroxyglutarate dehydrogenase can be classified, for example under EC 1.1.1.- such as the gene product of HgdH (see, for example, Djurdjevic et al, 2011, *Appl. Environ. Microbiol.* 77(1), 320-322. See, FIG. 2.

A 2-hydroxyglutaryl-CoA dehydratase can be classified, for example, under EC 4.2.1.- such as the gene product of HgdAB (Genbank Accession Nos. AAD31677.1 and AAD31675.1) in combination with its activator, the gene product of HgdC (Genbank Accession No. CAA42196.1). The HgdAB gene product contains subunits A and B. See, Djurdjevic et al., 2011, supra. A 2-hydroxyisocaproy-CoA dehydratase can be classified, for example, under EC 4.2.1.- such as the gene product of hadBC (Genbank Accession Nos. AAV40819.1 & AAV40820.1) or hadI (Genbank Accession No. AAV40818.1). See, FIG. 2.

Enzymes Facilitating Introduction of Terminal Functional Groups in the Biosynthesis of a C6 Building Block In some embodiments, a carboxylate reductase facilitates the generation of a terminal aldehyde group for subsequent conversion to an amine group by an ω-transaminase or to a hydroxyl group by an alcohol dehydrogenase. The carboxylate reductase can be obtained, for example, from *Mycobacterium marinum* (Genbank Accession No. ACC40567.1, SEQ ID NO: 7), *Mycobacterium smegmatis* (Genbank Accession No. ABK71854.1, SEQ ID NO: 8), *Segniliparus rugosus* (Genbank Accession No. EFV11917.1, SEQ ID NO: 9), *Mycobacterium smegmatis* (Genbank Accession No. ABK75684.1, SEQ ID NO: 10), *Mycobacterium massiliense* (Genbank Accession No. EIV11143.1, SEQ ID NO: 11), or *Segniliparus rotundus* (Genbank Accession No. ADG98140.1, SEQ ID NO: 12). See, e.g., FIGS. 4 to 8.

The carboxylate reductase encoded by the gene product of car and enhancer npt has broad substrate specificity, including terminal difunctional C4 and C5 carboxylic acids (Venkitasubramanian et al., *Enzyme and Microbial Technology*, 2008, 42, 130-137).

Figure 3:
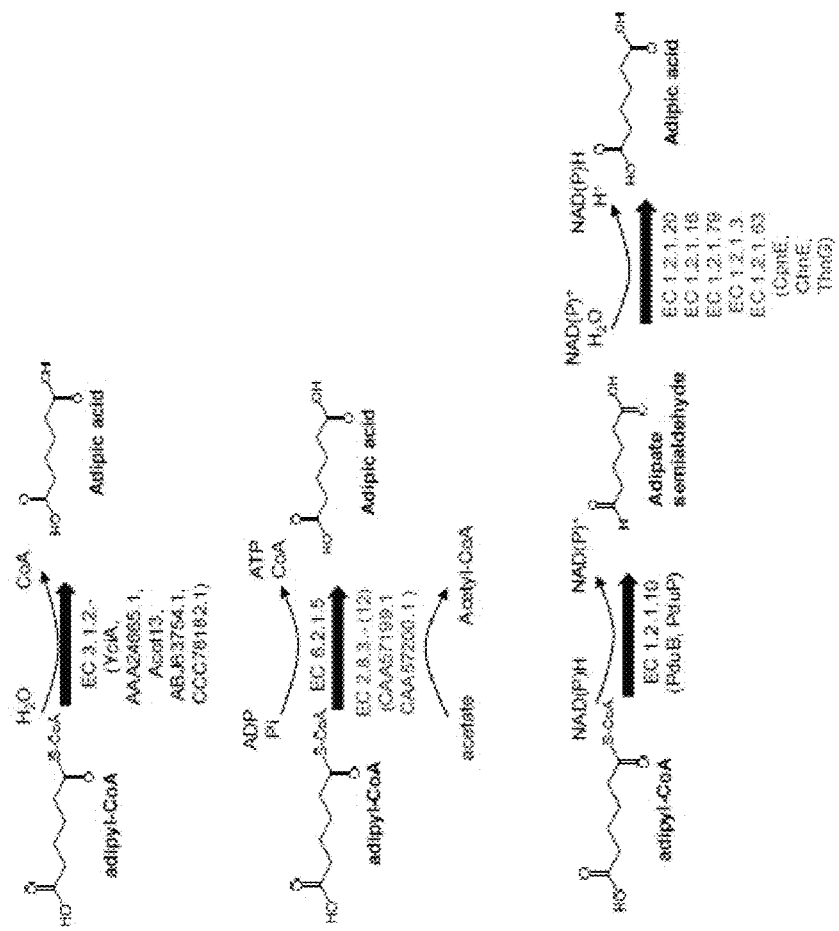
FIG. 3 is a schematic of exemplary biochemical pathways leading to adipic acid using adipyl-CoA as a central precursor.

Enzymes Generating the Terminal Carboxyl Groups in the Biosynthesis of C6 Building Blocks As depicted in FIGS. 1 to 3, a terminal carboxyl group can be enzymatically formed using a methyl ester esterase, a thioesterase, an aldehyde dehydrogenase, a 7-oxoheptanoate dehydrogenase, a 6-oxohexanoate dehydrogenase, a 5-oxopentanoate dehydrogenase, a CoA-transferase or a reversible CoA-ligase.

In some embodiments, the first terminal carboxyl group leading to the synthesis of a C6 building block is enzymatically formed by a pimelyl-[acp] methyl ester esterase classified, for example, under EC 3.1.1.85 such as the gene product of bioH (GenBank Accession No. AAC76437.1, SEQ ID NO: 6). See, FIGS. 1 and 2.

In some embodiments, a second terminal carboxyl group leading to the synthesis of a C6 building block is enzymatically formed by a thioesterase classified under EC 3.1.2.-, such as the gene product of YciA, tesB (Genbank Accession No. AAA24665.1, SEQ ID NO: 21) or Acot13 (see, for example, Cantu et al., *Protein Science*, 2010, 19, 1281-1295; Zhuang et al., *Biochemistry*, 2008, 47(9), 2789-2796; or Naggert et al., *J. Biol. Chem.*, 1991, 266(17), 11044-11050), or an acyl-[acp] thioesterase (e.g., from *Lactobacillus brevis* (GenBank Accession No. ABJ63754.1, SEQ ID NO: 4) or from *Lactobacillus plantarum* (GenBank Accession No. CCC78182.1, SEQ ID NO: 5). See, FIG. 3.

In some embodiments, the second terminal carboxyl group leading to the synthesis of adipic acid is enzymatically formed by an aldehyde dehydrogenate classified, for example, under EC 1.2.1.3 (see, for example, Guerrillot & Vandecasteele, *Eur. J. Biochem.*, 1977, 81, 185-192). See, FIG. 3.

In some embodiments, the second terminal carboxyl group leading to the synthesis of adipic acid is enzymatically formed by a dehydrogenase classified under EC 1.2.1.- (e.g., EC 1.2.1.16, EC 1.2.1.20, EC 1.2.1.79, EC 1.2.1.3 or EC 1.2.1.63) such as a 4-oxobutanoate dehydrogenase (e.g., the gene product of gabD from *Cupriavidus necator*), 5-oxopentanoate dehydrogenase (e.g., the gene product of CpnE from *Comamonas* sp. strain NCIMB 9872), a 6-oxohexanoate dehydrogenase (e.g., the gene product of ChnE from *Acinetobacter* sp.) or a 7-oxoheptanoate dehydrogenase (e.g., the gene product of ThnG from *Sphingomonas macrogolitabida*). See, for example, Iwaki et al., *Appl. Environ. A Microbiol.*, 1999, 65(11), 5158-5162; Iwaki et al., *Appl. Environ. Microbiol.*, 2002, 68(11), 5671-5684; or López-Sánchez et al., Appl. Environ. Microbiol., 2010, 76(1), 110-118. For example, a 5-oxoopentanoate dehydrogenase can be classified under EC 1.2.1.20. For example, a 6-oxohexanoate dehydrogenase can be classified under EC 1.2.1.63. For example, a 7-oxoheptanoate dehydrogenase can be classified under EC 1.2.1.-. See, FIG. 3.

In some embodiments, the second terminal carboxyl group leading to the synthesis of adipic acid is enzymatically formed by a CoA-transferase such as a glutaconate CoA-transferase classified, for example, under EC 2.8.3.12 such as from *Acidaminococcus fermentans*. See, for example, Buckel et al., 1981, *Eur. J. Biochem.*, 118:315-321. See, FIG. 3.

In some embodiments, the second terminal carboxyl group leading to the synthesis of adipic acid is enzymatically formed by a reversible CoA-ligase such as a succinate-CoA ligase classified, for example, under EC 6.2.1.5 such as from *Thermococcus kodakaraensis*. See, for example, Shikata et al., 2007, *J. Biol. Chem.*, 282(37):26963-26970. See, FIG. 3.

Figure 4:
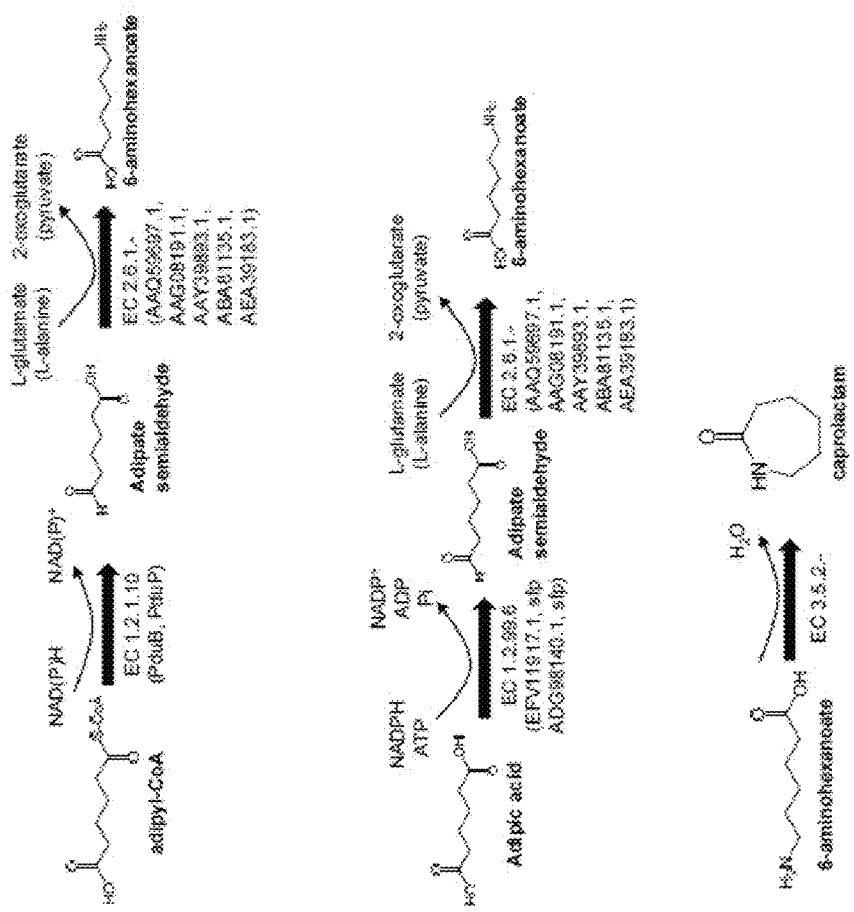
FIG. 4 is a schematic of two exemplary biochemical pathways leading to 6-aminohexanoate using adipic acid or adipyl-CoA as a central precursor and a schematic of an exemplary biochemical pathway leading to caprolactam using 6-aminohexanoate as a central precursor.
Figure 5:
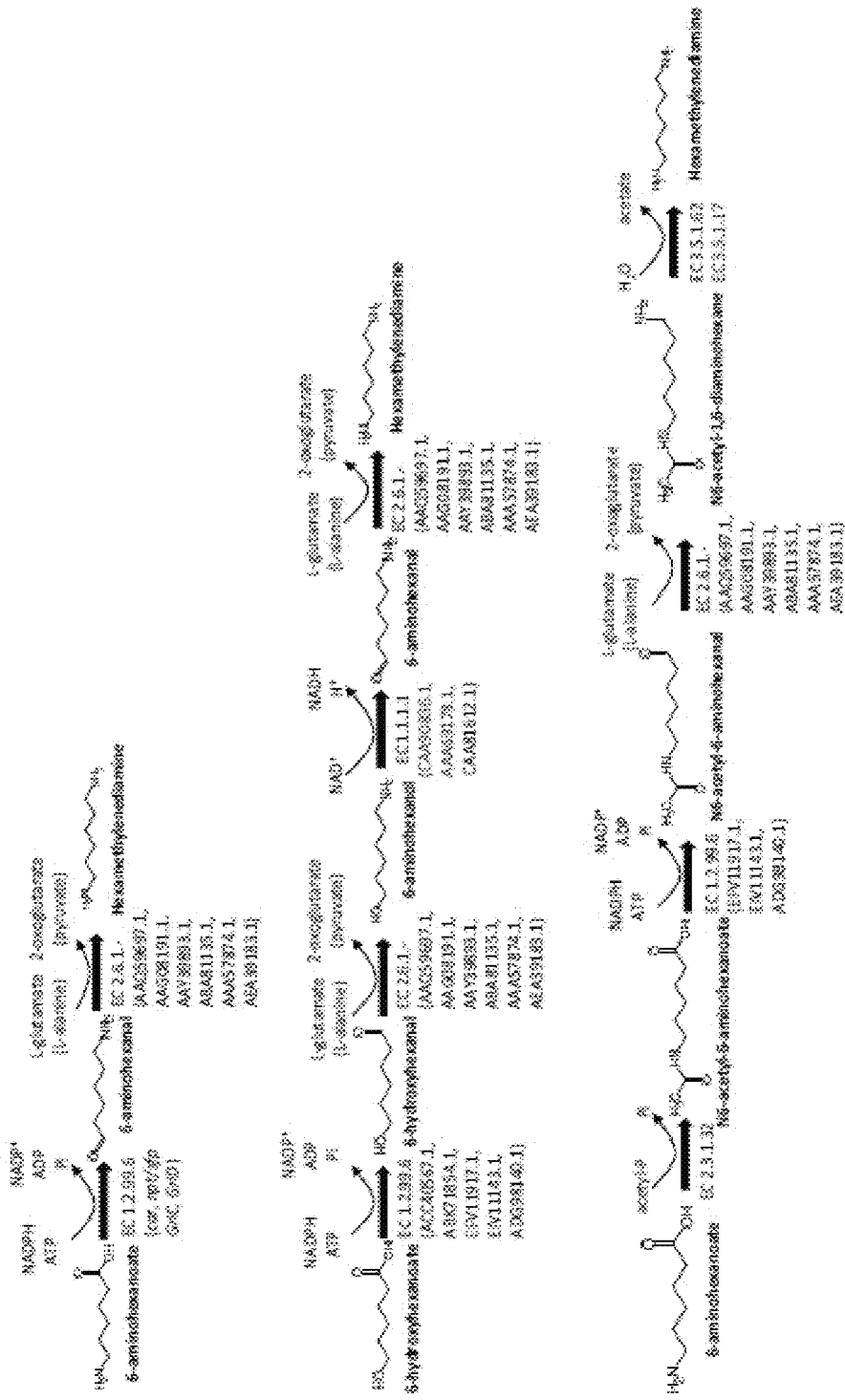
FIG. 5 is a schematic of exemplary biochemical pathways leading to hexamethylenediamine using 6-aminohexanoate or 6-hydroxyhexanoate as a central precursor.
Figure 6:
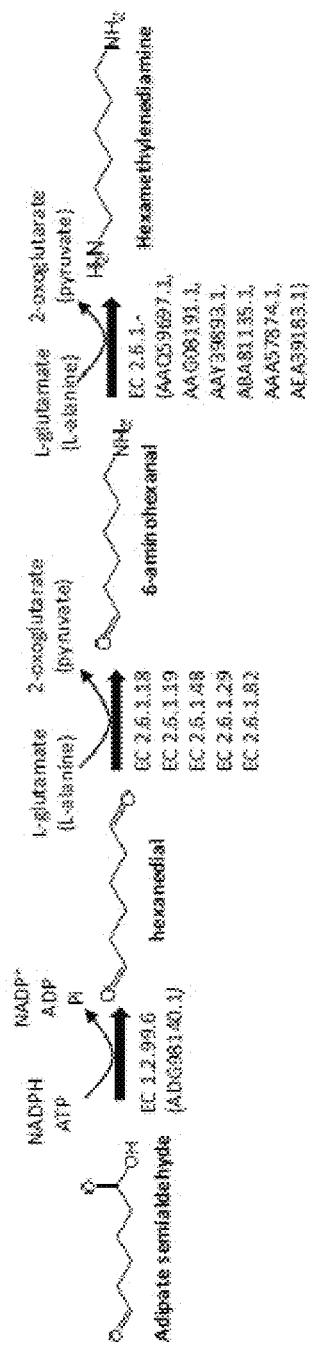
FIG. 6 is a schematic of an exemplary biochemical pathway leading to hexamethylenediamine using adipate semialdehyde as a central precursor.

Enzymes Generating the Terminal Amine Groups in the Biosynthesis of C6 Building Blocks As depicted in FIGS. 4, 5, and 6, the terminal amine groups can be enzymatically formed using a ω-transaminase or a deacetylase. Caprolactam can be produced from 6-aminohexanoic acid using a hydroxy-cyclohexan-1-one amidohydrolase classified under EC 3.5.2.-. The amide bond associated with caprolactam is the result of 6-aminohexanoate having a terminal carboxyl group and terminal amine group to form the bond.

In some embodiments, the first or second terminal amine group leading to the synthesis of 6-aminohexanoic acid is enzymatically formed by a ω-transaminase classified, for example, under EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 13), *Pseudomonas aeruginosa* (Genbank Accession No. AAG08191.1, SEQ ID NO: 14), *Pseudomonas syringae* (Genbank Accession No. AAY39893.1, SEQ ID NO: 15), *Rhodobacter sphaeroides* (Genbank Accession No. ABA81135.1, SEQ ID NO: 16), *Escherichia coli* (Genbank Accession No. AAA57874.1, SEQ ID NO: 17), *Vibrio fluvialis* (Genbank Accession No. AEA39183.1, SEQ ID NO: 18), *Streptomyces griseus*, or *Clostridium viride*. Some of these ω-transaminases are diamine ω-transaminases (e.g., SEQ ID NO: 17). For example, the ω-transaminases classified, for example, under EC 2.6.1.29 or EC 2.6.1.82 may be diamine ω-transaminases.

The reversible ω-transaminase from *Chromobacterium violaceum* (Genbank Accession No. AAQ59697.1, SEQ ID NO: 13) has demonstrated analogous activity accepting 6-aminohexanoic acid as amino donor, thus forming the first terminal amine group in adipate semialdehyde (Kaulmann et al., *Enzyme and Microbial Technology*, 2007, 41, 628-637).

The reversible 4-aminobubyrate:2-oxoglutarate transaminase from *Streptomyces griseus* has demonstrated analogous activity for the conversion of 6-aminohexanoate to adipate semialdehyde (Yonaha et al., *Eur. J. Biochem.*, 1985, 146: 101-106).

The reversible 5-aminovalerate transaminase from *Clostridium viride* has demonstrated analogous activity for the conversion of 6-aminohexanoate to adipate semialdehyde (Barker et al., *J. Biol. Chem.*, 1987, 262(19), 8994-9003).

In some embodiments, a terminal amine group leading to the synthesis of 6-aminohexanoate or hexamethylenediamine is enzymatically formed by a diamine w-transaminase. For example, the second terminal amino group can be enzymatically formed by a diamine ω-transaminase classified, for example, under EC 2.6.1.29 or classified, for example, under EC 2.6.1.82, such as the gene product of YgjG from *E. coli* (Genbank Accession No. AAA57874.1, SEQ ID NO: 17).

The gene product of ygjG accepts a broad range of diamine carbon chain length substrates, such as putrescine, cadaverine and spermidine (see, for example, Samsonova et al., *BMC Microbiology,* 2003, 3:2).

The diamine ω-transaminase from *E. coli* strain B has demonstrated activity for 1,7 diaminoheptane (Kim, *The Journal of Chemistry,* 1964, 239(3), 783-786).

In some embodiments, the second terminal amine group leading to the synthesis of hexamethylenediamine is enzymatically formed by a deacetylase such as an acyl-lysine deacylase classified, for example, under EC 3.5.1.17 or such as acetylputrescine deacetylase classified, for example, under EC 3.5.1.62. The acetylputrescine deacetylase from *Micrococcus luteus* K-11 accepts a broad range of carbon chain length substrates, such as acetylputrescine, acetylcadaverine and $N^8$.acetylspermidine (see, for example, Suzuki et al., 1986, *BBA—General Subjects,* 882(1):140-142).

Figure 7:
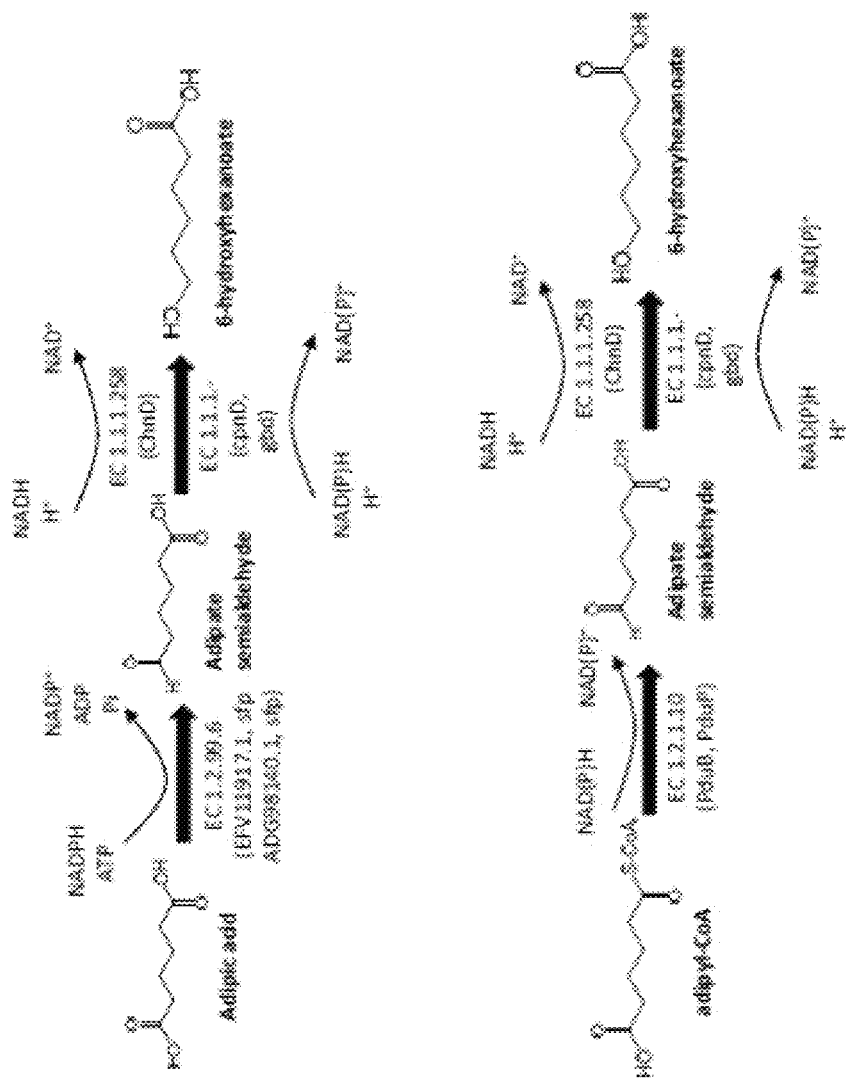
FIG. 7 is a schematic of exemplary biochemical pathways leading to 6-hydroxyhexanoate using adipic acid or adipyl-CoA as a central precursor.
Figure 8:
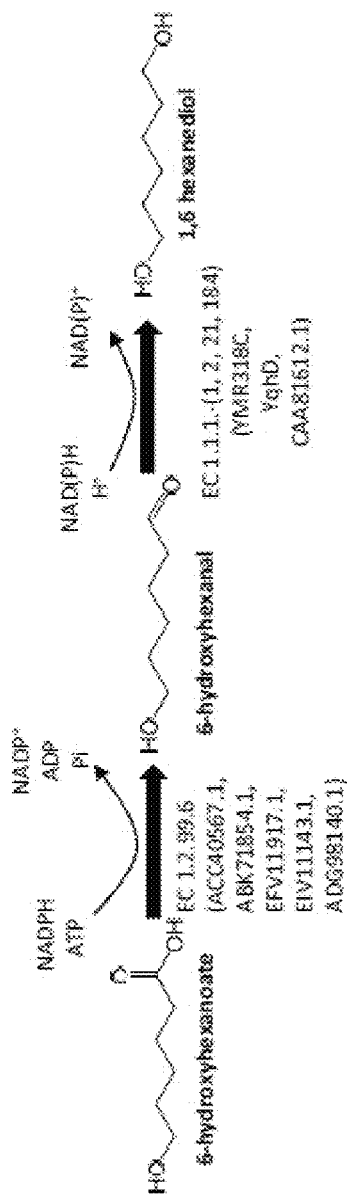
FIG. 8 is a schematic of an exemplary biochemical pathway leading to 1,6-hexanediol using 6-hydroxyhexanoate as a central precursor.

Enzymes Generating the Terminal Hydroxyl Groups in the Biosynthesis of C6 Building Blocks As depicted in FIG. 7 and FIG. 8, the terminal hydroxyl group can be enzymatically formed using a 6-hydroxyhexanoate dehydrogenase, a 5-hydroxypentanoate dehydrogenase, 4-hydroxybutyrate dehydrogenase, or an alcohol dehydrogenase.

For example, a terminal hydroxyl group leading to the synthesis of 6-hydroxyhexanoic acid can be enzymatically formed by a dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD (see, for example, Iwaki et al., 2002, *Appl. Environ. Microbiol.,* 68(11):5671-5684), a 5-hydroxypentanoate dehydrogenase from *Clostridium viride,* or a 4-hydroxybutyrate dehydrogenase such as ghd. See, FIG. 7.

In some embodiments, a terminal hydroxyl group leading to the synthesis of 1,6 hexanediol is enzymatically formed by an alcohol dehydrogenase classified under EC 1.1.1.- (e.g., 1, 2, 21, or 184).

Biochemical Pathways

Pathway to Adipyl-CoA from Succinyl-CoA as a Central Precursor

As shown in FIG. 1, adipyl-CoA can be synthesized from the central metabolite succinyl-CoA, by conversion of succinyl-CoA to 3-oxoadipyl-CoA by a thiolase classified, for example, under EC 2.3.1.16 or 2.3.1.174 such as the gene product of paaJ; followed by conversion to 3-oxoadipyl-CoA by a 3-hydroxyacyl-CoA dehydrogenase classified, for example, under EC 1.1.1.157 such as the gene product of paaH; followed by conversion to 2,3-dehydroadipyl-CoA by an enoyl-CoA hydratase classified, for example, under EC 4.2.1.17 such as the gene product of paaF; followed by conversion to 2,3-dehydroadipate by a thioesterase classified, for example, under EC 3.1.2.- such as from *Lactobacillus brevis* (GenBank Accession No. ABJ63754.1, SEQ ID NO: 4) or from *Lactobacillus plantarum* (GenBank Accession No. CCC78182.1, SEQ ID NO: 5); followed by conversion to 2,3-dehydroadipate methyl ester by a fatty acid O-methyltransferase classified, for example, under EC 2.1.1.15 such as one obtained from *Mycobacterium marimum* (GenBank Accession No. ACC41782.1, SEQ ID NO: 1), *Mycobacterium smegmatis* (see GenBank Accession No. ABK73223.1, SEQ ID NO: 2), or *Pseudomonas putida* (see GenBank Accession No. CAA39234.1, SEQ ID NO: 3); followed by conversion to 2,3-dehydroadipyl-CoA methyl ester by a CoA ligase classified, for example, under EC 6.2.1.- such as butyrate-CoA ligase classified under EC 6.2.1.2 or a long-chain-fatty-acid-CoA ligase classified under EC 6.2.1.3; followed by conversion to adipyl-CoA methyl ester by a trans-2-enoyl-CoA reductase classified, for example, under EC 1.3.1.44 such as the gene product of ter or tdter; followed by conversion to adipyl-CoA by a pimelyl-[acp] methyl ester esterase classified, for example, under EC 3.1.1.85 such as the gene product of bioH (see, e.g., SEQ ID NO: 6). See FIG. 1.

Pathway to Adipyl-CoA from 2-Oxoadipate as a Central Precursor

As shown in FIG. 2, adipyl-CoA can be synthesized from the central metabolite 2-oxoadipate by conversion of 2-oxoadipate to 2-hydroxyadipate by a hydroxyglutarate dehydrogenase such as the gene product of HgdH; followed by conversion to 2-hydroxyadipyl-CoA by a CoA transferase classified, for example, under EC 2.8.3.12 such as the gene product of GctAB (see, e.g., Genbank Accession No. CAA57199.1 (GctA) and CAA57200.1 (GctB), SEQ ID NOs: 24 and 25, respectively); followed by conversion to 2,3-dehydroadipyl-CoA by a 2-hydroxyglutaryl-CoA dehydratase classified, for example, under EC 4.2.1.- such as the gene product of HgdAB in combination with its activator, the gene product of HgdC (see Djurdjevic et al, 2011, supra) or a 2-hydroxyisocaproyl-CoA dehydratase classified, for example, under EC 4.2.1.- such as the gene product of hadBC in combination with its activator, the gene product of hadI (Kim et al., 2005, *FEBS Journal,* 272, 550-561); followed by conversion to 2,3-dehydroadipate by a CoA transferase classified, for example, under EC 2.8.3.12 such as the gene product of GctAB; followed by conversion to 2,3-dehydroadipate methyl ester by a fatty acid O-methyltransferase classified, for example, under EC 2.1.1.15 such as one obtained from *Mycobacterium marimum* (GenBank Accession No. ACC41782.1, SEQ ID NO: 1), *Mycobacterium smegmatis* (see GenBank Accession No. ABK73223.1, SEQ ID NO: 2), or *Pseudomonas putida* (see GenBank Accession No. CAA39234.1, SEQ ID NO: 3); followed by conversion to 2,3-dehydroadipyl-CoA methyl ester by a CoA ligase classified, for example, under EC 6.2.1.- such as butyrate-CoA ligase classified under EC 6.2.1.2 or a long-chain-fatty-acid-CoA ligase classified under EC 6.2.1.3 (e.g., Genbank Accession No. CAA50321.1 or CAJ95550.1); followed by conversion to adipyl-CoA methyl ester by a trans-2-enoyl-CoA reductase classified, for example, under EC 1.3.1.44 such as the gene product of ter (e.g., Genbank Accession No. AAW66853.1) or tdter (Genbank Accession No. AAS11092.1); followed by conversion to adipyl-CoA by a pimelyl-[acp] methyl ester esterase classified, for example, under EC 3.1.1.85 such as the gene product of bioH (GenBank Accession No. AAC76437.1, SEQ ID NO: 6). See, FIG. 2.

Pathways Using Adipyl-CoA as Central Precursor to Adipic Acid

In some embodiments, adipic acid is synthesized from the central precursor, adipyl-CoA, by conversion of adipic-CoA to adipic acid by a thioesterase classified, for example, under EC 3.1.2.- such as the gene product of YciA, tesB (Genbank Accession No. AAA24665.1, SEQ ID NO: 21) or Acot13 (see, for example, Cantu et al., *Protein Science,* 2010, 19, 1281-1295; Zhuang et al., *Biochemistry,* 2008, 47(9), 2789-2796; or Naggert et al., *J. Biol. Chem.,* 1991, 266(17), 11044-11050), or a thioesterase (e.g., from *Lactobacillus brevis* (GenBank Accession No. ABJ63754.1, SEQ ID NO: 4) or from *Lactobacillus plantarum* (GenBank Accession No. CCC78182.1, SEQ ID NO: 5).

In some embodiments, adipic acid is synthesized from the central precursor, adipyl-CoA, by conversion of adipic-CoA to adipic acid by a reversible succinate CoA-ligase classified, for example, under EC 6.2.1.5. See FIG. 3.

In some embodiments, adipic acid is synthesized from the central precursor, adipyl-CoA, by conversion of adipyl-CoA to adipic acid by a glutaconate CoA-transferase classified, for example, under EC 2.8.3.12. See, FIG. 3.

In some embodiments, adipic acid is synthesized from the central precursor, adipyl-CoA, by conversion of adipyl-CoA to adipate semialdehyde by an acetylating aldehyde dehydrogenase classified, for example, under EC 1.2.1.10 such as the gene product of PduB or PduP (Lan et al., 2013, *Energy Environ Sci.*, 6, 2672-2681); followed by conversion to adipic acid by a dehydrogenase classified, for example, under EC 1.2.1.- such as an aldehyde dehydrogenase (EC 1.2.1.3), a 4-oxobutanoate dehydrogenase (e.g., the gene product of gabD from *Cupriavidus necator*), a 5-oxopentanoate dehydrogenase (EC 1.2.1.20) such as the gene product of CpnE, 6-oxohexanoate dehydrogenase (EC 1.2.1.63) such as the gene product of ChnE, or 7-oxoheptanoate dehydrogenase (EC 1.2.1.-) such as the gene product of ThnG. See, FIG. 3.

Pathway Using Adipic Acid or Adipyl-CoA as Central Precursor to 6-Aminohexanoate In some embodiments, 6-aminohexanoate is synthesized from the central precursor, adipic acid, by conversion of adipic acid to adipate semialdehyde by a carboxylate reductase classified, for example, under EC 1.2.99.6 such as from *Segniliparus rugosus* (Genbank Accession No. EFV11917.1, SEQ ID NO: 9) or *Segniliparus rotundus* (Genbank Accession No. ADG98140.1, SEQ ID NO: 12), in combination with a phosphopmanetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene products of GriC and GriD from *Streptomyces griseus* (Suzuki et al., *J. Antibiot.*, 2007, 60(6), 380-387); followed by conversion to 6-aminohexanoate by a ω-transaminase classified, for example, under EC 2.6.1.- (e.g., EC 2.6.1.18, EC 2.6.1.19, EC 2.6.1.29, EC 2.6.1.48, or EC 2.6.1.82) such as from a *Chromobacterium violaceum* (see Genbank Accession No. AAQ59697.1, SEQ ID NO: 13), a *Pseudomonas aeruginosa* ω-transaminase (See Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), or a *Vibrio fluvialis* (see Genbank Accession No. AEA39183.1, SEQ ID NO: 18). See, FIG. 4.

In some embodiments, 6-aminohexanoate is synthesized from the central precursor, adipyl-CoA, by conversion of adipyl-CoA to adipate semialdehyde by an acetylating aldehyde dehydrogenase classified, for example, under EC 1.2.1.10 such as the gene product of PduB or PduP; followed by conversion to 6-aminohexanoate by a ω-transaminase classified, for example, under EC 2.6.1.- (e.g., EC 2.6.1.18, EC 2.6.1.19, EC 2.6.1.29, EC 2.6.1.48, or EC 2.6.1.82) such as from a Chromobacterium *violaceum* (see Genbank Accession No. AAQ59697.1, SEQ ID NO: 13), a *Pseudomonas aeruginosa* co-transaminase (See Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), or a *Vibrio fluvialis* (see Genbank Accession No. AEA39183.1, SEQ ID NO: 18). See, FIG. 4.

In some embodiments, caprolactam is synthesized from 6-aminohexanoate by a 2-hydroxy-cyclohexan-1-one amidohydrolase classified, for example, under EC 3.5.2.-. See, FIG. 4.

Pathway Using 6-Aminohexanoate, 6-Hydroxyhexanoate, or Adipate Semialdehyde as Central Precursor to Hexamethylenediamine In some embodiments, hexamethylenediamine is synthesized from the central precursor 6-aminohexanoate by conversion of 6-aminohexanoate to 6-aminohexanal by a carboxylate reductase (EC 1.2.99.6) such as the gene product of car (see, e.g., SEQ ID NOs: 7 to 12) alongside the gene product of npt, the gene product of GriC & GriD (Suzuki et al., *J. Antibiot.*, 2007, 60(6), 380-387); followed by conversion of 6-aminohexanal to hexamethylenediamine by diamine transaminase (e.g., EC 2.6.1.18, EC 2.6.1.19, EC 2.6.1.29, EC 2.6.1.48, or EC 2.6.1.82). See, FIG. 5.

In some embodiments, hexamethylenediamine is synthesized from the central precursor 6-hydroxyhexanoate (which can be produced as described in FIG. 7), by conversion of 6-hydroxyhexanoate to 6-hydroxyhexanal by a carboxylate reductase classified, for example, under EC 1.2.99.6 such as from a *Mycobacterium marinum* (see Genbank Accession No. ACC40567.1, SEQ ID NO: 7), a *Mycobacterium smegmatis* (see Genbank Accession No. ABK71854.1, SEQ ID NO: 8), a *Segniliparus rugosus* (see Genbank Accession No. EFV11917.1, SEQ ID NO: 9), a *Mycobacterium smegmatis* (see Genbank Accession No. ABK75684.1, SEQ ID NO: 10), a *Mycobacterium massiliense* (see Genbank Accession No. EIV11143.1, SEQ ID NO: 11), or a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*); followed by conversion of 6-hydroxyhexanal to 6-aminohexanol by a ω-transaminase classified, for example, under EC 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas aeruginosa* ω-transaminase (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* ω-transaminase (see Genbank Accession No. AAA57874.1, SEQ ID NO: 17), or a *Vibrio fluvialis* (see Genbank Accession No. AEA39183.1, SEQ ID NO: 18); followed by conversion to 6-aminohexanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (classified, for example, under EC 1.1.1.2, see Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to hexamethylenediamine by a ω-transaminase classified, for example, under EC 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas aeruginosa* ω-transaminase (See Genbank Accession No. AAG08191.1, SEQ ID NO: 14), a *Pseudomonas syringae* (see Genbank Accession No. AAY39893.1, SEQ ID NO: 15), a *Rhodo-* bacter sphaeroides (see Genbank Accession No. ABA81135.1, SEQ ID NO: 16), an *Escherichia coli* a transaminase (see Genbank Accession No. AAA57874.1, SEQ ID NO: 17), or a *Vibrio fluvialis* (see Genbank Accession No. AEA39183.1, SEQ ID NO: 18). See, FIG. 5.

In some embodiments, hexamethylenediamine is synthesized from the central precursor 6-aminohexanoate by conversion of 6-aminohexanoate to N6-acetyl-6-aminohexanoate by an N-acetyltransferase such as a lysine N-acetyltransferase classified, for example, under EC 2.3.1.32; followed by conversion to N6-acetyl-6-aminohexanal by a carboxylate reductase classified, for example, under EC 1.2.99.6 such as from a *Mycobacterium smegmatis* (see Genbank Accession No. ABK71854.1, SEQ ID NO: 8), a *Mycobacterium massiliense* (see Genbank Accession No. EIV11143.1, SEQ ID NO: 11), or a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene product of GriC & GriD (Suzuki et al., *J. Antibiot.*, 2007, 60(6), 380-387); followed by conversion to N6-acetyl-1,6-diaminohexane by a ω-transaminase classified, for example, under EC 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas aeruginosa* ω-transaminase (See Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* ω-transaminase (see Genbank Accession No. AAA57874.1, SEQ ID NO: 17), or a *Vibrio fluvialis* (see Genbank Accession No. AEA39183.1, SEQ ID NO: 18), see above; followed by conversion to hexamethylenediamine by a deacylase classified, for example, under EC 3.5.1.17 or EC 3.5.1.62. See, FIG. 5.

In some embodiments, hexamethylenediamine is synthesized from the central precursor adipate semialdehyde by conversion of adipate semialdehyde to hexanedial by a carboxylate reductase classified, for example, under EC 1.2.99.6 such as from a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene product of GriC & GriD (Suzuki et al., *J. Antibiot.*, 2007, 60(6), 380-387); followed by conversion to 6-aminohexanal by a ω-transaminase classified, for example, under EC 2.6.1.18, EC 2.6.1.19, EC 2.6.1.29, EC 2.6.1.48, or EC 2.6.1.82 such as SEQ ID NOs: 13 to 18; followed by conversion to hexamethylenediamine by a w-transaminase classified, for example, under EC 2.6.1.- such as 2.6.1.18, EC 2.6.1.19, EC 2.6.1.29, EC 2.6.1.48, or EC 2.6.1.82 such as from a Chromobacterium violaceum (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18). See, FIG. 6.

Pathways Using Adipic Acid or Adipyl-CoA as Central Precursor to 6-Hydroxyhexanoate In some embodiments, 6-hydroxyhexanoate is synthesized from the central precursor adipic acid by conversion of adipic acid to adipate semialdehyde by a carboxylate reductase classified, for example, under EC 1.2.99.6 such as from *Segniliparus rugosus* (Genbank Accession No. EFV11917.1, SEQ ID NO: 9) or *Segniliparus rotundus* (Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene products of GriC and GriD from *Streptomyces griseus* (Suzuki et al., J. Antibiot., 2007, 60(6), 380-387); followed by conversion to 6-hydroxyhexanoate by an alcohol dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.-such as the gene product of CpnD (see, for example, Iwaki et al., 2002, *Appl. Environ. Microbiol.*, 68(11):5671-5684), a 5-hydroxypentanoate dehydrogenase from *Clostridium viride*, or a 4-hydroxybutyrate dehydrogenase such as gbd. See, FIG. 7.

In some embodiments, 6-hydroxyhexanoate is synthesized from the central precursor adipyl-CoA by conversion of adipyl-CoA to adipate semialdehyde by an acetylating aldehyde dehydrogenase classified, for example, under EC 1.2.1.10 such as the gene product of PduB or PduP; followed by conversion to 6-hydroxyhexanoate by an alcohol dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD, a 5-hydroxypentanoate dehydrogenase from *Clostridium viride*, or a 4-hydroxybutyrate dehydrogenase such as gbd. See, FIG. 7.

Pathways Using 6-Hydroxyhexanoate as Central Precursor to 1,6-Hexanediol

In some embodiments, 1,6-hexanediol is synthesized from the central precursor, 6-hydroxyhexanoate, by conversion of 6-hydroxyhexanoate to 6-hydroxyhexanal by a carboxylate reductase classified, for example, under EC 1.2.99.6 such as from a *Mycobacterium marinum* (see Genbank Accession No. ACC40567.1, SEQ ID NO: 7), a *Mycobacterium smegmatis* (see Genbank Accession No. ABK71854.1, SEQ ID NO: 8), a *Segniliparus rugosus* (see Genbank Accession No. EFV11917.1, SEQ ID NO: 9), a *Mycobacterium smegmatis* (see Genbank Accession No. ABK75684.1, SEQ ID NO: 10), a *Mycobacterium* massiliense (see Genbank Accession No. EIV11143.1, SEQ ID NO: 11), or a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene product of GriC & GriD (Suzuki et al., J. Antibiot., 2007, 60(6), 380-387); followed by conversion of 6-hydroxyhexanal to 1,6 hexanediol by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (classified, for example, under EC 1.1.1.2, see Genbank Accession No.

CAA90836.1) or YqhD (from *E. coli*, GenBank Accession No. AAA69178.1) (Liu et al., Microbiology, 2009, 155, 2078-2085). See FIG. 8.

Cultivation Strategy

In some embodiments, the cultivation strategy entails achieving an aerobic, anaerobic, micro-aerobic, or mixed oxygen/denitrification cultivation condition. Enzymes characterized in vitro as being oxygen sensitive require a micro-aerobic cultivation strategy maintaining a very low dissolved oxygen concentration (See, for example, Chayabatra & Lu-Kwang, *Appl. Environ. Microbiol.*, 2000, 66(2), 493 0 498; Wilson and Bouwer, 1997, *Journal of Industrial Microbiology and Biotechnology*, 18(2-3), 116-130).

In some embodiments, the cultivation strategy entails nutrient limitation such as nitrogen, phosphate or oxygen limitation.

In some embodiments, a cell retention strategy using, for example, ceramic membranes is employed to achieve and maintain a high cell density during either fed-batch or continuous fermentation.

In some embodiments, the principal carbon source fed to the fermentation in the synthesis of a C6 building block derives from biological or non-biological feedstocks.

In some embodiments, the biological feedstock is, includes, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., App. Biochem. Biotechnol., 2012, 166, 1801-1813; Yang et al., *Biotechnology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such as benzoate analogs has been demonstrated in several microorganisms such as *Pseudomonas putida, Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock is or derives from natural gas, syngas, CO2/H2, methanol, ethanol, benzoate, non-volatile residue (NVR) caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ram say et al., *Applied and Environmental Microbiology*, 1986, 52(1), 152-156).

In some embodiments, the host microorganism is a prokaryote. For example, the prokaryote can be from the genus *Escherichia* such as *Escherichia coli*; from the genus *Clostridia* such as *Clostridium ljungdahlii, Clostridium autoethanogenum* or *Clostridium klhuyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C6 building blocks.

In some embodiments, the host microorganism is a eukaryote. For example, the eukaryote can be from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C6 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined in section 4.5 are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined in section 4.5 are gene dosed (i.e., overexpressed by having a plurality of copies of the gene in the host organism), into the resulting genetically modified organism via episomal or chromosomal integration approaches.

In some embodiments, genome-scale system biology techniques such as Flux Balance Analysis are utilized to devise genome scale attenuation or knockout strategies for directing carbon flux to a C6 building block.

Attenuation strategies include, but are not limited to; the use of transposons, homologous recombination (double cross-over approach), mutagenesis, enzyme inhibitors and RNA interference (RNAi).

In some embodiments, fluxomic, metabolomic and transcriptomal data are utilized to inform or support genome-scale system biology techniques, thereby devising genome scale attenuation or knockout strategies in directing carbon flux to a C6 building block.

In some embodiments, the host microorganism's tolerance to high concentrations of a C6 building block is improved through continuous cultivation in a selective environment.

In some embodiments, the turnover or activity of the methyl transferase such as the gene product of bioC is increased through enzyme engineering.

In some embodiments, the genes encoding enzymes required for efficient methanol metabolism, such as alcohol oxidase, formaldehyde dehydrogenase, or formate dehydrogenase, are gene dosed into the host microorganism.

In some embodiments, the host microorganism's endogenous biochemical network is attenuated or augmented to (1) ensure the intracellular availability of 2-oxoglutarate, (2) create a NADPH imbalance that may be balanced via the formation of a C6 building block, (3) prevent degradation of central metabolites or central precursors leading to and including C6 building blocks and (4) ensure efficient efflux from the cell.

In some embodiments requiring the intracellular availability of 2-oxo-glutarate, a PEP carboxykinase or PEP carboxylase can be overexpressed in the host to generate anaplerotic carbon flux into the Krebs cycle towards 2-oxo-glutarate (Schwartz et al., 2009, *Proteomics*, 9, 5132-5142).

In some embodiments requiring the intracellular availability of 2-oxo-glutarate, a pyruvate carboxylase can be overexpressed in the host to generated anaplerotic carbon flux into the Krebs cycle towards 2-oxoglutarate (Schwartz et al., 2009, *Proteomics*, 9, 5132-5142).

In some embodiments requiring the intracellular availability of 2-oxo-glutarate, a PEP synthase can be overexpressed in the host to enhance the flux from pyruvate to PEP, thus increasing the carbon flux into the Krebs cycle via PEP carboxykinase or PEP carboxylase (Schwartz et al., 2009, *Proteomics*, 9, 5132-5142).

In some embodiments requiring the intracellular availability of 2-oxoglutarate for C6 building block synthesis, anaplerotic reactions enzymes such as phosphoenolpyruvate carboxylase (e.g., the gene product of pck), phosphoenolpyruvate carboxykinase (e.g., the gene product of ppc), the malic enzyme (e.g., the gene product of sfcA) and/or pyruvate carboxylase are overexpressed in the host organisms (Song and Lee, 2006, Enzyme Micr. Technol., 39, 352-361).

In some embodiments requiring intracellular availability of acetyl-CoA, endogenous enzymes catalyzing the hydrolysis of acetyl-CoA such as short-chain length thioesterases (e.g., an acetyl-CoA thioesterase) can be attenuated in the host organism.

In some embodiments requiring condensation of acetyl-CoA for C7 building block synthesis, one or more endogenous β-ketothiolases catalyzing the condensation of only acetyl-CoA to acetoacetyl-CoA such as the endogenous gene products of AtoB or phaA can be attenuated.

In some embodiments requiring the intracellular availability of acetyl-CoA for C6 building block synthesis, an endogenous gene encoding a phosphotransacetylase that generates acetate, such as pta, is attenuated (Shen et al., *Appl. Environ. Microbiol.*, 2011, 77(9), 2905-2915).

In some embodiments requiring the intracellular availability acetyl-CoA for C6 building block synthesis, an endogenous gene encoding an acetate kinase in an acetate synthesis pathway, such as ack, is attenuated.

In some embodiments, requiring the intracellular availability of Krebs cycle intermediates for C6 building block synthesis, pyruvate:formate lyase (e.g., the gene product of pfl) is attenuated (Song and Lee, 2006, Enzyme Micr. Technol., 39, 352-361).

In some embodiments requiring the intracellular availability of acetyl-CoA for C6 building block synthesis, an endogenous gene encoding an enzyme that catalyzes the degradation of pyruvate to lactate such as ldhA is attenuated (Shen et al., *Appl. Environ. Microbiol.*, 2011, 77(9), 2905-2915).

In some embodiments requiring the intracellular availability of Krebs cycle intermediates for C6 building block synthesis, 2-oxoglutarate dehydrogenase is attenuated in one or more of its subunits.

In some embodiments requiring intracellular availability of Krebs cycle intermediates for C6 building block synthesis, the regulator of 2-oxoglutarate dehydrogenase is overexpressed by induction in the host microorganism.

In some embodiments requiring the intracellular availability of acetyl-CoA intermediates and NADH for C6 building block synthesis, endogenous genes encoding enzymes that catalyze the degradation of phosphoenolpyruvate to succinate such as frdBC are attenuated (see, e.g., Shen et al., 2011, supra).

In some embodiments requiring the intracellular availability of acetyl-CoA for C6 building block synthesis, an endogenous gene encoding an enzyme that catalyzes the degradation of acetyl-CoA to ethanol such as the alcohol dehydrogenase encoded by adhE is attenuated (Shen et al., 2011, supra).

In some embodiments where the host microorganism uses the lysine biosynthesis pathway via meso-2,6-diaminopimelate, the genes encoding the synthesis of 2-oxoadipate from 2-oxoglutarate are gene dosed into the host.

In some embodiments where the host microorganism uses the lysine biosynthesis pathway via 2-oxoadipate, the genes encoding the synthesis of lysine via meso-2,6-diaminopimelate are gene dosed into the host.

In some embodiments, an endogenous gene encoding an enzyme that catalyzes the degradation of pyruvate to ethanol such as pyruvate decarboxylase is attenuated.

In some embodiments, where pathways require excess NADPH or NADH co-factor for C7 building block synthesis, an endogenous transhydrogenase such as one classified under EC 1.6.1.1, EC 1.6.1.2 or EC 1.6.1.3, dissipating the co-factor imbalance can be attenuated.

In some embodiments, where pathways require excess NADPH co-factor for C7 building block synthesis, an exogenous transhydrogenase such as one classified under EC 1.6.1.1, EC 1.6.1.2 or EC 1.6.1.3, converting NADH to NADPH can be overexpressed.

In some embodiments, endogenous genes encoding enzymes facilitating the conversion of NADPH to NADH are attenuated, such as the NADH generation cycle that may be generated via inter-conversion of glutamate dehydrogenases in EC 1.4.1.2 (NADH-specific) and EC 1.4.1.4 (NADPH-specific).

In some embodiments, an endogenous gene encoding a glutamate dehydrogenases (EC 1.4.1.3) that utilizes both NADH and NADPH are co-factors is attenuated.

In some embodiments using hosts that naturally accumulate polyhydroxyalkanoates, an endogenous gene encoding a polyhydroxyalkanoate synthase can be attenuated in the host strain.

In some embodiments using hosts that naturally accumulate lipid bodies, the genes encoding enzymes involved with lipid body synthesis are attenuated.

In some embodiments requiring the intracellular availability of acetyl-CoA for C7 building block synthesis, a recombinant acetyl-CoA synthetase such as the gene product of acs can be overexpressed in the microorganism (Satoh et al., *J. Bioscience and Bioengineering,* 2003, 95(4):335-341).

In some embodiments, an L-alanine dehydrogenase can be overexpressed in the host to regenerate L-alanine from pyruvate as amino donor for ω-transaminase reactions.

In some embodiments, a NADH-specific L-glutamate dehydrogenase can be overexpressed in the host to regenerate L-glutamate from 2-oxo-glutarate as amino donor for ω-transaminase reactions.

In some embodiments, enzymes such as pimeloyl-CoA dehydrogenase classified under, for example, EC 1.3.1.62; an acyl-CoA dehydrogenase classified under, for example, EC 1.3.8.7 or EC 1.3.8.1; and/or a glutaryl-CoA dehydrogenase classified under, for example, EC 1.3.8.6 that degrade central metabolites and central precursors leading to and including C7 building blocks can be attenuated.

In some embodiments, endogenous enzymes activating C7 building blocks via Coenzyme A esterification such as CoA-ligases such as pimeloyl-CoA synthetase classified under, for example, EC 6.2.1.14 can be attenuated.

In some embodiments requiring the intracellular availability of acetyl-CoA for C7 building block synthesis, a recombinant acetyl-CoA synthetase such as the gene product of acs can be overexpressed in the microorganism (Satoh et al., *J. Bioscience and Bioengineering,* 2003, 95(4):335-341).

In some embodiments, an L-alanine dehydrogenase can be overexpressed in the host to regenerate L-alanine from pyruvate as amino donor for ω-transaminase reactions.

In some embodiments, a NADPH-specific L-glutamate dehydrogenase can be overexpressed in the host to regenerate L-glutamate from 2-oxo-glutarate as amino donor for ω-transaminase reactions.

In some embodiments, enzymes such as pimeloyl-CoA dehydrogenase classified under, for example, EC 1.3.1.62; an acyl-CoA dehydrogenase classified under, for example, EC 1.3.8.7 or EC 1.3.8.1; and/or a glutaryl-CoA dehydrogenase classified under, for example, EC 1.3.8.6 that degrade central metabolites and central precursors leading to and including C6 building blocks can be attenuated.

In some embodiments, endogenous enzymes activating C6 building blocks via Coenzyme A esterification such as CoA-ligases such as pimeloyl-CoA synthetase classified under, for example, EC 6.2.1.14 can be attenuated.

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress,* 19(5), 1444-1449).

In some embodiments, where pathways require excess NADPH co-factor in the synthesis of a C6 building block, a gene such as UdhA encoding a puridine nucleotide transhydrogenase can be overexpressed in the host organisms (Brigham et al., *Advanced Biofuels and Bioproducts,* 2012, Chapter 39, 1065-1090).

In some embodiments, where pathways require excess NADPH co-factor in the synthesis of a C6 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C6 building block, a recombinant malic enzyme gene such as maeA or maeB can be overexpressed in the host organisms (Brigham et al., 2012, supra).

In some embodiments, where pathways require excess NADPH co-factor in the synthesis of a C6 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C6 building block, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C6 building block, endogenous triose phosphate isomerase (EC 5.3.1.1) can be attenuated.

In some embodiments, where pathways require excess NADPH co-factor in the synthesis of a C6 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific). For example, avoiding dissipation of an NADPH imbalance towards C6 building blocks, a NADH-specific glutamate dehydrogenase can be attenuated.

In some embodiments, an endogenous glutamate dehydrogenase (EC 1.4.1.3) that utilizes both NADH and NADPH as co-factors can be attenuated.

In some embodiments, a methanol dehydrogenase or a formaldehyde dehydrogenase can be overexpressed in the host to allow methanol catabolism via formate.

In some embodiments, a S-adenosylmethionine synthetase can be overexpressed in the host to generate S-adenosyl-L-methionine as a co-factor for a fatty acid O-methyltransferase.

In some embodiments, one or more of 3-phosphoglycerate dehydrogenase, 3-phosphoserine aminotransferase and phohosphoserine phosphatase can be overexpressed in the host to generate serine as a methyl donor for the S-adenosyl-L-methionine cycle.

In some embodiments, a membrane-bound enoyl-CoA reductases can be solubilized via expression as a fusion protein to a small soluble protein such as a maltose binding protein (Gloerich et al., *FEBS Letters*, 2006, 580, 2092-2096).

In some embodiments, the efflux of a C6 building block across the cell membrane to the extracellular media can be enhanced or amplified by genetically engineering structural modifications to the cell membrane or increasing any associated transporter activity for a C6 building block.

The efflux of hexamethylenediamine can be enhanced or amplified by overexpressing broad substrate range multi-drug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499) or NorA from *Staphylococcus aereus* (Ng et al., 1994, *Antimicrob Agents Chemother*, 38(6), 1345-1355) or Bmr from *Bacillus subtilis* (Neyfakh, 1992, *Antimicrob Agents Chemother*, 36(2), 484-485).

The efflux of 6-aminohexanoate and hexamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of adipic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C6 Building Blocks Using a Recombinant Host

Typically, one or more C6 building blocks can be produced by providing a host microorganism and culturing the provided microorganism with a culture medium containing a suitable carbon source as described above. In general, the culture media and/or culture conditions can be such that the microorganisms grow to an adequate density and produce a C6 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C6 building block. Once produced, any method can be used to isolate C6 building blocks. For example, C6 building blocks can be recovered selectively from the fermentation broth via adsorption processes. In the case of adipic acid and 6-aminohexanoate, the resulting eluate can be further concentrated via evaporation, crystallized via evaporative and/or cooling crystallization, and the crystals recovered via centrifugation. In the case of hexamethylenediamine and 6-hydroxyhexanoate, distillation may be employed to achieve the desired product purity.

Accordingly, the methods provided herein can be performed in a recombinant host. In some embodiments, the methods provided herein can be performed in a recombinant host by fermentation. In some embodiments, the recombinant host is subjected to a cultivation strategy under aerobic, anaerobic or, micro-aerobic cultivation conditions. In some embodiments, the recombinant host is cultured under conditions of nutrient limitation such as phosphate, nitrogen and oxygen limitation. In some embodiments, the recombinant host is retained using a ceramic membrane to maintain a high cell density during fermentation.

In some embodiments, the principal carbon source fed to the fermentation derives from biological or non-biological feedstocks. In some embodiments, the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste. In some embodiments, the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

In some embodiments, the recombinant host is a prokaryote. In some embodiments, the prokaryote is from the genus *Escherichia* such as *Escherichia coli*; from the genus *Clostridia* such as *Clostridium ljungdahlii*, *Clostridium autoethanogenum* or *Clostridium kluyveri*; from the genus

*Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis*; or from the genus *Rhodococcus* such as *Rhodococcus equi*.

In some embodiments, the recombinant host is a eukaryote. In some embodiments, the eukaryote is from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxrula adenoinivorans*, or from the genus *Kluyveromyces* such as *Kluyveromyces lactis*.

In some embodiments, the recombinant host includes one or more of the following attenuated enzymes: a polypeptide having polyhydroxyalkanoate synthase, acetyl-CoA thioesterase, acetyl-CoA specific β-ketothiolase, phosphotransacetylase forming acetate, acetate kinase, lactate dehydrogenase, menaquinol-fumarate oxidoreductase, alcohol dehydrogenase forming ethanol, triose phosphate isomerase, pyruvate decarboxylase, glucose-6-phosphate isomerase, transhydrogenase dissipating a NADPH imbalance, glutamate dehydrogenase dissipating a NADPH imbalance, NADH/NADPH-utilizing glutamate dehydrogenase, pimeloyl-CoA dehydrogenase; acyl-CoA dehydrogenase accepting C7 building blocks and central precursors as substrates; glutaryl-CoA dehydrogenase; or adipyl-CoA synthetase activity.

In some embodiments, the recombinant host overexpresses one or more genes encoding: a polypeptide having acetyl-CoA synthetase; 6-phosphogluconate dehydrogenase; transketolase; puridine nucleotide transhydrogenase; formate dehydrogenase; glyceraldehyde-3P-dehydrogenase; malic enzyme; glucose-6-phosphate dehydrogenase; fructose 1,6 diphosphatase; L-alanine dehydrogenase; PEP carboxylase, pyruvate carboxylase; PEP carboxykinase; PEP synthase; L-glutamate dehydrogenase specific to the NADPH used to generate a co-factor imbalance; methanol dehydrogenase, formaldehyde dehydrogenase, lysine transporter; dicarboxylate transporter; S-adenosylmethionine synthetase; 3-phosphoglycerate dehydrogenase; 3-phosphoserine aminotransferase; phosphoserine phosphatase; or a multidrug transporter activity.

The present document further provides a recombinant host comprising an exogenous nucleic acid encoding a polypeptide having fatty acid O-methyltransferase activity, the host producing 2,3-dehydroadipate methyl ester.

In some embodiments, the recombinant host further includes an exogenous polypeptide having thioesterase activity.

In some embodiments, the recombinant host further includes an exogenous polypeptide having CoA ligase activity, the host further producing 2,3-dehydroadipyl-CoA methyl ester.

In some embodiments, the recombinant host further includes an exogenous polypeptide having trans-2-enoyl-CoA reductase activity, the host further producing adipyl-CoA methyl ester and/or an exogenous polypeptide having pimeloyl-[acp] methyl ester methylesterase activity, the host further producing adipyl-CoA.

In some embodiments, the recombinant host further includes one or more exogenous polypeptides having homocitrate synthase, homocitrate dehydratase, homoaconitate hydratase, isohomocitrate dehydrogenase, decarboxylase, indolepyruvate decarboxylase, glutarate-semialdehyde dehydrogenase, or glutarate:CoA ligase activity.

In some embodiments, the recombinant host further includes one or more exogenous polypeptides selected from the group consisting of polypeptides having (a) β-ketothiolase activity or acetyl-carboxylase activity in combination with acetoacetyl-CoA synthase activity, (b) 3-hydroxybutyryl-CoA dehydrogenase activity, (c) enoyl-CoA hydratase activity, and either (d) glutaryl-CoA dehydrogenase activity in combination with enoyl-CoA reductase activity or trans-2-enoyl-CoA reductase activity or (e) glutaconyl-CoA decarboxylase activity.

In some embodiments, the recombinant host further includes one or more exogenous polypeptides having (i) β-ketoacyl-[acp] synthase activity or β-ketothiolase activity, (ii) 3-hydroxybutyryl-CoA dehydrogenase activity, and (iii) enoyl-CoA hydratase activity.

In some embodiments, the recombinant host further includes one or more exogenous polypeptides having homocitrate synthase, homocitrate dehydratase, homoaconitate hydratase, isohomocitrate dehydrogenase, 2-hydroxyglutarate dehydrogenase, glutaconate CoA-transferase, or 2-hydroxyglutaryl-CoA dehydratase activity.

In some embodiments, the recombinant host further includes one or more exogenous polypeptides having thioesterase, aldehyde dehydrogenase, 7-oxoheptanoate dehydrogenase, 6-oxohexanoate dehydrogenase, glutaconate CoA-transferase, reversible succinyl-CoA ligase, acetylating aldehyde dehydrogenase, or carboxylate reductase activity, the host further producing adipic acid or adipate semialdehyde.

In some embodiments, the recombinant host further includes an exogenous polypeptide having ω-transaminase activity, the host further producing 6-aminohexanoate.

In some embodiments, the recombinant host further includes one or more exogenous polypeptides having 4-hydroxybutyrate dehydrogenase, 5-hydroxypentanoate dehydrogenase, 6-hydroxyhexanoate dehydrogenase, or alcohol dehydrogenase activity, the host further producing 6-hydroxyhexanoic acid.

In some embodiments, the recombinant host further includes one or more exogenous polypeptides having ω-transaminase, deacetylase, N-acetyl transferase, or alcohol dehydrogenase activity, the host further producing hexamethylenediamine.

In some embodiments, the recombinant host further includes one or more exogenous polypeptides having (a) carboxylate reductase activity enhanced by phosphopantetheinyl transferase activity, or (b) alcohol dehydrogenase activity, the host further producing 1,6-hexanediol.

EXAMPLES

Example 1

Enzyme Activity of Thioesterases Using Adipyl-CoA as a Substrate and Forming Adipate A sequence encoding an N-terminal His-tag was added to the genes from *Escherichia coli* encoding the thioesterases of SEQ ID NO: 21 and SEQ ID NO: 28 (see FIGS. 9L and 9P), such that an N-terminal HIS tagged thioesterase could be produced. Each of the resulting modified genes was cloned into a pET15b expression vector under control of the T7 promoter. Each expression vector was transformed into a BL21 [DE3]*E. coli* host. The resulting recombinant *E. coli* strains were cultivated at 37° C. in a 500 mL shake flask culture containing 50 mL Luria Broth (LB) media and antibiotic selection pressure, with shaking at 230 rpm. The culture was induced overnight at 17° C. using 0.5 mM IPTG.

The pellet from the induced shake flask culture was harvested via centrifugation. The pellet was resuspended and lysed in Y-Per™ solution (ThermoScientific, Rockford, Ill.). The cell debris was separated from the supernatant via centrifugation. The thioesterases were purified from the supernatant using Ni-affinity chromatography and the eluate was buffer exchanged and concentrated via ultrafiltration.

Figure 21:
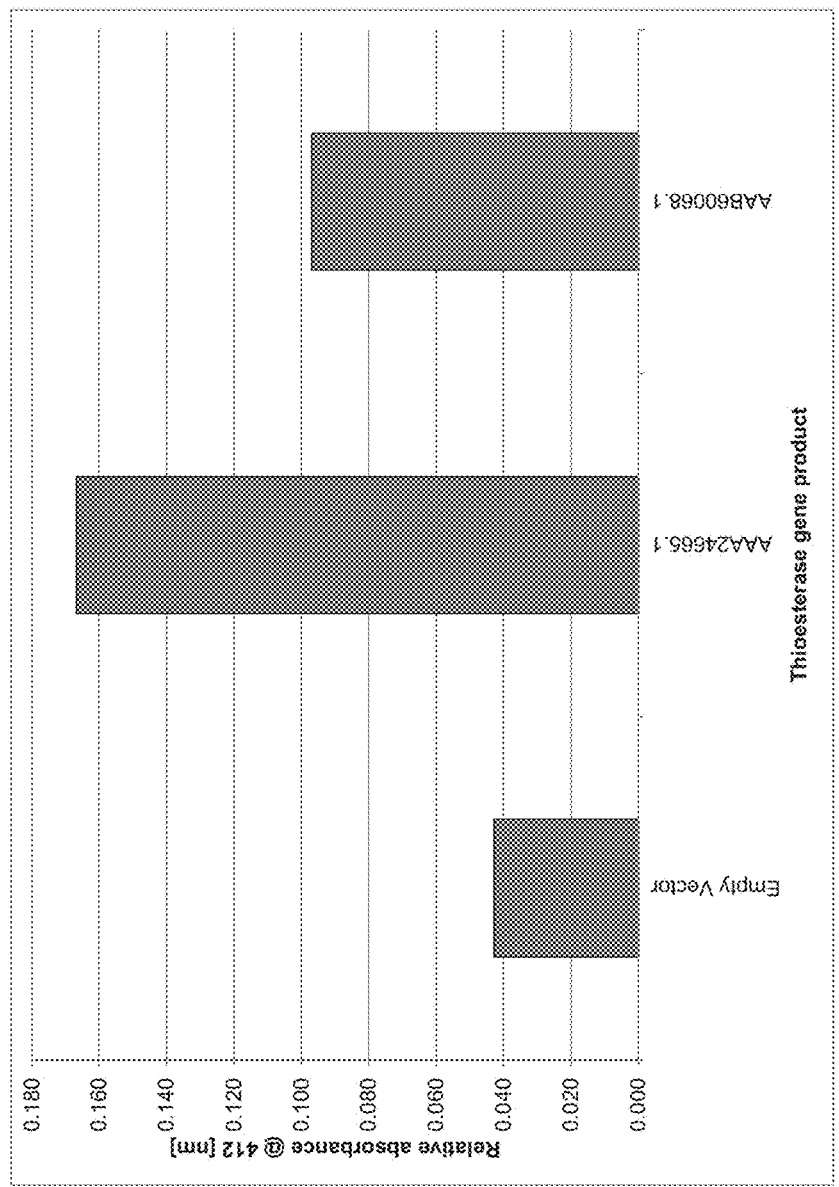
FIG. 21 is a bar graph of the relative absorbance at 412 nm after 20 minutes of released CoA as a measure of the activity of a thioesterase for converting adipyl-CoA to adipate relative to the empty vector control.

The enzyme activity assay was performed in triplicate in a buffer composed of 50 mM phosphate buffer (pH=7.4), 0.1 mM Ellman's reagent, and 667 µM of adipyl-CoA (as substrate). Each enzyme activity assay reaction was initiated by adding 0.8 µM of the gene product of SEQ ID NO: 21 and 4.1 µM of the gene product of SEQ ID NO: 28 to the assay buffer containing the adipyl-CoA and incubating at 37° C. for 20 min. The release of Coenzyme A was monitored by absorbance at 412 nm. The absorbance associated with the substrate only control, which contained boiled enzyme, was subtracted from the active enzyme assay absorbance and compared to the empty vector control. The gene product of SEQ ID NO: 21 and SEQ ID NO: 28 accepted adipyl-CoA as substrate as confirmed via relative spectrophotometry (see, FIG. 21) and synthesized adipate as a reaction product.

Example 2

Enzyme Activity of ω-Transaminase Using Adipate Semialdehyde as Substrate and Forming 6-Aminohexanoate A nucleotide sequence encoding a His-tag was added to the genes from *Chromobacterium violaceum, Pseudomonas aeruginosa, Pseudomonas syringae, Rhodobacter sphaeroides*, and *Vibrio Fluvialis* encoding the ω-transaminases of SEQ ID NOs: 13, 14, 15, 16, and 18, respectively (see FIGS. 9J-9K) such that N-terminal HIS tagged ω-transaminases could be produced. Each of the resulting modified genes was cloned into a pET21a expression vector under control of the T7 promoter and each expression vector was transformed into a BL21 [DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanoate to adipate semialdehyde) were performed in a buffer composed of a final concentration of 50 mM HEPES buffer (pH=7.5), 10 mM 6-aminohexanoate, 10 mM pyruvate and 100 µM pyridoxyl 5' phosphate. Each enzyme activity assay reaction was initiated by adding cell free extract of the ω-transaminase gene product or the empty vector control to the assay buffer containing the 6-aminohexanoate and incubated at 25° C. for 24 h, with shaking at 250 rpm. The formation of L-alanine from pyruvate was quantified via RP-HPLC.

Figure 14:
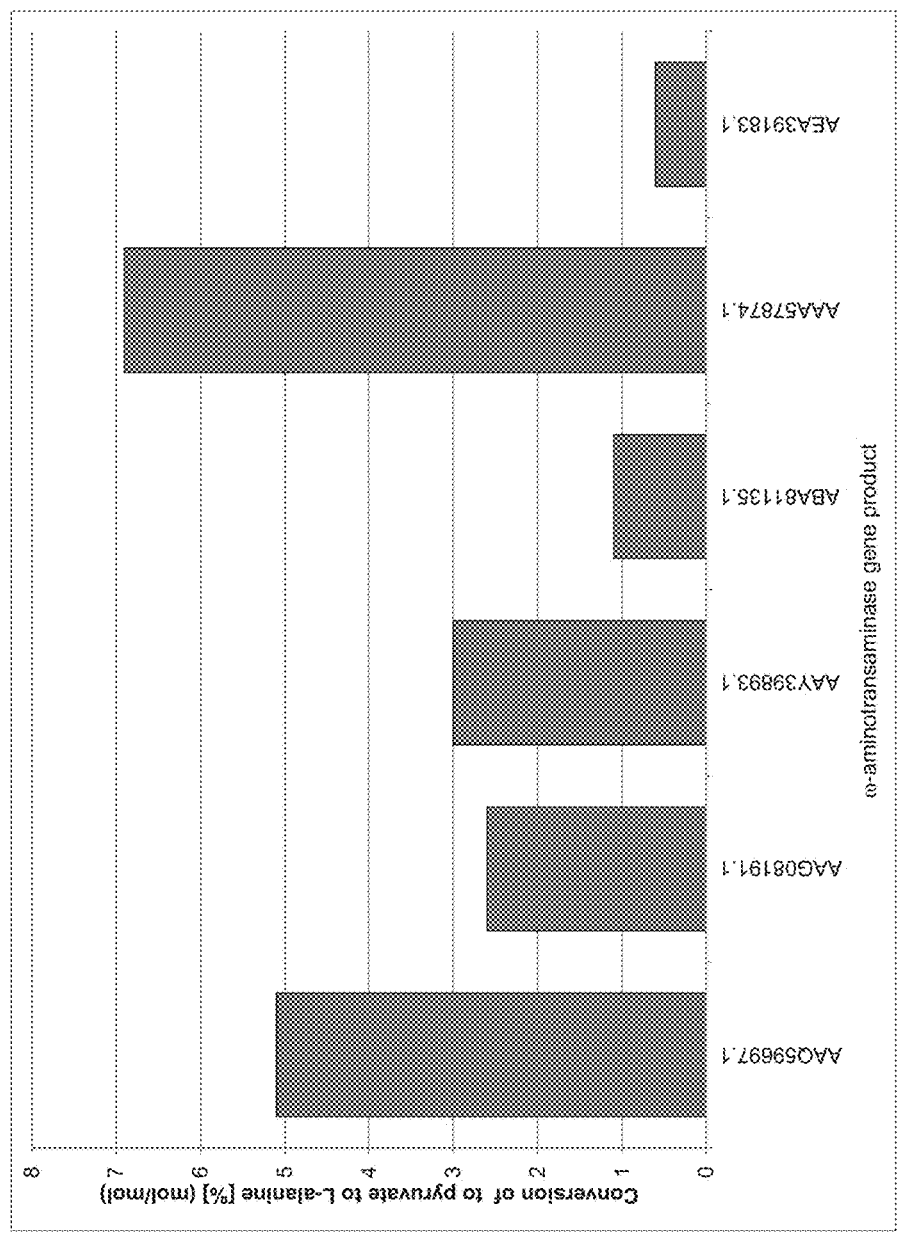
FIG. 14 is a bar graph summarizing the percent conversion after 4 hours of pyruvate to L-alanine (mol/mol) as a measure of the ω-transaminase activity of the enzyme only controls (no substrate).
Figure 15:
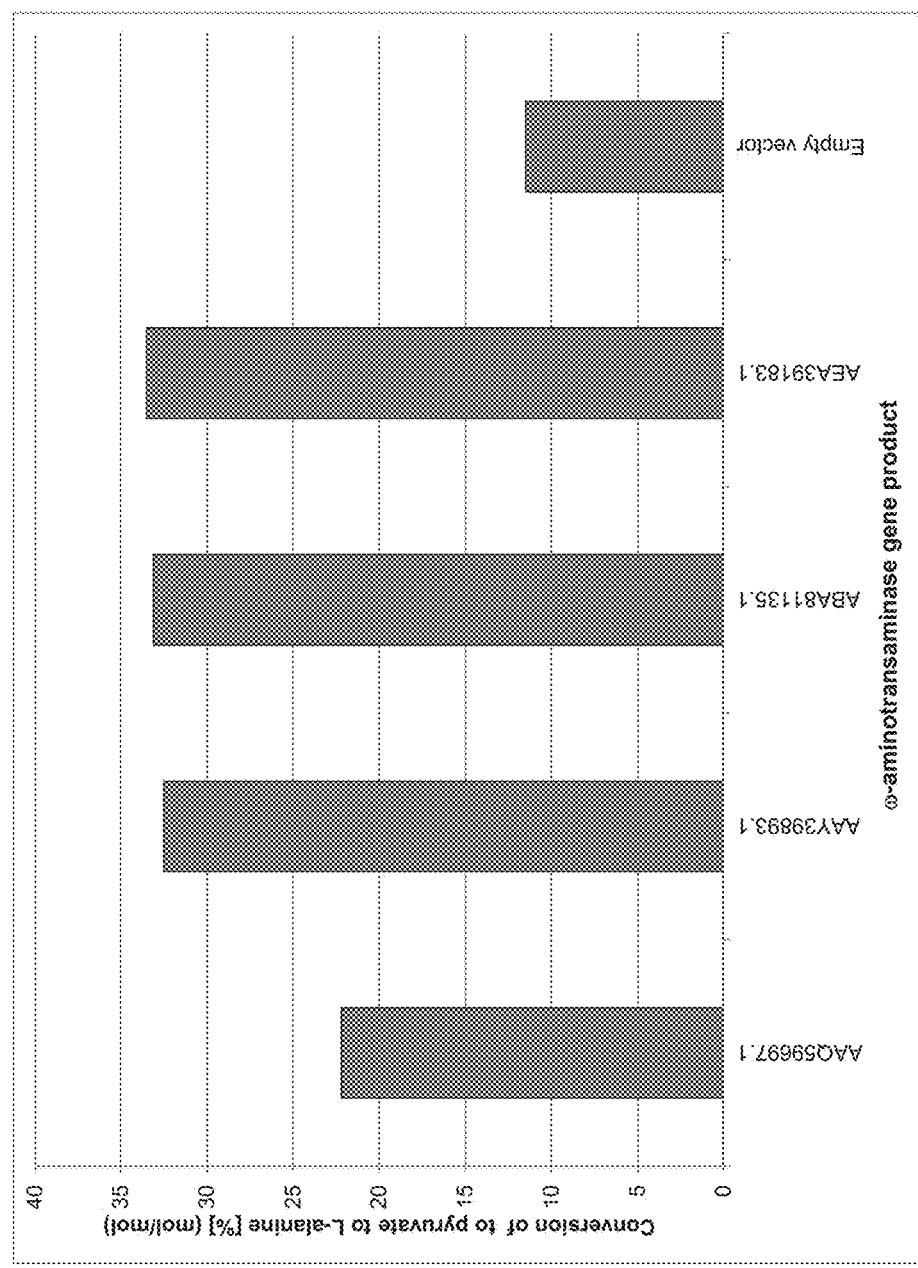
FIG. 15 is a bar graph of the percent conversion after 24 hours of pyruvate to L-alanine (mol/mol) as a measure of the ω-transaminase activity for converting 6-aminohexanoate to adipate semialdehyde relative to the empty vector control.

Each enzyme only control without 6-aminohexanoate demonstrated low base line conversion of pyruvate to L-alanine. See FIG. 14. The gene product of SEQ ID NO: 13, SEQ ID NO: 15, SEQ ID NO: 16 and SEQ ID NO: 18 accepted 6-aminohexanote as substrate as confirmed against the empty vector control. See, FIG. 15.

Enzyme activity in the forward direction (i.e., adipate semialdehyde to 6-aminohexanoate) was confirmed for the transaminases of SEQ ID NO: 13, SEQ ID NO: 14, SEQ ID NO: 15, SEQ ID NO: 16 and SEQ ID NO: 18. Enzyme activity assays were performed in a buffer composed of a final concentration of 50 mM HEPES buffer (pH=7.5), 10 mM adipate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the adipate semialdehyde and incubated at 25° C. for 4 hours, with shaking at 250 rpm. The formation of pyruvate was quantified via RP-HPLC.

Figure 16:
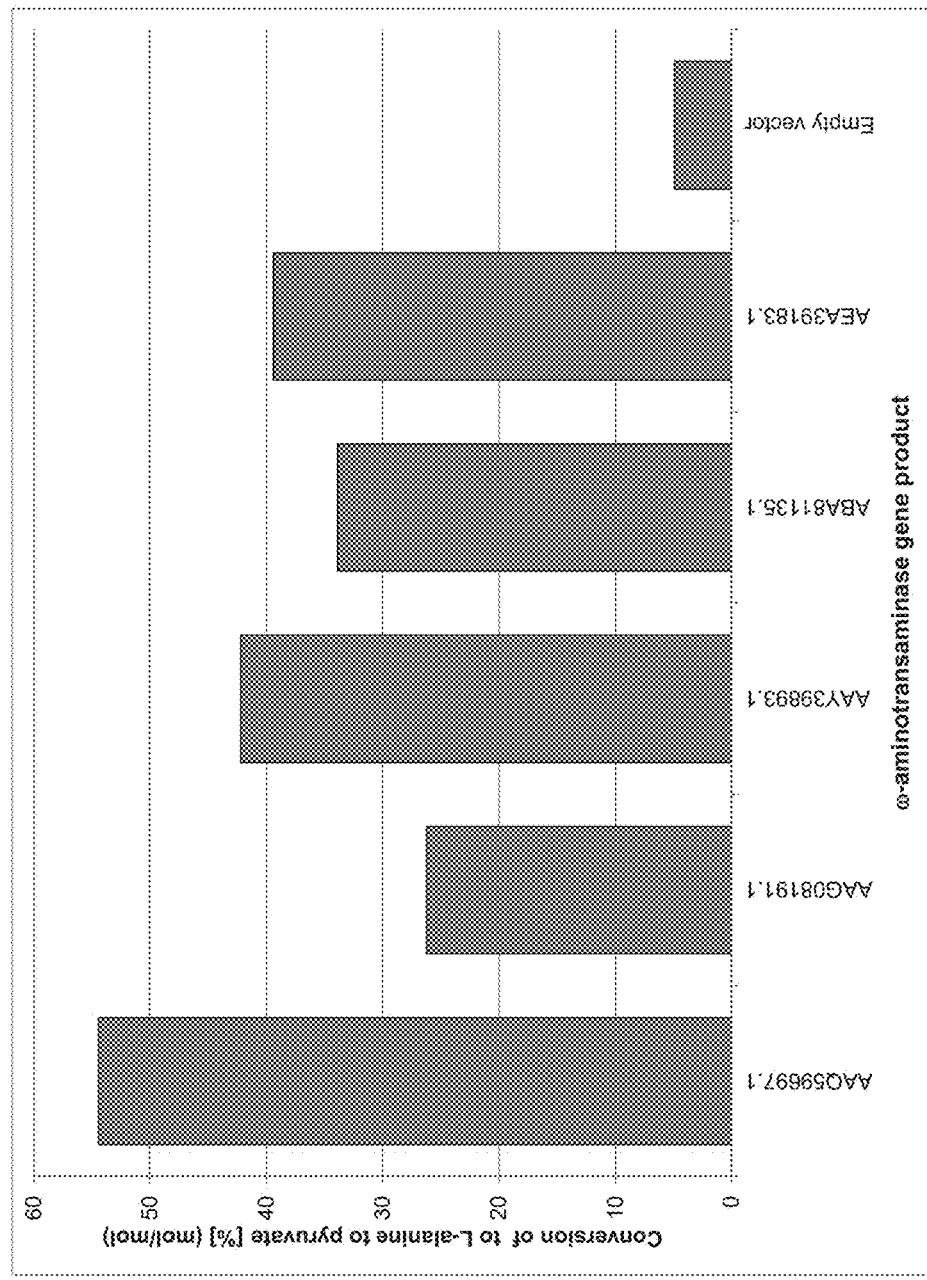
FIG. 16 is a bar graph of the percent conversion after 4 hours of L-alanine to pyruvate (mol/mol) as a measure of the ω-transaminase activity for converting adipate semialdehyde to 6-aminohexanoate relative to the empty vector control.

The gene product of SEQ ID NO: 13, SEQ ID NO: 14, SEQ ID NO: 15, SEQ ID NO: 16 and SEQ ID NO: 18 accepted adipate semialdehyde as substrate as confirmed against the empty vector control. See, FIG. 16. The reversibility of the ω-transaminase activity was confirmed, demonstrating that the ω-transaminases of SEQ ID NO: 13, SEQ ID NO: 14, SEQ ID NO: 15, SEQ ID NO: 16 and SEQ ID NO: 18 accepted adipate semialdehyde as substrate and synthesized 6-aminohexanoate as a reaction product.

Example 3

Enzyme Activity of Carboxylate Reductase Using Adipate as Substrate and Forming Adipate Semialdehyde A nucleotide sequence encoding a HIS-tag was added to the genes from *Segniliparus rugosus* and *Segniliparus rotundus* that encode the carboxylate reductases of SEQ ID NOs: 9 and 12, respectively (see FIGS. 9F and 9I), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21 [DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Figure 22:
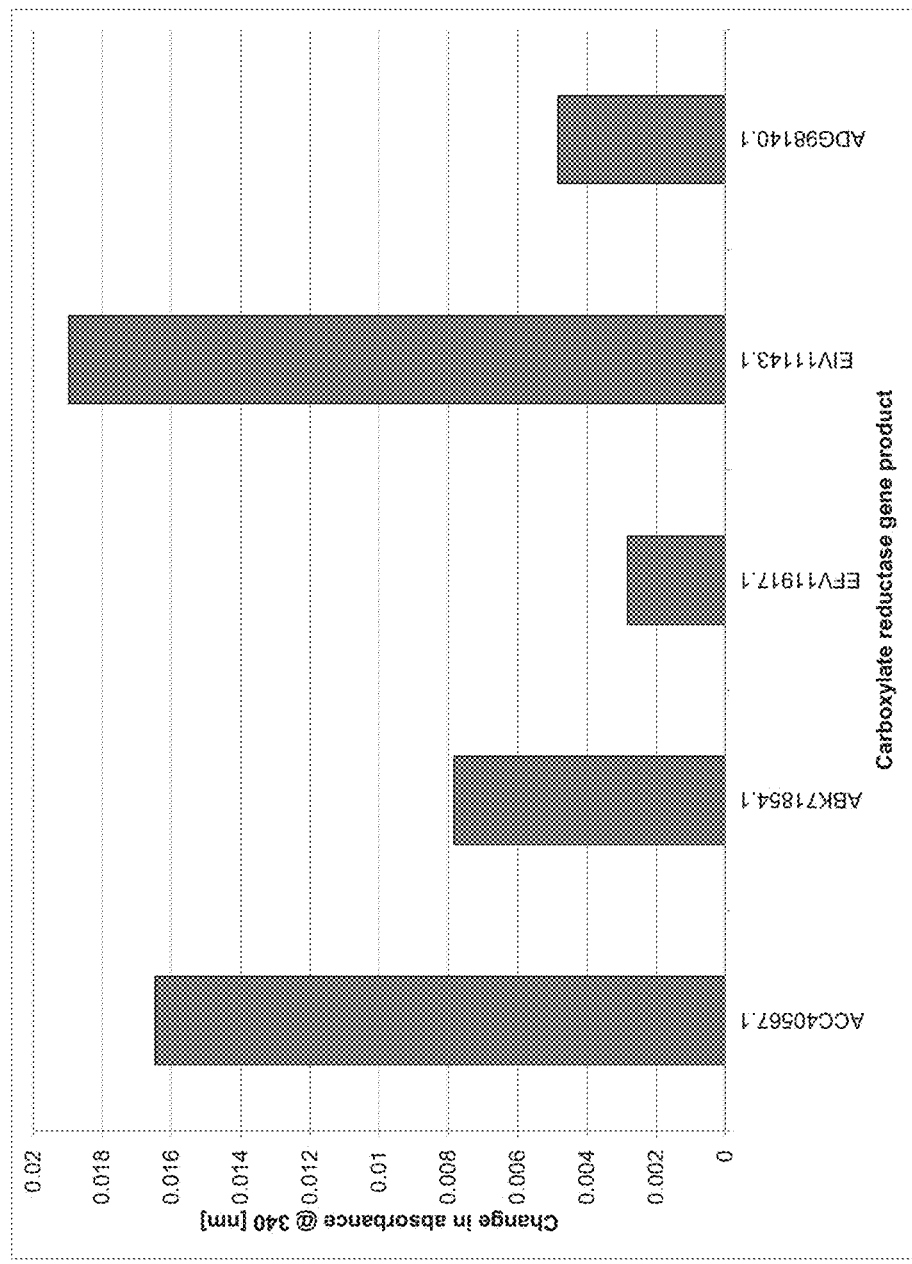
FIG. 22 is a bar graph summarizing the change in absorbance at 340 nm after 20 minutes, which is a measure of the consumption of NADPH and activity of carboxylate reductases relative to the enzyme only controls (no substrate).

Enzyme activity assays (i.e., from adipate to adipate semialdehyde) were performed in triplicate in a buffer composed of a final concentration of 50 mM HEPES buffer (pH=7.5), 2 mM adipate, 10 mM $MgCl_2$, 1 mM ATP, and 1 mM NADPH. Each enzyme activity assay reaction was initiated by adding purified carboxylate reductase and phosphopantetheine transferase gene products or the empty vector control to the assay buffer containing the adipate and then incubated at room temperature for 20 minutes. The consumption of NADPH was monitored by absorbance at 340 nm. Each enzyme only control without adipate demonstrated low base line consumption of NADPH. See, FIG. 22.

Figure 10:
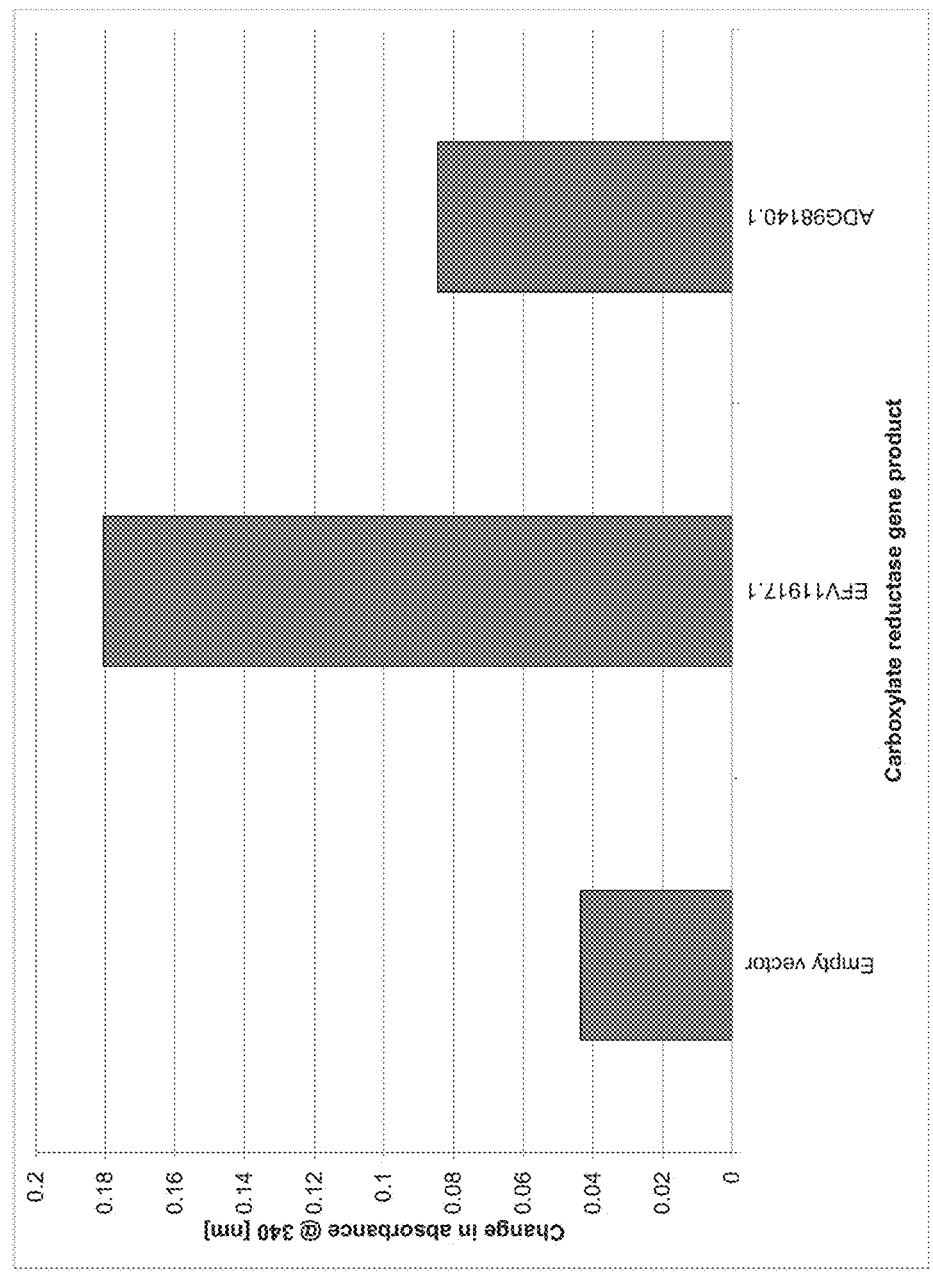
FIG. 10 is a bar graph of the change in absorbance at 340 nm after 20 minutes, which is a measure of the consumption of NADPH and the activity of carboxylate reductases for converting adipate to adipate semialdehyde relative to the empty vector control.

The gene products of SEQ ID NO: 9 and SEQ ID NO: 12, enhanced by the gene product of sfp, accepted adipate as substrate, as confirmed against the empty vector control (see, FIG. 10), and synthesized adipate semialdehyde.

Example 4

Enzyme Activity of Carboxylate Reductase Using 6-Hydroxyhexanoate as Substrate and Forming 6-Hydroxyhexanal A nucleotide sequence encoding a His-tag was added to the genes from *Mycobacterium marinum, Mycobacterium smegmatis. Mycobacterium smegmatis, Segniliparus rugosus, Mycobacterium massiliense*, and *Segniliparus rotundus* that encode the carboxylate reductases of SEQ ID NOs: 7 to 12, respectively (see FIGS. 9D-9I) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21 [DE3]*E. coli* host. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 6-hydroxyhexanoate to 6-hydroxyhexanal) assays were performed in triplicate in a buffer composed of a final concentration of 50 mM HEPES buffer (pH=7.5), 2 mM 6-hydroxyhexanal, 10 mM MgCl$_2$, 1 mM ATP, and 1 mM NADPH. Each enzyme activity assay reaction was initiated by adding purified carboxylate reductase and phosphopantetheine transferase or the empty vector control to the assay buffer containing the 6-hydroxyhexanoate and then incubated at room temperature for 20 min. The consumption of NADPH was monitored by absorbance at 340 nm. Each enzyme only control without 6-hydroxyhexanoate demonstrated low base line consumption of NADPH. See, FIG. 22.

Figure 11:
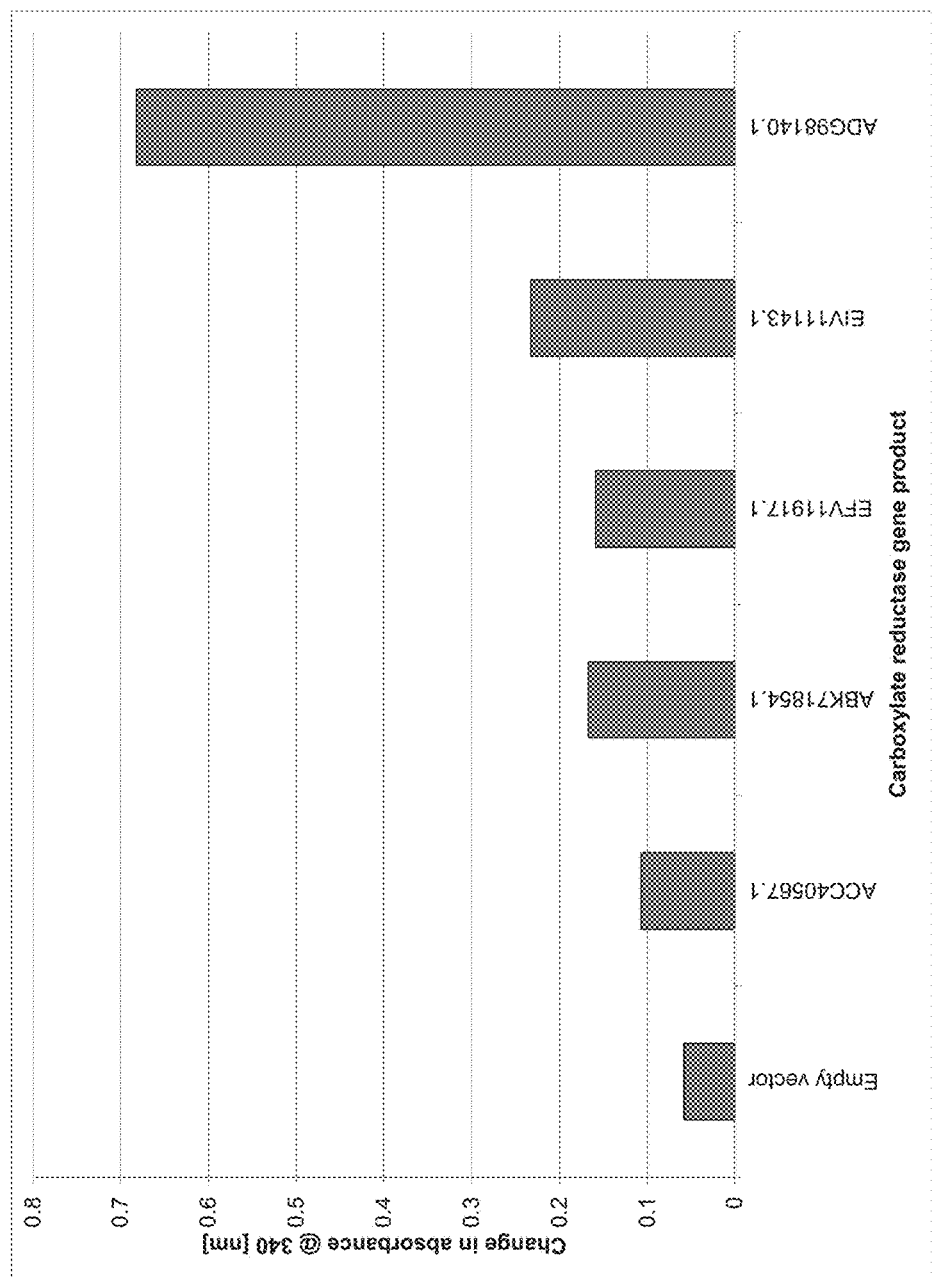
FIG. 11 is a bar graph of the change in absorbance at 340 nm after 20 minutes, which is a measure of the consumption of NADPH and the activity of carboxylate reductases for converting 6-hydroxyhexanoate to 6-hydroxhexanal relative to the empty vector control.

The gene products of SEQ ID NOs: 7 to 12, enhanced by the gene product of sp, accepted 6-hydroxyhexanoate as substrate as confirmed against the empty vector control (see FIG. 11), and synthesized 6-hydroxyhexanal.

Example 5

Enzyme Activity of ω-Transaminase for 6-Aminohexanol, Forming 6-Oxohexanol

A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* genes encoding the ω-transaminases of SEQ ID NOs: 13 to 18, respectively (see FIGS. 9J-9K) such that N-terminal HIS tagged ω-transaminases could be produced. The modified genes were cloned into a pET21a expression vector under the T7 promoter. Each expression vector was transformed into a BL21 [DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanol to 6-oxohexanol) were performed in a buffer composed of a final concentration of 50 mM HEPES buffer (pH=7.5), 10 mM 6-aminohexanol, 10 mM pyruvate, and 100 M pyridoxyl 5' phosphate. Each enzyme activity assay reaction was initiated by adding cell free extract of the ω-transaminase gene product or the empty vector control to the assay buffer containing the 6-aminohexanol and then incubated at 25° C. for 4 hours, with shaking at 250 rpm. The formation of L-alanine was quantified via RP-HPLC.

Each enzyme only control without 6-aminohexanol had low base line conversion of pyruvate to L-alanine. See, FIG. 14.

Figure 19:
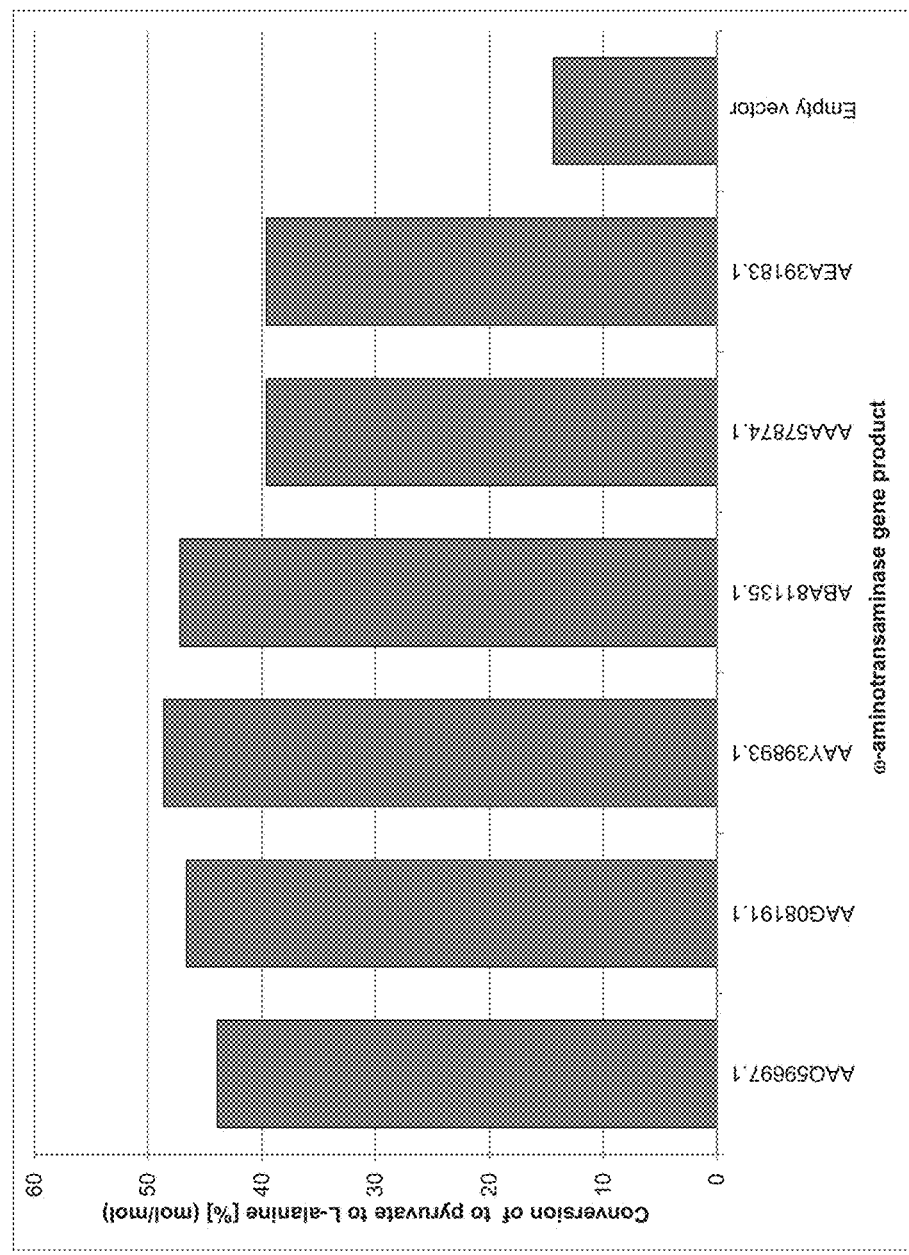
FIG. 19 is a bar graph of the percent conversion after 4 hours of pyruvate to L-alanine (mol/mol) as a measure of the ω-transaminase activity for converting 6-aminohexanol to 6-oxohexanol relative to the empty vector control.

The gene products of SEQ ID NOs: 8 to 13 accepted 6-aminohexanol as substrate as confirmed against the empty vector control (see, FIG. 19) and synthesized 6-oxohexanol as reaction product. Given the reversibility of the ω-transaminase activity (see, Example 2), it can be concluded that the gene products of SEQ ID NOs: 13 to 18 accept 6-aminohexanol as substrate and form 6-oxohexanol.

Example 6

Enzyme Activity of ω-Transaminase Using Hexamethylenediamine as Substrate and Forming 6-Aminohexanal A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* genes encoding the ω-transaminases of SEQ ID NOs: 13 to 18, respectively (see FIGS. 9J-9K) such that N-terminal HIS tagged ω-transaminases could be produced. The modified genes were cloned into a pET21a expression vector under the T7 promoter. Each expression vector was transformed into a BL21 [DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., hexamethylenediamine to 6-aminohexanal) were performed in a buffer composed of a final concentration of 50 mM HEPES buffer (pH=7.5), 10 mM hexamethylenediamine, 10 mM pyruvate, and 100 M pyridoxyl 5' phosphate. Each enzyme activity assay reaction was initiated by adding cell free extract of the (D-transaminase gene product or the empty vector control to the assay buffer containing the hexamethylenediamine and then incubated at 25° C. for 4 hours, with shaking at 250 rpm. The formation of L-alanine was quantified via RP-HPLC.

Each enzyme only control without hexamethylenediamine had low base line conversion of pyruvate to L-alanine. See, FIG. 14.

Figure 17:
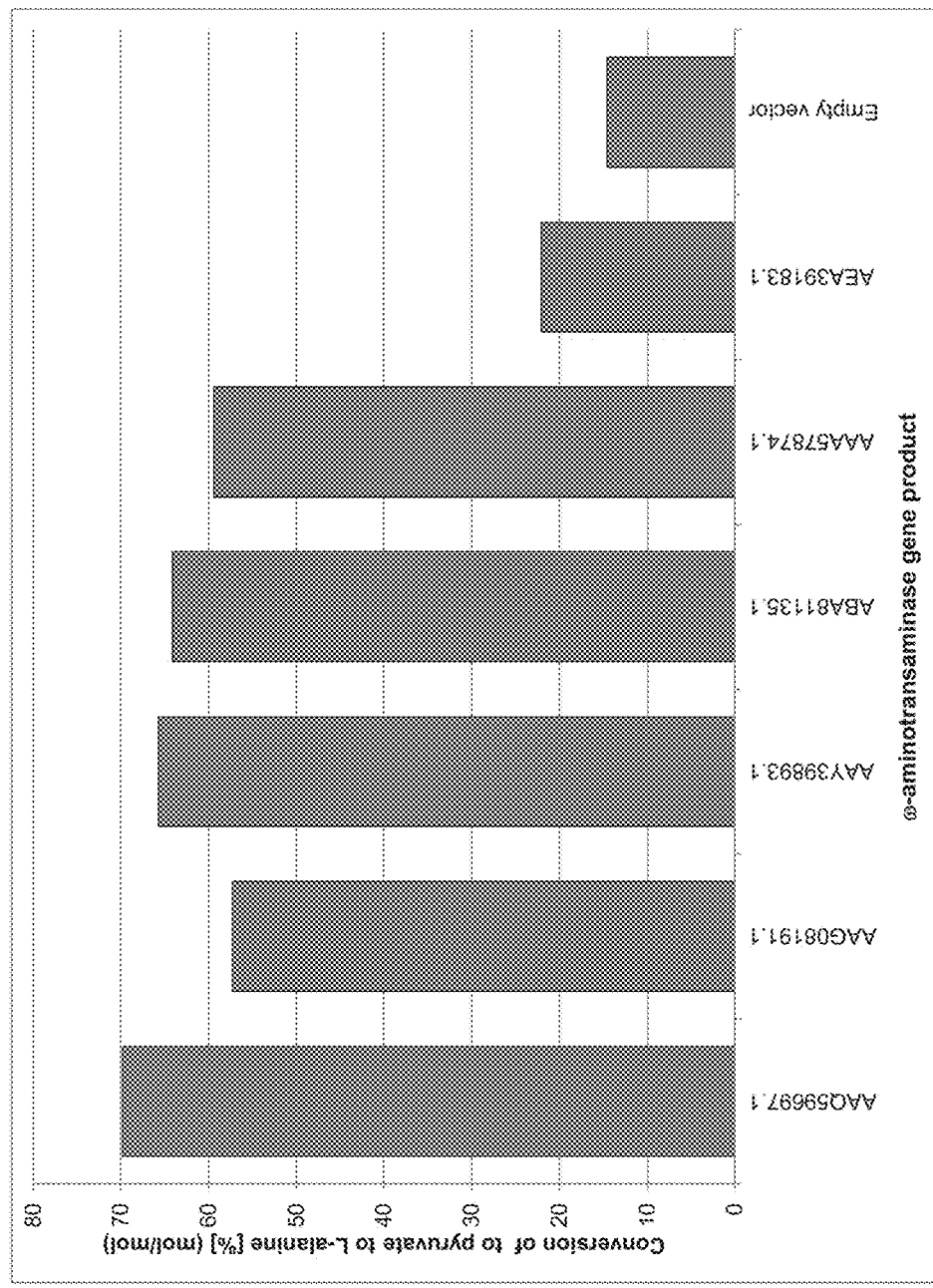
FIG. 17 is a bar graph of the percent conversion after 4 hours of pyruvate to L-alanine (mol/mol) as a measure of the ω-transaminase activity for converting hexamethylenediamine to 6-aminohexanal relative to the empty vector control.

The gene products of SEQ ID NOs: 13 to 18 accepted hexamethylenediamine as substrate as confirmed against the empty vector control (see, FIG. 17) and synthesized 6-aminohexanal as reaction product. Given the reversibility of the ω-transaminase activity (see Example 2), it can be concluded that the gene products of SEQ ID NOs: 13 to 18 accept 6-aminohexanal as substrate and form hexamethylenediamine.

Example 7

Enzyme Activity of Carboxylate Reductase for N6-Acetyl-6-Aminohexanoate, Forming N6-Acetyl-6-Aminohexanal The activity of each of the N-terminal His-tagged carboxylate reductases of SEQ ID NOs: 9, 11, and 12 (see, Example 4 and FIGS. 9F, 9H, and 9I) for converting N6-acetyl-6-aminohexanoate to N6-acetyl-6-aminohexanal was assayed in triplicate in a buffer composed of a final concentration of 50 mM HEPES buffer (pH=7.5), 2 mM N6-acetyl-6-aminohexanoate, 10 mM $MgCl_2$, 1 mM ATP, and 1 mM NADPH. The assays were initiated by adding purified carboxylate reductase and phosphopantetheine transferase or the empty vector control to the assay buffer containing the N6-acetyl-6-aminohexanoate then incubated at room temperature for 20 minutes. The consumption of NADPH was monitored by absorbance at 340 nm. Each enzyme only control without N6-acetyl-6-aminohexanoate demonstrated low base line consumption of NADPH. See, FIG. 22.

Figure 12:
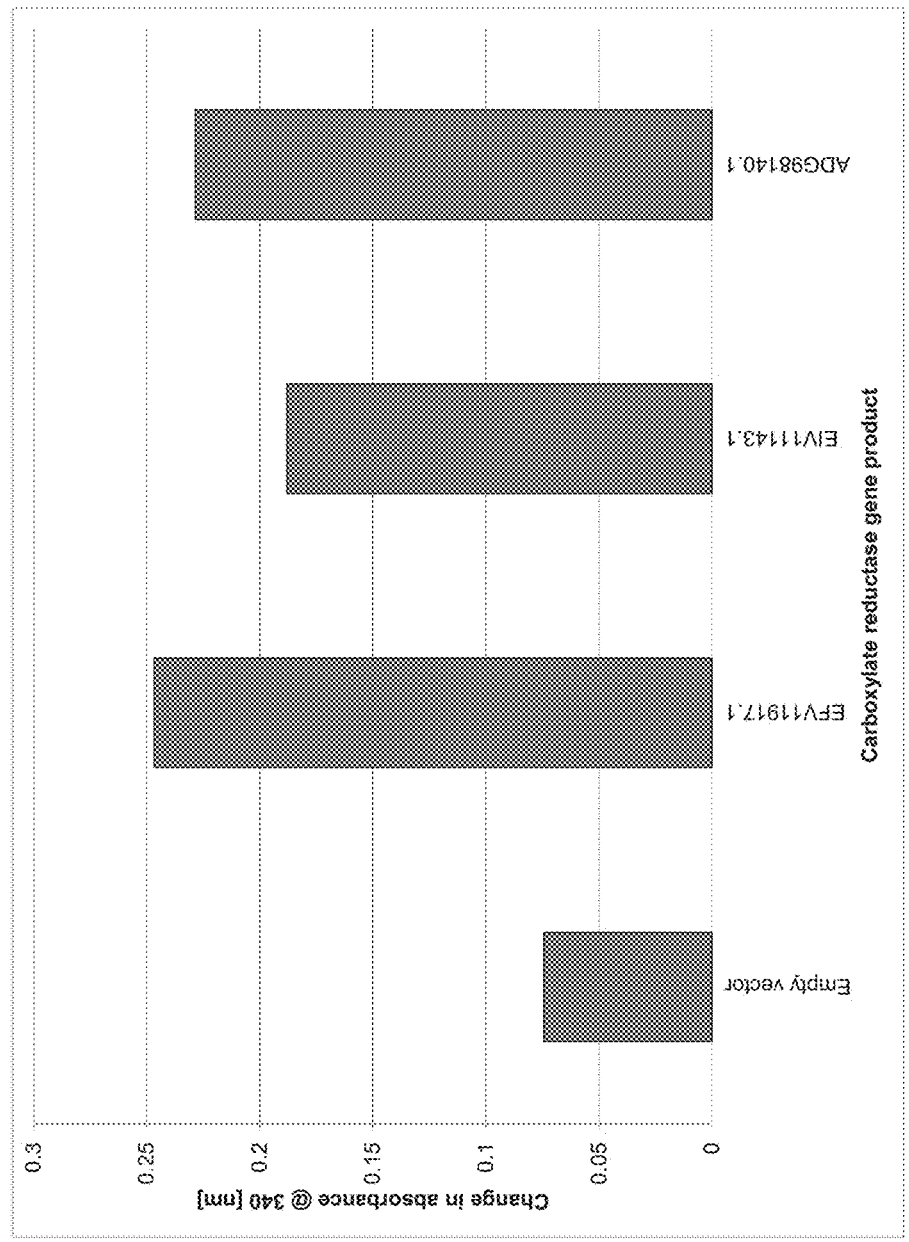
FIG. 12 is a bar graph of the change in absorbance at 340 nm after 20 minutes, which is a measure of the consumption of NADPH and the activity of carboxylate reductases for converting N6-acetyl-6-aminohexanoate to N6-acetyl-6-aminohexanal relative to the empty vector control.

The gene products of SEQ ID NOs: 9, 11, and 12, enhanced by the gene product of sfp, accepted N6-acetyl-6-aminohexanoate as substrate as confirmed against the empty vector control (see, FIG. 12), and synthesized N6-acetyl-6-aminohexanal.

Example 8

Enzyme Activity of ω-Transaminase Using N6-Acetyl-1,6-Diaminohexane, and Forming N6-Acetyl-6-Aminohexanal The activity of the N-terminal His-tagged ω-transaminases of SEQ ID NOs: 13 to 18 (see, Example 6 and FIGS. 9J-9K) for converting N6-acetyl-1,6-diaminohexane to N6-acetyl-6-aminohexanal was assayed using a buffer composed of a final concentration of 50 mM HEPES buffer (pH=7.5), 10 mM N6-acetyl-1,6-diaminohexane, 10 mM pyruvate and 100 µM pyridoxyl 5' phosphate. Each enzyme activity assay reaction was initiated by adding a cell free extract of the ω-transaminase or the empty vector control to the assay buffer containing the N6-acetyl-1,6-diaminohexane then incubated at 25° C. for 4 hours, with shaking at 250 rpm. The formation of L-alanine was quantified via RP-HPLC.

Each enzyme only control without N6-acetyl-1,6-diaminohexane demonstrated low base line conversion of pyruvate to L-alanine. See, FIG. 14.

Figure 18:
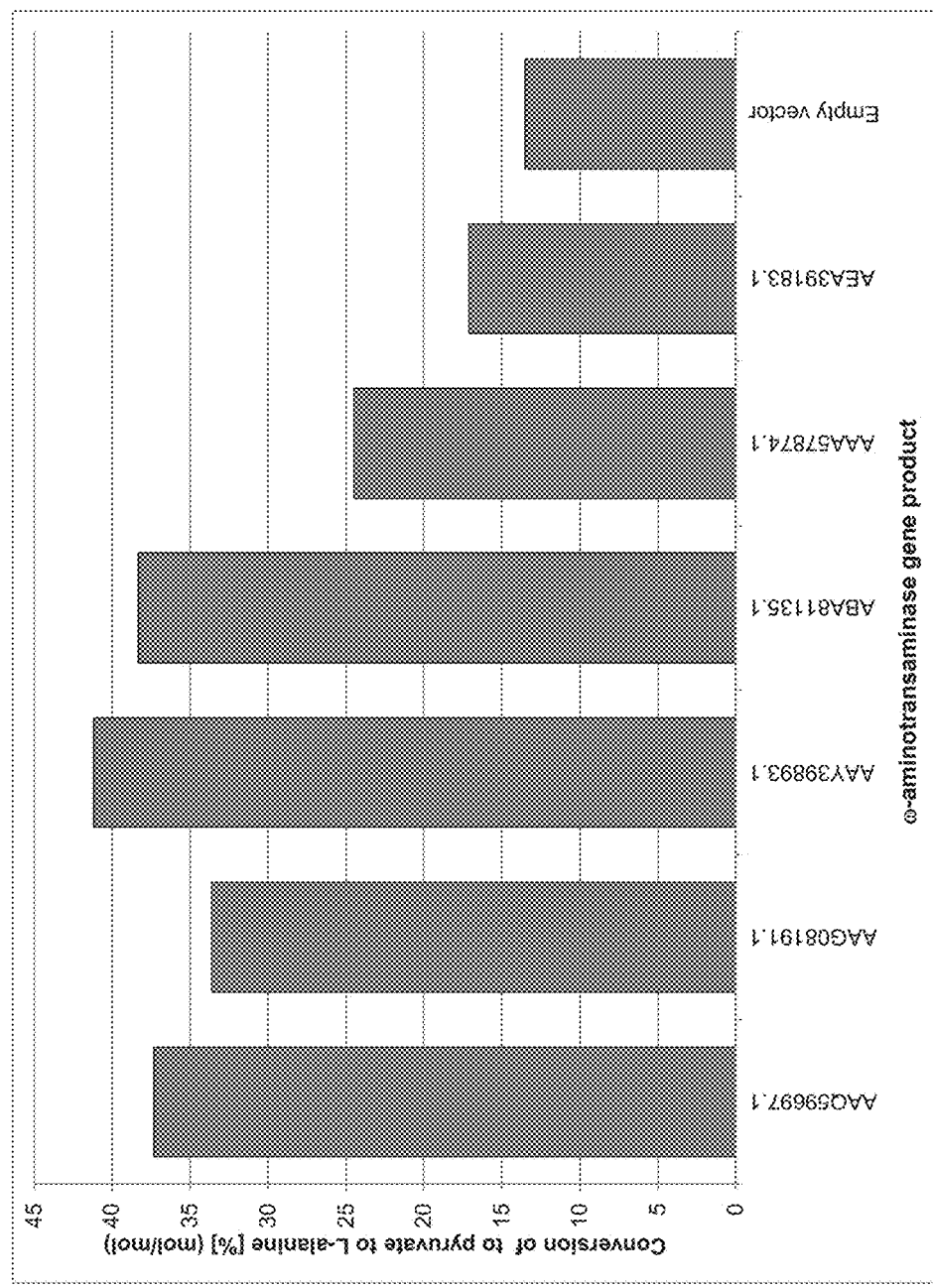
FIG. 18 is a bar graph of the percent conversion after 4 hours of pyruvate to L-alanine (mol/mol) as a measure of the ω-transaminase activity for converting N6-acetyl-1,6-diaminohexane to N6-acetyl-6-aminohexanal relative to the empty vector control.

The gene product of SEQ ID NOs: 13 to 18 accepted N6-acetyl-1,6-diaminohexane as substrate as confirmed against the empty vector control (see, FIG. 18) and synthesized N6-acetyl-6-aminohexanal as reaction product.

Given the reversibility of the ω-transaminase activity (see, Example 2), the gene products of SEQ ID NOs: 13 to 18 accept N6-acetyl-6-aminohexanal as substrate forming N6-acetyl-1,6-di aminohexane.

Example 9

Enzyme Activity of Carboxylate Reductase Using Adipate Semialdehyde as Substrate and Forming Hexanedial The N-terminal His-tagged carboxylate reductase of SEQ ID NO: 12 (see, Example 4 and FIG. 9I) was assayed using adipate semialdehyde as substrate. The enzyme activity assay was performed in triplicate in a buffer composed of a final concentration of 50 mM HEPES buffer (pH=7.5), 2 mM adipate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the adipate semialdehyde and then incubated at room temperature for 20 minutes. The consumption of NADPH was monitored by absorbance at 340 nm. The enzyme only control without adipate semialdehyde demonstrated low base line consumption of NADPH. See, FIG. 22.

Figure 13:
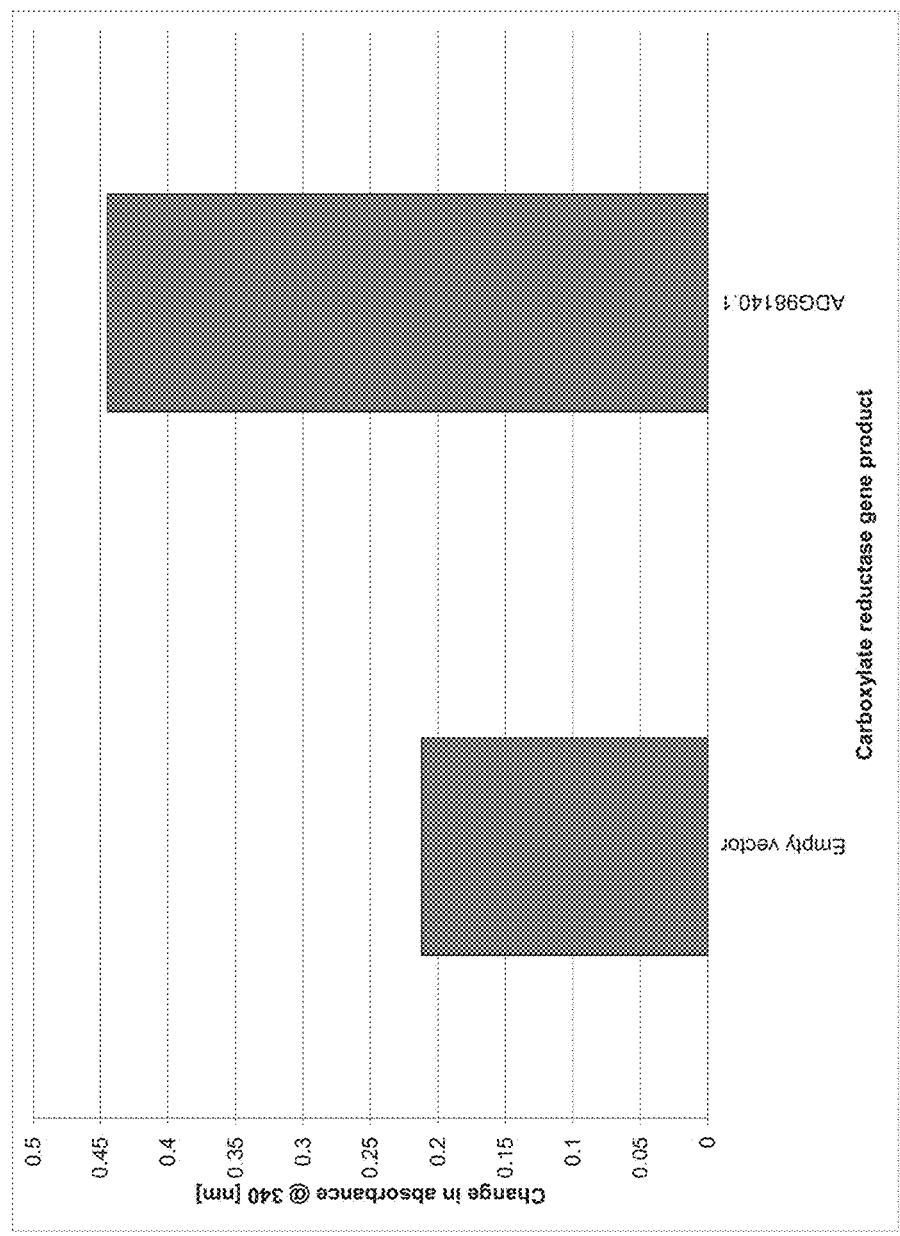
FIG. 13 is a bar graph of the change in absorbance at 340 nm after 20 minutes, which is a measure of the consumption of NADPH and activity of carboxylate reductases for converting adipate semialdehyde to hexanedial relative to the empty vector control.

The gene product of SEQ ID NO: 12, enhanced by the gene product of sfp, accepted adipate semialdehyde as substrate as confirmed against the empty vector control (see FIG. 13) and synthesized hexanedial.

Example 10

Enzyme Activity of Pimeloyl-[Acp] Methyl Ester Methylesterase Using Adipyl-CoA Methyl Ester as Substrate and Forming Adipyl-CoA A sequence encoding an C-terminal His-tag was added to the gene from *Escherichia coli* encoding the pimeloyl-[acp] methyl ester methylesterase of SEQ ID NO: 6 (see FIG. 9C) such that C-terminal HIS tagged pimeloyl-[acp] methyl ester methylesterase could be produced. The resulting modified gene was cloned into a pET28b+ expression vector under control of the T7 promoter and the expression vector was transformed into a BL21 [DE3] *E. coli* host. The resulting recombinant *E. coli* strain was cultivated at 37° C. in a 500 mL shake flask culture containing 100 mL LB media and antibiotic selection pressure, with shaking at 230 rpm. Each culture was induced overnight at 18° C. using 0.3 mM IPTG.

The pellet from each induced shake flask culture was harvested via centrifugation. Each pellet was resuspended and lysed via sonication. The cell debris was separated from the supernatant via centrifugation. The pimeloyl-[acp] methyl ester methylesterase was purified from the supernatant using Ni-affinity chromatography, buffer exchanged and concentrated into 20 mM HEPES buffer (pH=7.5) via ultrafiltration and stored at 4° C.

Enzyme activity assays converting adipyl-CoA methyl ester to adipyl-CoA were performed in triplicate in a buffer composed of a final concentration of 25 mM Tris-HCl buffer (pH=7.0) and 5 [mM] adipyl-CoA methyl ester. The enzyme activity assay reaction was initiated by adding pimeloyl-[acp] methyl ester methylesterase to a final concentration of 10 µM to the assay buffer containing the adipyl-CoA methyl ester and incubated at 30° C. for 1 hour, with shaking at 250 rpm. The formation of adipyl-CoA was quantified via LC-MS.

The substrate only control without enzyme showed trace quantities of the substrate adipyl-CoA. See FIG. 20. The pimeloyl-[acp] methyl ester methylesterase of SEQ ID NO: 6 accepted adipyl-CoA methyl ester as substrate and synthesized adipyl-CoA as reaction product as confirmed via LC-MS. See, FIG. 20.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of shielding a carbon chain aliphatic backbone functionalized with terminal carboxyl groups in a recombinant host, said method comprising enzymatically converting 2,3-dehydroadipic acid to 2,3-dehydroadipate methyl ester in said host using a polypeptide having the activity of a fatty acid O-methyltransferase, wherein said polypeptide having the activity of a fatty acid O-methyltransferase has at least 85% sequence identity to an amino acid sequence set forth in any one of SEQ ID NOs: 1 to 3.

2. The method of claim 1, said method further comprising enzymatically converting 2,3-dehydroadipate methyl ester to adipyl-CoA using at least one polypeptide having the activity of a CoA ligase, a trans-2-enoyl-CoA reductase, or a pimelyl-[acp] methyl ester esterase, wherein said polypeptide having the activity of a CoA ligase has at least 85% sequence identity to an amino acid sequence set forth in SEQ ID NO: 22 or SEQ ID NO: 23, said polypeptide having the activity of a trans-2-enoyl-CoA reductase has at least 85% sequence identity to an amino acid sequence set forth in SEQ ID NO: 26 or SEQ ID NO: 27, and/or said polypeptide having the activity of a pimelyl-[acp] methyl ester esterase has at least 85% sequence identity to the amino acid sequence set forth in SEQ ID NO: 6, said method optionally further comprising enzymatically converting adipyl-CoA to adipic acid, 6 aminohexanoate, 6-hydroxyhexanoate, caprolactam, hexamethylenediamine, or 1,6 hexanediol.

3. The method of claim 1, wherein one or more steps of said method are performed by fermentation.

4. The method of claim 1, wherein said host is subjected to a cultivation strategy under aerobic, anaerobic, microaerobic, or mixed oxygen/denitrification cultivation conditions.

5. The method of claim 1, wherein said host is cultured under conditions of phosphate, oxygen, and/or nitrogen limitation.

6. The method of claim 1, wherein said host is retained using a ceramic membrane to maintain a high cell density during fermentation.

7. The method of claim 3, wherein the principal carbon source fed to the fermentation derives from biological or non-biological feedstocks.

8. The method of claim 7, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

9. The method of claim 7, wherein the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

10. The method of claim 1, wherein said host comprises one or more of the following attenuated enzymes: polyhydroxyalkanoate synthase, acetyl-CoA thioesterase, acetyl-CoA specific β-ketothiolase, phosphotransacetylase forming acetate, acetate kinase, lactate dehydrogenase, menaquinol-fumarate oxidoreductase, alcohol dehydrogenase forming ethanol, triose phosphate isomerase, pyruvate decarboxylase, glucose-6-phosphate isomerase, transhydrogenase dissipating a NADPH imbalance, glutamate dehydrogenase dissipating a NADPH imbalance, NADH/NADPH-utilizing glutamate dehydrogenase, pimeloyl-CoA dehydrogenase, acyl-CoA dehydrogenase accepting C7 building blocks and central precursors as substrates, glutaryl-CoA dehydrogenase, or adipyl-CoA synthetase.

11. The method of claim 1, wherein said host overexpresses one or more genes encoding at least one polypeptide having acetyl-CoA synthetase, 6-phosphogluconate dehydrogenase, transketolase, puridine nucleotide transhydrogenase, formate dehydrogenase, glyceraldehyde-3P-dehydrogenase, malic enzyme, glucose-6-phosphate dehydrogenase, fructose 1,6 diphosphatase, L-alanine dehydrogenase, PEP carboxylase, pyruvate carboxylase, PEP carboxykinase, PEP synthase, L-glutamate dehydrogenase specific to the NADPH used to generate a co-factor imbalance, methanol dehydrogenase, formaldehyde dehydrogenase, lysine transporter, dicarboxylate transporter, S-adenosylmethionine synthetase, 3-phosphoglycerate dehydrogenase, 3-phosphoserine aminotransferase, phosphoserine phosphatase, or a multidrug transporter activity.

12. The method of claim 1, wherein the host is a pro-karyote selected from the genus *Escherichia*, the genus *Clostridia*, the genus *Corynebacteria*, the genus *Cupriavidus*, the genus *Pseudomonas*, the genus *Delftia*, the genus *Bacillus*, the genus *Lactobacillus*, the genus *Lactococcus*, and the genus *Rhodococcus*, or a eukaryote selected from the genus *Aspergillus*, the genus *Saccharomyces*, the genus *Pichia*, the genus *Yarrowia*, the genus *Issatchenkia*, the genus *Debaryomyces*, the genus *Arxula*, and the genus *Kluyveromyces*.

13. A method of producing 2,3-dehydroadipyl-CoA methyl ester in a recombinant host, said method comprising enzymatically converting 2,3-dehydroadipic acid to 2,3-dehydroadipate methyl ester using a polypeptide having fatty acid O-methyltransferase activity, wherein said polypeptide having fatty acid O-methyltransferase has at least 85% sequence identity to an amino acid sequence set forth in any one of SEQ ID NOs: 1 to 3, and further enzymatically converting 2,3-dehydroadipate methyl ester to 2,3-dehydroadipyl-CoA methyl ester using a polypeptide having the activity of a CoA ligase, wherein said polypeptide having the activity of a CoA ligase has at least 85% sequence identity to SEQ ID NO: 22 or SEQ ID NO: 23,
  wherein the 2,3-dehydroadipic acid is enzymatically produced from 2,3-dehydroadipyl-CoA using a polypeptide having thioesterase activity or a protein having CoA-transferase activity, wherein said polypeptide having thioesterase activity has at least 85% sequence identity to an amino acid sequence set forth in any one of SEQ ID NOs: 4, 5, or 21 or at least 85% sequence identity to an amino acid sequence encoding a gene product of yciA or ACOT13 and said protein having CoA-transferase activity has a first subunit having at least 85% sequence identity to the amino acid sequence set forth in SEQ ID NO: 24 and a second subunit having at least 85% sequence identity to the amino acid sequence set forth in SEQ ID NO: 25,
  the method optionally further comprising enzymatically converting 2,3-dehydroadipyl methyl ester to adipyl-CoA methyl ester using a polypeptide having trans-2-enoyl-CoA reductase activity, wherein said polypeptide having trans-2-enoyl-CoA reductase activity has at least 85% sequence identity to an amino acid sequence set forth in SEQ ID NO: 26 or SEQ ID NO: 27.

14. The method of claim 13, said method further comprising enzymatically converting 2,3-dehydroadipyl-CoA methyl ester to adipyl-CoA,
  said method comprising enzymatically converting 2,3-dehydroadipyl-CoA methyl ester to adipyl-CoA methyl ester using a polypeptide having trans-2-enoyl-CoA reductase activity, wherein said polypeptide having trans-2-enoyl-CoA reductase activity has at least 85% sequence identity to an amino acid sequence set forth in SEQ ID NO: 26 or SEQ ID NO: 27, and further enzymatically converting adipyl-CoA methyl ester to adipyl-CoA using a polypeptide having pimelyl-[acp] methyl ester esterase activity, wherein said polypeptide having pimelyl-[acp] methyl ester esterase activity has at least 85% sequence identity to the amino acid sequence set forth in SEQ ID NO: 6.

15. The method of claim 1, further comprising enzymatically converting adipyl-CoA to a product selected from adipic acid, 6-aminohexanoate, 6-hydroxyhexanoate, caprolactam, hexamethylenediamine, and 1,6-hexanediol.

16. The method of claim 14, said method further comprising enzymatically converting adipyl-CoA to adipate semialdehyde, wherein
  said method comprises enzymatically converting adipyl-CoA to adipate semialdehyde using a polypeptide having acetylating aldehyde dehydrogenase activity, wherein said polypeptide having acetylating aldehyde dehydrogenase activity has at least 85% sequence identity to an amino acid sequence encoding a gene product of PduP; or
  said method comprises enzymatically converting adipyl-CoA to adipic acid using a polypeptide having thioesterase or CoA ligase activity or a protein having CoA transferase activity and further enzymatically converting adipic acid to adipate semialdehyde using a polypeptide having carboxylate reductase activity, wherein said polypeptide having thioesterase activity has at least 85% sequence identity to an amino acid sequence set forth in any one of SEQ ID NOs: 4, 5, or 21 or at least 85% sequence identity to an amino acid sequence encoding a gene product of yciA or ACOT13, said polypeptide having CoA ligase activity has at least 85% sequence identity to an amino acid sequence set forth in SEQ ID NO: 22 or SEQ ID NO: 23, said protein having CoA transferase activity has a first subunit having at least 85% sequence identity to the amino acid sequence set forth in SEQ ID NO: 24 and a second subunit having at least 85% sequence identity to the amino acid sequence set forth in SEQ ID NO: 25, and said polypeptide having carboxylate reductase activity has at least 85% sequence identity to an amino acid sequence set forth in any one of SEQ ID NOs: 7 to 12.

17. The method of claim 15, said method comprising enzymatically converting adipyl-CoA to adipic acid using a polypeptide having thioesterase or CoA ligase or a protein having CoA transferase activity, wherein said polypeptide having thioesterase activity has at least 85% sequence identity to an amino acid sequence set forth in any one of SEQ ID NOs: 4, 5, or 21 or at least 85% sequence identity to an amino acid sequence encoding a gene product of yciA or ACOT13, said polypeptide having CoA ligase activity has at least 85% sequence identity to an amino acid sequence set forth in SEQ ID NO: 22 or SEQ ID NO: 23, and said protein having CoA transferase activity has a first subunit having at least 85% sequence identity to the amino acid sequence set forth in SEQ ID NO: 24 and a second subunit having at least 85% sequence identity to an amino acid sequence set forth in SEQ ID NO: 25.

18. The method of claim 16, said method further comprising enzymatically converting adipate semialdehyde to adipic acid using a polypeptide having 4-oxobutanoate dehydrogenase, 5-oxopentanoate dehydrogenase, 6-oxohexanoate dehydrogenase, 7-oxoheptanoate dehydrogenase, or aldehyde dehydrogenase activity, wherein said polypeptide having 4-oxobutanoate dehydrogenase activity has at least 85% sequence identity to an amino acid sequence encoding a gene product of gbd, said polypeptide having 5-oxopentanoate dehydrogenase activity has at least 85% sequence identity to an amino acid sequence encoding a gene product of cpnE, said polypeptide having 6-oxohexanoate dehydrogenase activity has at least 85% sequence identity to an amino acid sequence encoding a gene product of chnE, said polypeptide having 7-oxoheptanoate dehydrogenase activity has at least 85% sequence identity to an amino acid sequence encoding a gene product of thnG, and said polypeptide having aldehyde dehydrogenase activity is classified under EC 1.2.1.3.

19. The method of claim 16, said method further comprising enzymatically converting adipate semialdehyde to 6-aminohexanoate using a polypeptide having ω-transaminase activity, wherein said polypeptide having w-transaminase activity has at least 85% sequence identity to an amino acid sequence set forth in any one of SEQ ID NOs: 13 to 18,
said method optionally further comprising enzymatically covering 6-aminohexanoate to caprolactam using a polypeptide having hydroxy-cyclohexan-1-one amidohydrolase activity, wherein said polypeptide having hydroxy-cyclohexan-1-one amidohydrolase activity is classified under EC 3.5.2.-.

20. The method of claim 16, said method further comprising enzymatically converting adipate semialdehyde to hexamethylenediamine using at least one polypeptide having ω-transaminase or carboxylate reductase activity, wherein said polypeptide having ω-transaminase activity has at least 85% sequence identity to an amino acid sequence set forth in any one of SEQ ID NOs: 13 to 18 and said polypeptide having carboxylate reductase activity has at least 85% sequence identity to an amino acid sequence set forth in any one of SEQ ID NOs: 7 to 12.

21. The method of claim 16, said method further comprising enzymatically converting adipate semialdehyde to 6-hydroxyhexanoate using a polypeptide having 6-hydroxyhexanoate dehydrogenase, 5-hydroxypentanoate dehydrogenase, or 4-hydroxybutyrate dehydrogenase activity, wherein said polypeptide having 6-hydroxyhexanoate dehydrogenase activity has at least 85% sequence identity to an amino acid sequence encoding a gene product of chnD, said polypeptide having 5-hydroxypentanoate dehydrogenase activity has at least 85% sequence identity to an amino acid sequence encoding a gene product of cpnD, and said polypeptide having 4-hydroxybutyrate dehydrogenase activity has at least 85% sequence identity to an amino acid sequence encoding a gene product of gbd,
said method optionally further comprising enzymatically converting 6-hydroxyhexanoate to 1,6-hexanediol using at least one polypeptide having carboxylate reductase or alcohol dehydrogenase activity, wherein said polypeptide having carboxylate reductase activity has at least 85% sequence identity to an amino acid sequence set forth in any one of SEQ ID NOs: 7 to 12 and said polypeptide having alcohol dehydrogenase activity has at least 85% sequence identity to an amino acid sequence encoding a gene product of YMR318C or yqhD.

* * * * *